US007850957B2

(12) United States Patent
Qian et al.

(10) Patent No.: US 7,850,957 B2
(45) Date of Patent: Dec. 14, 2010

(54) ADENOVIRUS/ALPHAVIRUS HYBRID VECTOR FOR THE EFFECTIVE ADMINISTRATION AND EXPRESSION OF THERAPEUTIC GENES IN TUMOUR CELLS

(75) Inventors: Cheng Qian, Gorraiz (ES); Min Guan, Arcadia, CA (US); Cristian Smerdou Picazo, Pamplona (ES); Jesús Prieto Valtueña, Pamplona (ES)

(73) Assignee: Proyecto De Biomecdicina Cima, S.L., Pamplona (Navarra) (ES)

( * ) Notice: Subject to any disclaimer, the term of this patent is extended or adjusted under 35 U.S.C. 154(b) by 0 days.

(21) Appl. No.: 11/569,303

(22) PCT Filed: May 18, 2005

(86) PCT No.: PCT/ES2005/000277

§ 371 (c)(1),
(2), (4) Date: Dec. 18, 2006

(87) PCT Pub. No.: WO2005/112541

PCT Pub. Date: Dec. 1, 2005

(65) Prior Publication Data

US 2007/0224170 A1 Sep. 27, 2007

(30) Foreign Application Priority Data

May 20, 2004 (ES) ................................ 200401219

(51) Int. Cl.
*A01N 63/00* (2006.01)
*A61K 39/12* (2006.01)
*C12N 15/00* (2006.01)

(52) U.S. Cl. ..................... 424/93.2; 424/199.1; 435/455
(58) Field of Classification Search ................ 424/93.2, 424/199.1; 435/455
See application file for complete search history.

(56) References Cited

U.S. PATENT DOCUMENTS

| 5,981,225 | A | 11/1999 | Kochanek et al. |
| 5,985,846 | A | 11/1999 | Kochanek |
| 6,238,858 | B1 * | 5/2001 | Ramsey et al. .................. 435/5 |
| 6,566,093 | B1 | 5/2003 | Liljestrom et al. |
| 6,824,770 | B1 * | 11/2004 | Falck-Pedersen .......... 424/93.2 |
| 7,199,279 | B2 * | 4/2007 | Rapp ............................. 800/19 |
| 2002/0081277 | A1 * | 6/2002 | Trinchieri et al. .......... 424/85.2 |
| 2002/0164799 | A1 * | 11/2002 | Little et al. .................. 435/456 |
| 2004/0005293 | A1 * | 1/2004 | Vandendriessche et al. 424/93.2 |
| 2005/0255511 | A1 * | 11/2005 | Debinski et al. ................ 435/6 |

FOREIGN PATENT DOCUMENTS

| EP | 0797678 | 3/2001 |
| EP | 0651890 | 4/2003 |
| WO | 9815636 | 4/1998 |
| WO | 9822143 | 5/1998 |
| WO | 9925858 | 5/1999 |
| WO | WO 99/25859 | * | 5/1999 |
| WO | 9932647 | 7/1999 |
| WO | 0046360 | 8/2000 |
| WO | 0073424 | 12/2000 |
| WO | 0172341 | 10/2001 |
| WO | 0238782 | 5/2002 |

OTHER PUBLICATIONS

Rayner et al., "Alphavirus Vectors and Vaccination," Rev. Med. Virol., vol. 12, (2002) pp. 279-296.
Volpers et al., "Adenoviral Vectors for Gene Transfer and Therapy," J. Gene Med., vol. 6, (2004) pp. S164-S171.
Schiedner et al., "Variables Affecting in vivo Performance of High-Capacity Adenoviral Vectors," J. Virol., vol. 76, No. 4, (2002) pp. 1600-1609.
Strauss, James H., et al., The Alphaviruses: Gene Expression, Replication, and Evolution, Microbiological Reviews, 1994, pp. 491-562, vol. 58, No. 3.
Glasgow, Gwendoline M., et al., The Semliki Forest virus vector induces p53-independent apoptosis, Journal of General Virology, 1998, pp. 2405-2410, vol. 79.
Liljestrom, Peter, et al., A New Generation of Animal Cell Expression Vectors Based on the Semliki Forest Virus Replicon, Bio/Technology, 1991, pp. 1356-1361, vol. 9.
Shi, Yu-Jun, et al., Construction of a targeting adenoviral vector carrying AFP promoter for expression EGFP gene in AFP-producing hepatocarcinoma cell, World Journal of Gastroenterology, 2004, pp. 186-189, vol. 10, No. 2.
Kaneko, Shuichi, et al., Adenovirus-mediated Gene Therapy of Hepatocellular Carcinoma Using Cancer-specific Gene Expression, Cancer Research, 1995, pp. 5283-5287, vol. 55.
Guan, Min, et al., Increased Efficacy and Safety in the Treatment of Experimental Liver Cancer with a Novel Adenovirus-Alphavirus Hybrid Vector, Cancer Research, 2006, pp. 1620-1629, vol. 66, No. 3.
McGrory, W.J., et al., Short Communications, A Simple Technique for the Rescue of Early Region I Mutations into Infectious Human Adenovirus Type 5, Virology, 1988, pp. 614-617, vol. 163.

* cited by examiner

*Primary Examiner*—Fereydoun G Sajjadi
(74) *Attorney, Agent, or Firm*—Andrew Gerschutz; Tristan A. Fuierer; Moore & Van Allen, PLLC

(57) ABSTRACT

The present invention relates to a genic expression adenoviral hybrid vector characterized in that it contains at least the following elements, oriented in the direction 5' to 3': i. a first chain of adenoviral origin comprising a first inverted terminal repeat (ITR) sequence and a signal sequence for packaging of the adenovirus; ii. a first non-encoding stuffer sequence; iii. a sequence corresponding to a tissue specific promoter; iv. a chain of cDNA derived from an alphavirus, the sequence of which is partly complementary to an alphaviral RNA sequence, comprising at least a sequence encoding for at least one exogenous gene of interest; v. a polyadenylation sequence; and vi. a second adenoviral inverted terminal repeat (ITR) sequence, it preferably relates to an adenoviral hybrid vector comprising as exogenous gene of interest the therapeutic gene of mammalian interleukin IL-12 and even more preferably human interleukin hIL-12; and to the use of the hybrid vector in a process for transferring genetic material to a cell, particularly a tumor cell that preferably expresses alpha-fetoprotein (AFP), and to its use for inducing an immune response against foreign antigens.

29 Claims, 17 Drawing Sheets

A
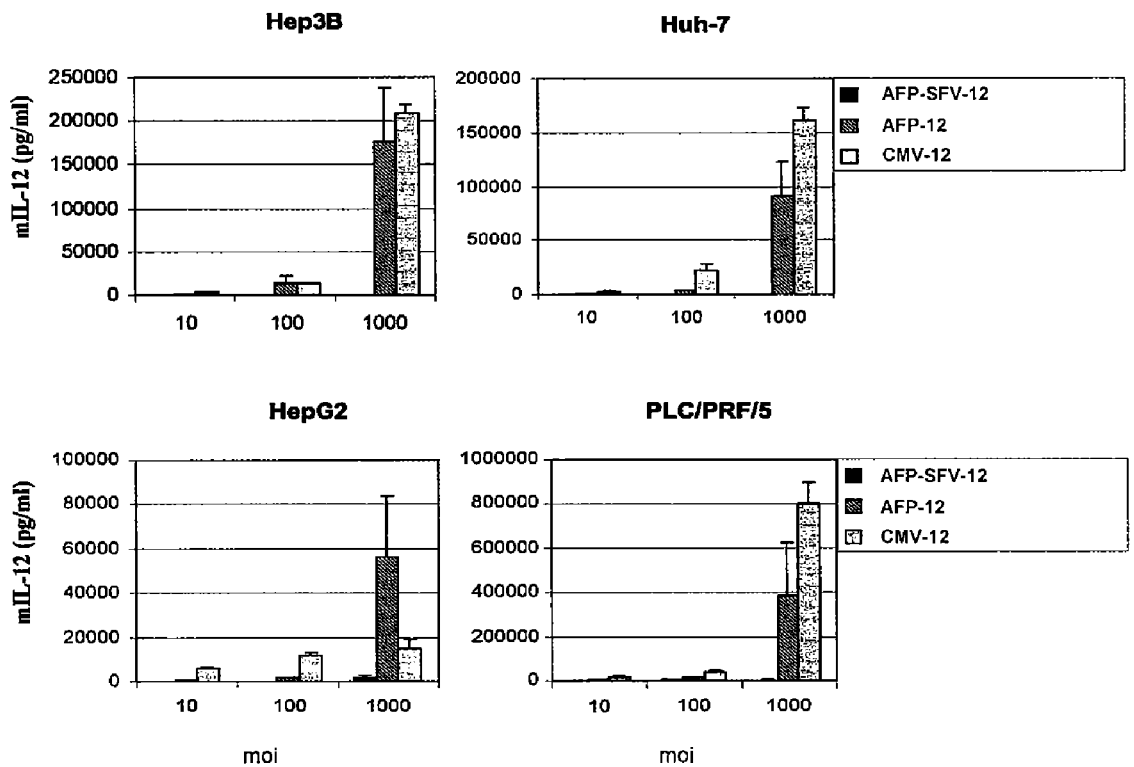
B
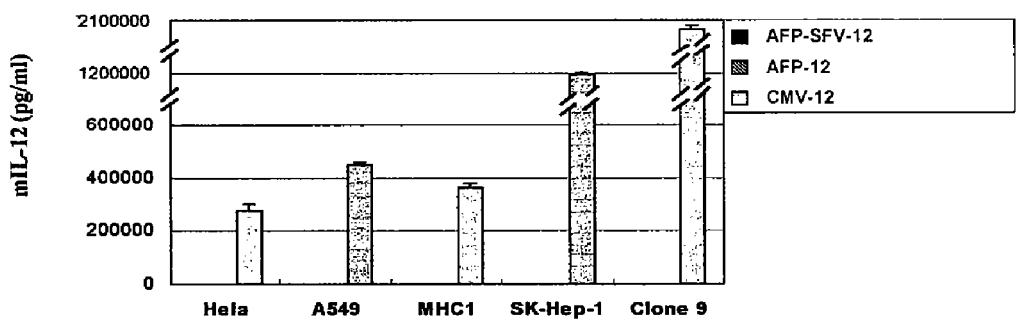
Figure 3

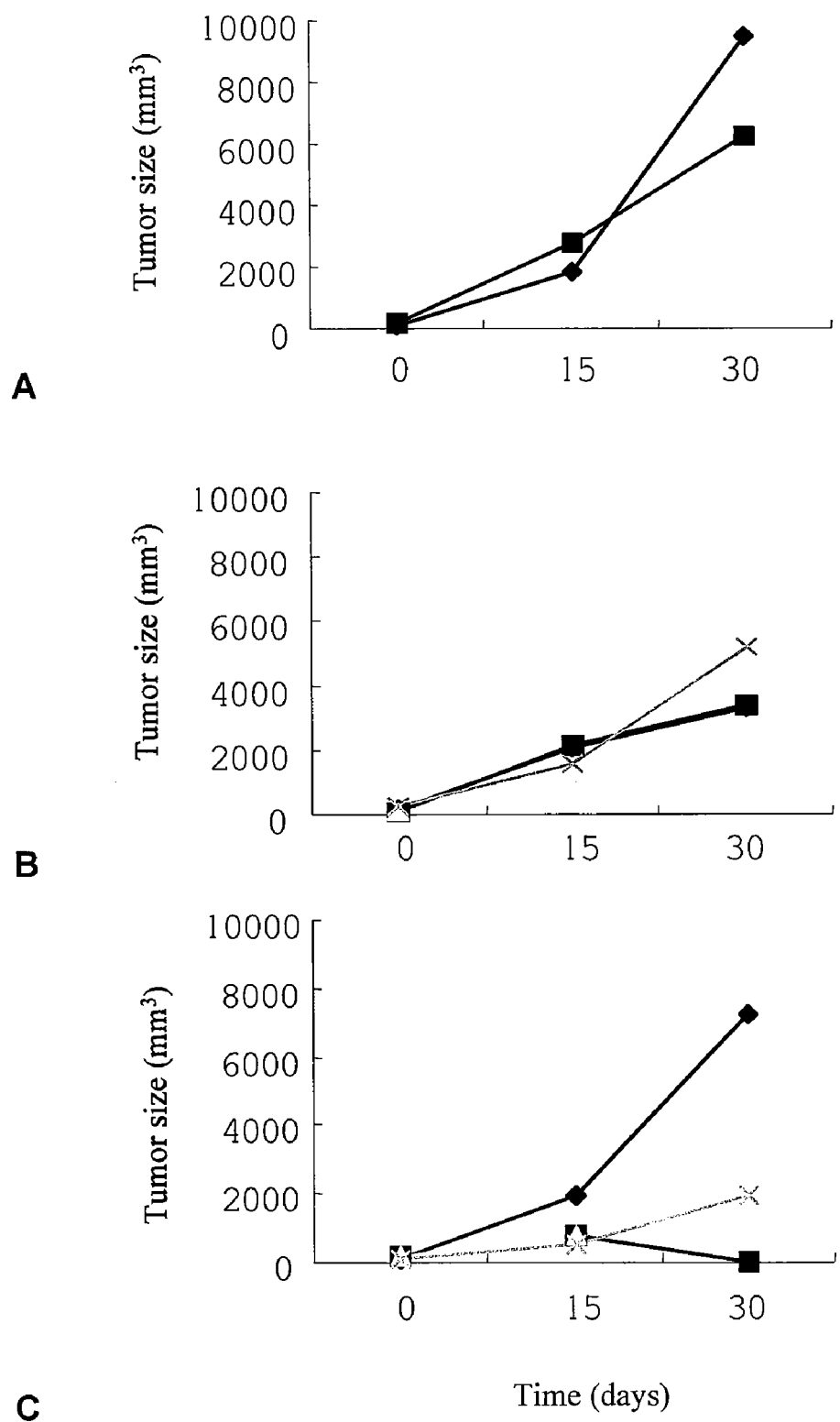
Figure 10 : $10^{11}$

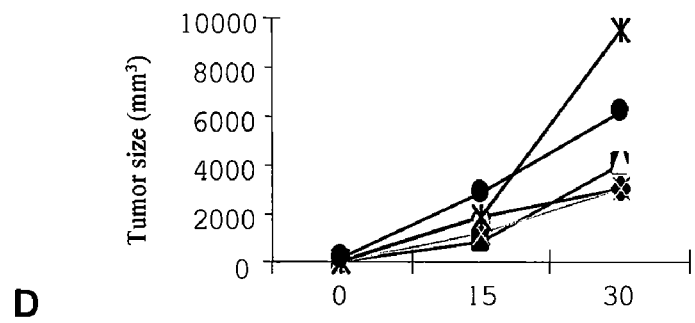
D
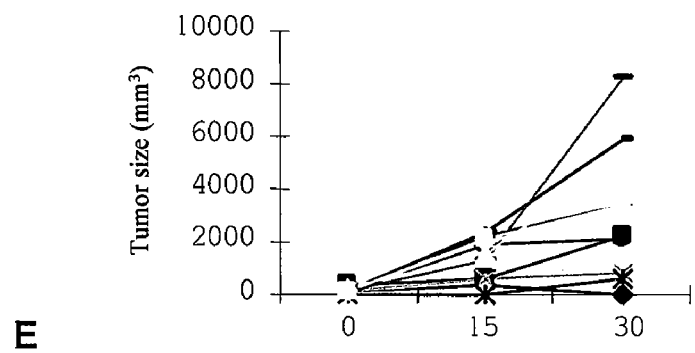
E
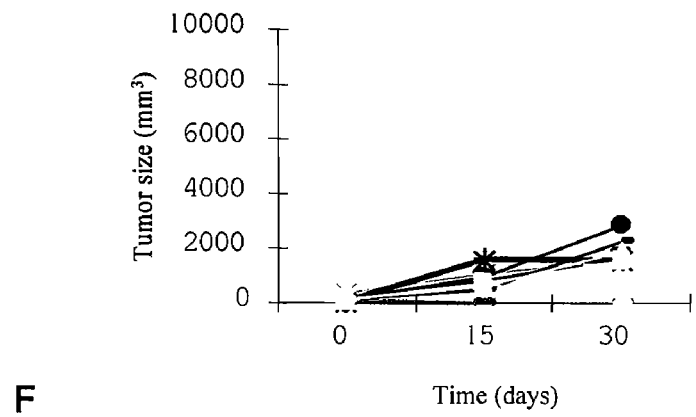
F
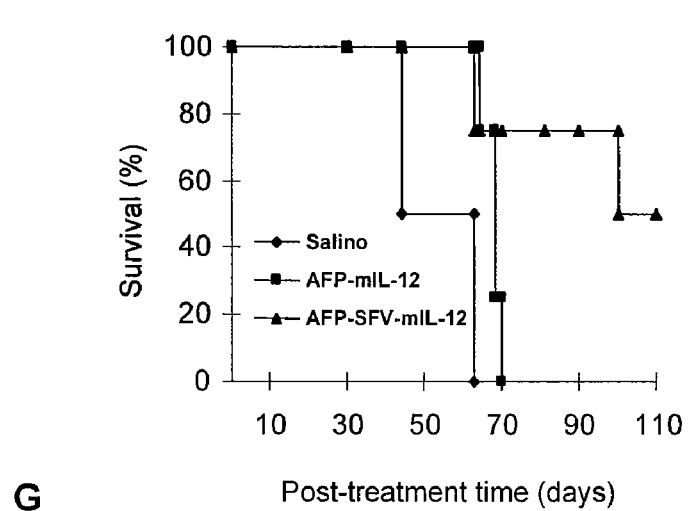
G
Figure 10 : 2x10$^{11}$ pGL3/AFP pBS/mIL-12 pTGC3001 pTGC3011 pTGC3013 pTGC3014

ADENOVIRUS/ALPHAVIRUS HYBRID VECTOR FOR THE EFFECTIVE ADMINISTRATION AND EXPRESSION OF THERAPEUTIC GENES IN TUMOUR CELLS

CROSS-REFERENCE TO RELATED APPLICATIONS

This application is filed under the provisions of 35 U.S.C. §371 and claims the priority of International Patent Application No. PCT/ES2005/000277 filed on 18 May 2005, which in turn claims priority of Application No. P200401219 (España) filed on 20 May 2004.

TECHNICAL FIELD OF THE INVENTION

The present invention refers to genic expression vectors derived from adenoviruses, for the obtainment of therapeutic products.

STATE OF THE ART PRIOR TO THE INVENTION

One of the principal problems facing conventional cancer therapy is the lack of tumor specificity, a situation that often leads to serious side effects and limits the applicable therapeutic dose. Although gene therapy remains highly promising for cancer treatment, it also faces a specific problem: targeting transgenic expression to the tumor site. A number of studies suggest that when viral vectors are administered on an intralesional basis, although transgenic expression is essentially confined to a region adjacent to the needle trajectory, though such expression may also occur in other tissues. Consequently, an important objective in gene therapy applied to cancer is the targeting of therapeutic gene expression to the tumors via specific administration to the neoplastic tissue ("tissue objective") and/or specific activation ("transcriptional objective") within the neoplastic tissue, without affecting the healthy cells. The "tissue objective" can be achieved by creating a vector targeted via modifications of the receptor-ligand interactions, thus allowing the infection of cells that express a specific receptor. The "transcriptional objective" can be achieved using a tumor specific promoter to control transgenic expression. Previous studies have used different tumor specific promoters. However, these present an essential limitation in that they do not yield high levels of genic expression, as a result of which the antitumoral activity is limited.

A review of the latest advances in the development of viral vectors for gene therapy can be found in Lundstrom K. "Latest development in viral vectors for gene therapy"; *Trends in Biotechnology,* 2003, 21:118-122.

Currently used viral vectors include the alphaviruses. Alphaviruses are enveloped viruses that contain a simple positive RNA strand as genome. Expression vectors derived from the alphaviruses Sindbis Virus (SIN), Semliki Forest Virus (SFV), and Venezuelan equine encephalitis (VEE) virus have been designed and developed. The alphavirus vectors are based on the use of self-replicating RNA molecules derived from alphaviral genomes in which the 5' and 3' sequences necessary for replication and the replicase (Rep) gene have been maintained, while the genes encoding for the viral structural proteins have been deleted and replaced with a transgene. Following cell transfection of these vectors, Rep is translated and the RNA vector is copied in a negative RNA strand, which will be used as a template for amplification of the RNA vector. Rep can also recognize a subgenomic promoter in the negative RNA strand, from which a smaller subgenomic RNA segment is in turn synthesized that can be translated to produce important levels of heterologous proteins. Alphaviral vectors can be used directly as RNA when transcribed in vitro from a prokaryotic promoter such as SP6 or T7, or as DNA when the replicon sequence is located under an eukaryotic promoter such as CMV. The RNA vector can be packaged in viral particles via its cotransfection in cells, together with one or more "helper" RNAs that encode for the viral structural proteins. Alphaviral vectors possess a series of properties that make them attractive for gene therapy: a very extensive tropism, low immunogenicity, and a high level of heterologous protein expression. Such expression is, however, transient due to the induction of apoptosis in the cells when replication takes place. The document Rayner J. O., Dryga S. A., Kamrud K. I. "Alphavirus vectors and vaccination"; *Rev. Med. Virol.* 2002; 12 279-296, describes the development of expression vectors based on alphaviruses for use in the field of vaccines.

Another series of viral vectors are based on adenoviruses. There is extensive literature on the use of adenoviruses, which have been developed to overcome some of the inconveniences of gene therapy, and as a source for the creation of expression vectors. A document reporting the latest advances in the field of adenoviral vectors has been published by Volpers C, Kochanek S. "Adenoviral vectors for gene transfer and therapy"; *J Gene. Med.* 2004; 6: 5164-5171. Adenoviruses have the advantage of affording high transduction efficiency and the capacity to persist in episomal form. However, the expression of adenoviral proteins induces potent immune responses that limit the duration of transgenic expression and induce toxicity in the cells infected with the vector. Gutless adenoviruses have been developed to solve these problems. These gutless adenoviruses have been deprived of all the corresponding adenoviral genes (the only sequences preserved being the two inverted terminal repeat sequences and the packaging signals), consequently, the transduced cells express no adenoviral product and do not induce an immune response to the vector. In short, the elimination of all the adenoviral genes leaves sufficient space to house large expression cassettes and that is why gutless adenoviruses are also called high-capacity adenoviral vectors. A document describing concrete aspects of adenoviral vectors, related to the deletion of all the sequences encoding for viral proteins, has been published by Morsy MA et al. "An adenoviral vector deleted for all viral coding sequences results in enhanced safety and extended expression of a leptin transgene"; *Proc. Natl. Acad. Sci. USA* 1998, 95:7866-7871. The document published by Schiedner G et al. "Variables affecting in vivo performance of high-capacity adenovirus vectors"; *J. Virol.* 2002, 76:1600-1609 describes the use of stuffer DNA in expression vectors based on gutless adenoviruses, showing that the presence of such stuffer DNA is essential for achieving a considerable increase in genic expression, and that, in general, the designing of vectors based on high-capacity (gutless) adenovirus can substantially modify the degree and duration of expression of a gene.

On the other hand, document U.S. Pat. No. 5,981,225 describes a vector for gene transfer based on adenoviruses that comprises inverted terminal repeat (ITR) sequences, at least one packaging signal sequence, and a VAI adenoviral gene and/or VAII adenoviral gene; and comprises a gene foreign to the adenovirus operatively bound to a functional promoter in target cells for adenovirus.

The document U.S. Pat. No. 5,985,846 describes a gene transfer vector comprising inverted terminal repeat (ITR)

sequences of adenovirus and recombinant particles of adenovirus containing these sequences.

The document U.S. Pat. No. 6,566,093 describes vectors of cDNA derived from alphaviruses that consist of DNA complementary to at least part of the RNA of an alphavirus, essential for replication of the alphavirus, and heterologous cDNA, for example, cDNA encoding for a desired substance. The latter can be a biologically active protein or polypeptide, as well as an immunogenic or antigenic protein or polypeptide, a therapeutically active protein or polypeptide, or a therapeutically active RNA.

The purpose of the present invention is to improve transgenic expression and the induction of apoptosis in tumor cells mediated by hybrid vectors in vitro and in vivo. An additional objective is to improve the efficiency of tumor therapy in animal models by means of hybrid vectors.

An additional objective is also to develop a method of gene therapy, in particular for the treatment of cancer, by means of the use of hybrid vectors.

The objectives of the present invention are achieved by combining the following in a single vector:

high infective capacity, by using an adenovirus release system, high transgenic expression and the induction of apoptosis by using a vector derived from an alphavirus, such as SFV, and tumor specificity by using a tumor specific promoter.

DESCRIPTION OF THE INVENTION

The present invention firstly relates to a genic expression adenoviral hybrid vector characterized in that it comprises at least the following elements, oriented in the direction 5' to 3':
  i. a first chain of adenoviral origin comprising a first inverted terminal repeat (ITR) sequence and a signal sequence for packaging of the adenovirus;
  ii. a first non-encoding stuffer sequence;
  iii. a sequence corresponding to a tissue specific promoter;
  iv. a chain of cDNA derived from an alphavirus, the sequence of which is partly complementary to an alphaviral RNA, comprising at least a sequence encoding for at least one exogenous gene of interest;
  v. a polyadenylation sequence; and
  vi. a second adenoviral inverted terminal repeat (ITR) sequence.

More specifically, the present invention relates to the construction of an adenoviral hybrid vector comprising as element iv a chain of cDNA derived from an alphavirus corresponding to the sequence of an SFV recombinant replicon, under the transcriptional control of a tumor specific promoter (element iii), which is the promoter of alpha-fetoprotein (AFP). In this construct, a transgene can be inserted in the SFV replicon, directed by the subgenomic promoter of SFV. Following infection of the tumor cells with this hybrid vector, the mRNA of the SFV replicon is transcribed from the tumor specific promoter, and the non-structural proteins—nsPs—which constitute the SFV replicase gene are translated from said mRNA of the SFV replicon. These nsPs proteins—viral replicase—initiate replication of the mRNA of the SFV replicon, to generate the subgenomic RNA of SFV. Consequently, the transgene can be expressed at a high level from the subgenomic RNA of SFV. This global viral replication process will give rise to the production of apoptosis in the infected cells. In the event that these hybrid infect non-tumor cells, the mRNA of the SFV replicon will not be transcribed from the tumor specific promoter, which will not be active in these cells. Thus, there will be no expression of the transgene, and apoptosis will not occur in normal cells infected with the hybrid vector.

The present invention further relates to a method for obtaining said adenoviral hybrid vector, comprising the assembly of elements i. to vi. of the adenoviral hybrid vector defined above by means of genetic engineering techniques.

The present invention also relates to the use of the mentioned vector hybrid for transferring genetic material to a cell, and more particularly for introducing and expressing foreign genes in eukaryotic cells that may be target cells for adenovirus.

The transfer of genetic material preferably results in the induction of an immune response against foreign antigens in said cell.

The present invention also relates to a pharmaceutical composition comprising said adenovirus-alphavirus hybrid vector and its use in the therapeutic treatment of cancer, comprising the administration of said pharmaceutical composition to a subject.

The present invention also relates to a method for cancer treatment by means of the use of the previously defined hybrid vector, comprising the administration of said hybrid vector to a subject.

The present invention relates to a genic expression adenoviral hybrid vector characterized in that it comprises at least the following elements, oriented in the direction 5' to 3':
  i. a first chain of adenoviral origin comprising a first inverted terminal repeat (ITR) sequence and a signal sequence for packaging of the adenovirus;
  ii. a first non-encoding stuffer sequence;
  iii. a sequence corresponding to a tissue specific promoter;
  iv. a chain of cDNA derived from an alphavirus, the sequence of which is partly complementary to an alphaviral RNA sequence, comprising at least a sequence encoding for at least one exogenous gene of interest;
  v. a polyadenylation sequence; and
  vi. a second adenoviral inverted terminal repeat (ITR) sequence.

The nature of element i. in the alphavirus-adenovirus hybrid vector of the present invention, i.e., the nature of the chain of adenoviral origin comprising a first inverted terminal repeat (ITR) sequence and a signal sequence for packaging ($\psi$) of the adenovirus, is not a critical aspect for the present invention, and may originate from any adenovirus serotype. Said serotypes are well known in the technique and include for example Ad12 (subgenus A), Ad3 and Ad7 (subgenus B), Ad2 and Ad5 (subgenus C), Ad8 (subgenus D), Ad4 (subgenus E), Ad40 (subgenus F), and other known non-human adenoviruses that may originate from species such as pigs, sheep, cows and birds. Therefore, this first inverted terminal repeat sequence which may contain approximately between 100 and 500 bp in length, can vary according to the adenovirus serotype used. In the same way, the signal sequence for packaging of the adenovirus can vary according to the adenovirus serotype employed.

According to a preferred particular embodiment, said genic expression adenoviral vector comprises an element i. having SEQ ID No 1, or any other sequence having sufficient homology with SEQ ID No 1 for performing the same function.

The nature of element ii. in the adenoviral hybrid vector of the present invention is not a critical aspect of the same. Said element ii., the function of which is to increase the total size of the construct, can be any non-encoding stuffer sequence. Said sequence is preferably a human non-encoding sequence.

Even more preferably, this non-encoding stuffer sequence is the intron region of human genomic hypoxanthine phosphoribosyltransferase (HPRT).

Preferably, the defined adenoviral hybrid vector also comprises an element vii., which is a second non-encoding stuffer sequence, located between element v. and element vi. defined above.

The nature of element iii. in the adenoviral hybrid vector of the present invention is not a critical aspect thereof. The tissue specific promoter iii. is preferably a tumor specific promoter. Examples of tumor specific promoters include the promoters AFP, telomerase TERT, PAP (pancreatic associated protein), E2F and HIF.

According to a preferred particular embodiment of the invention, the tumor specific promoter has the sequence SEQ ID No 7 corresponding to the AFP promoter/enhancer, (AFP p+e), or the sequence SEQ ID No 15 corresponding to telomerase TERT, or any other sequence having sufficient homology with the sequence SEQ ID No 7 or with the sequence SEQ ID No 15, for performing the same function, respectively.

The nature of element iv. in the adenoviral hybrid vector of the present invention is not a critical aspect thereof. The alphaviral sequences of element iv. are preferably derived from the Semliki Forest Virus (SFV). However, it would be possible to use other alphaviral sequences derived from any of the species belonging to the Togaviridae family, for example SIN, RRV and VEE.

Said chain iv. of cDNA derived from an alphavirus, the sequence of which is partly complementary to alphaviral RNA, preferably comprises (in addition to a sequence encoding for at least one exogenous gene of interest):

a) a 5' sequence necessary for replication of the alphavirus,
b) a sequence encoding for the non-structural proteins required for replication of the alphaviral RNA,
c) at least one subgenomic promoter of the alphavirus, and
d) a 3' sequence necessary for replication of the alphavirus;

Element iv. preferably forms a replicon functionally controlled by the promoter iii., and where in turn the alphaviral subgenomic promoter comprised in iv. c) functionally controls the expression of the exogenous gene of interest.

According to a preferred particular embodiment, the sequences a) to c) of element iv. as a whole have a sequence selected from SEQ ID No 3 (SFV 5'-rep-Psg) or any other sequence having sufficient homology with SEQ ID No 3 for performing the same function, and SEQ ID No 4 (SFV 5'-rep-Psg-enh) or any other sequence having sufficient homology with SEQ ID No 4 for performing the same function.

According to an especially preferred particular embodiment, element iv. d) has the sequence SEQ ID No 5 (SFV3'), or any other sequence having sufficient homology with SEQ ID No 5 for performing the same function.

In element iv. of the alphavirus-adenovirus hybrid vector of the present invention, the exogenous gene of interest is preferably a therapeutic gene or a reporter gene, or a combination of both. Without being considered as limiting, the therapeutic gene is preferably selected from mammalian interleukin IL-12, colony stimulating factor GMCSF, alpha-interferon, and herpes simplex virus thymidine kinase (tk).

The exogenous gene of interest in element iv. may further be a reporter gene. Without being considered as limiting, the reporter gene can be selected from LacZ, Luciferase, tk and GFP.

The therapeutic gene is especially preferably mammalian interleukin IL-12, and even more preferably the therapeutic gene is human interleukin, hIL-12.

The genic expression adenoviral hybrid vector can include in element iv in series one or several subsets of (subgenomic promoter+exogenous gene of interest).

The nature of element v. in the adenoviral hybrid vector of the present invention is not a critical aspect thereof. Element v. is preferably a polyadenylation sequence of SV40. Said polyadenylation sequence of SV40 is especially preferable sequence SEQ ID No 6, or any other sequence having sufficient homology with sequence SEQ ID No 6 for performing the same function.

The nature of element vi. in the adenoviral hybrid vector of the present invention, is not a critical aspect thereof. According to a preferred embodiment, said genic expression adenoviral vector comprises an inverted terminal repeat (ITR) sequence as element vi., which has sequence SEQ ID No 2, or any other sequence having sufficient homology with SEQ ID No 2 for being able to perform the same function.

The nature of element vii. in the adenoviral hybrid vector of the present invention is not a critical aspect thereof. The second non-encoding stuffer sequence can be any such sequence. It is preferably a human non-encoding sequence, and especially preferably a sequence from human cosmid C346.

The genic expression adenoviral hybrid vector of the present invention can have a variable length, and preferably has a length comprised between 27 and 38 kilobases.

According to a preferred particular embodiment, the adenoviral hybrid vector comprises ITR 5' as a first inverted terminal repeat sequence; HPRT, the intron region of human genomic hypoxanthine phosphoribosyltransferase as a first stuffer sequence; AFP (p+e), a tumor specific promoter; an SFV replicon sequence containing mIL-12, interleukin-12 from mice; SV40 PolyA, a polyadenylation sequence of SV40; C346, human genomic cosmid C346 as a second stuffer sequence, and ITR 3' as a second inverted terminal repeat sequence.

According to an additional preferred particular embodiment, the adenoviral hybrid vector comprises ITR 5' as a first inverted terminal repeat sequence; HPRT, the intron region of human genomic hypoxanthine phosphoribosyltransferase as a first stuffer sequence; AFP (p+e), a tumor specific promoter; an SFV replicon sequence containing LacZ; SV40 PolyA, a polyadenylation sequence of SV40; C346, human genomic cosmid C346 as a second stuffer sequence, and ITR 3 as a second inverted terminal repeat sequence.

According to a particularly preferred additional embodiment, the adenoviral hybrid vector comprises ITR 5' as a first inverted terminal repeat sequence; HPRT, the intron region of human genomic hypoxanthine phosphoribosyltransferase as a first stuffer sequence; AFP (p+e), a tumor specific promoter; an SFV replicon sequence containing hIL-12, human interleukin-12; SV40 PolyA, a polyadenylation sequence of SV40; C346, human genomic cosmid C346 as a second stuffer sequence, and ITR 3' as a second inverted terminal repeat sequence.

According to a preferred particular embodiment of the present invention, the genic expression adenoviral hybrid vector has sequence SEQ ID No 8, or any other sequence having sufficient homology with SEQ ID No 8 for performing the same function.

According to an additional preferred particular embodiment of the present invention, the genic expression adenoviral hybrid vector has sequence SEQ ID No 9, or any other sequence having sufficient homology with SEQ ID No 9 for performing the same function.

According to an additional preferred particular embodiment of the present invention, the genic expression adenoviral hybrid vector has sequence SEQ ID No 10, or any other sequence having sufficient homology with SEQ ID No 10 for performing the same function.

The present invention further relates to a method for obtaining said adenoviral hybrid vector, comprising the assembly of elements i. to vi., or i. to vii., of the adenoviral hybrid vector defined above by means of genetic engineering techniques.

The present invention also relates to the use of said hybrid vector for transferring genetic material to a cell, and more particularly for introducing and expressing foreign genes in eukaryotic cells that may be target cells for adenoviruses. Said use comprises administering said hybrid vector to a subject.

The infection of tumor cells with an adenoviral hybrid vector according to the invention, results in the transcription of the mRNA of the SFV alphavirus replicon from the tumor specific promoter, therefore the Rep gene will be translated and the RNA of SFV will be amplified. Rep also produces a subgenomic RNA of SFV, from which the therapeutic or reporter gene will be expressed at high levels. The product of the therapeutic gene secreted by the infected cells will activate the immunocytes at the infection site. The replication of SFV will further induce apoptosis of the infected cells, leading to the release of tumor antigens from the apoptotic cells; which can be captured by antigen-presenting cells (APCs), thereby activating the immune response against the tumor. However, if this hybrid vector infects non-tumor cells, the mRNA of the SFV replicon will not be transcribed, and therefore no transgenic expression or apoptosis will occur.

The tumor cells are preferably infected with an adenoviral hybrid vector according to the invention, such that the mRNA of the SFV replicon is transcribed from the tumor specific promoter AFP, therefore the Rep gene will be translated and the RNA of SFV will be amplified. Rep will also produce a subgenomic RNA of SFV, from which mIL-12 or hIL-12 will be expressed at high levels. mIL-12 or hIL-12 secreted by infected cells will activate immunocytes at the infection site. The replication of SFV will further induce apoptosis in the infected cells, leading to the release of tumor antigens by the apoptotic cells, which can be captured by antigen-presenting cells (APCs), thereby activating the immune response against the tumor. However, if this hybrid vector infects non-tumor cells, the mRNA of the SFV replicon will not be transcribed, and therefore no transgenic expression or apoptosis will occur.

An additional objective of the present invention is the use of an adenoviral hybrid vector defined previously in a process for transferring genetic material to a cell, preferably a tumor cell, and which comprises administering said hybrid vector to a subject. Even more preferably, said cell is a tumor cell that expresses AFP.

An additional objective of the present invention is the use of a defined adenoviral hybrid vector for the preparation of an effective medicament in the treatment of tumors, and its use for inducing an immune response against foreign antigens. Said use comprises administering said medicament to a subject.

An additional objective of the present invention is a pharmaceutical composition comprising at least an adenoviral hybrid vector defined according to the present invention, and the use thereof in a process for the treatment of tumors, or for inducing an immune response to foreign antigens.

Said pharmaceutical composition preferably comprises an adenoviral hybrid vector according to the present invention, in which the exogenous gene of interest is the mammalian interleukin, IL-12, preferably human interleukin hIL-12. Said use comprises administering the pharmaceutical composition comprising said hybrid vector to a subject.

The present invention also relates to a method for the treatment of cancer by means of the use of the hybrid vector according to the present invention, said method comprising the administration of said hybrid vector to a subject.

Therefore, according to preferred embodiments of the present invention, AFP (p+e) has been selected as a tumor specific promoter, two adenoviral hybrid vectors have been constructed in which the SFV replicon is controlled by the AFP promoter, and the reporter gene LacZ and the therapeutic gene IL-12 are inserted under the control of the SFV subgenomic promoter, respectively—Ad/AFP-SFV-LacZ and Ad/AFP-SFV-mIL-12; and two gutless adenoviral vectors carrying Lacz and IL-12 from mice directly controlled by the AFP promoter—Ad/AFP-LacZ and Ad/AFP-mIL-12—have been prepared as control vectors. It has been shown that the hybrid vector of the present invention works more effectively than the control vectors used to date.

According to the present invention, it has been shown that the vector Ad/AFP-SFV-mIL-12 can be a useful vector in the therapy of HCC (hepatocarcinoma) tumors expressing AFP.

It has also been shown that the use of other tumor promoters such as telomerase promoter, TERT, which is widely activated in most malignant tumors for controlling SFV can convert the use of a hybrid vector such as that of the present invention into a general strategy for the treatment of all types of cancer.

Furthermore and advantageously, the hybrid vector of the present invention specifically works with tumor cells and destroys tumor cells without the need to incorporate a therapeutic gene. Additionally, it is shown that the hybrid vector of the present invention advantageously induces a potent anti-tumor activity when it includes a therapeutic gene such as IL-12.

BRIEF DESCRIPTION OF THE FIGURES

FIG. 1 (B) shows the anti-tumor activity of the hybrid vector according to the invention: following infection of the HCC tumor cells with this hybrid vector (right), thanks to the presence in the hybrid vector of the SFV replicon comprising mIL-12, high-level expression of mIL-12 occurs, which will activate the immunocytes at the infection site. The replication of SFV will further induce apoptosis of the infected cells. However, if this hybrid vector infects non-tumor cells, the mRNA of the SFV replicon will not be transcribed, and consequently there will be no transgenic expression or apoptosis. In this Figure:

ITR, adenoviral inverted terminal repeat sequences;
ψ, adenoviral packaging signal;
HPRT and C346, sequences of stuffer DNA from the intron region of human genomic hypoxanthine phosphoribosyltransferase or from the human cosmid C346, respectively;
PolyA, polyadenylation signal (for example, of SV40);
APCs, antigen-presenting cells.

Figure 1:
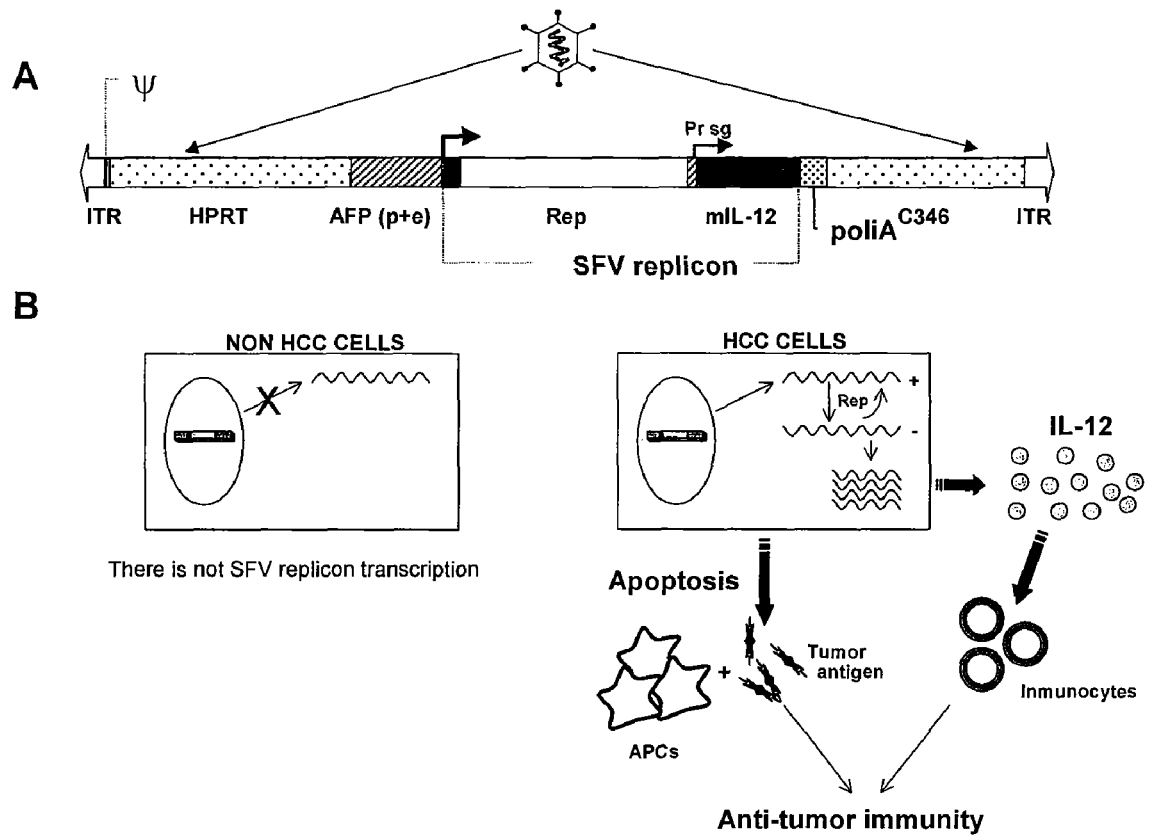
FIG. 1 (A): shows the diagram of a hybrid vector according to an embodiment of the invention, Ad-SFV, containing a gutless adenovirus sequence in which an SFV replicon has been inserted under the control of the AFP promoter/enhancer (AFP (p+e)), and containing the heterologous mIL-12 gene, which is placed under the control of the SFV subgenomic promoter (Pr sg).
Figure 2:
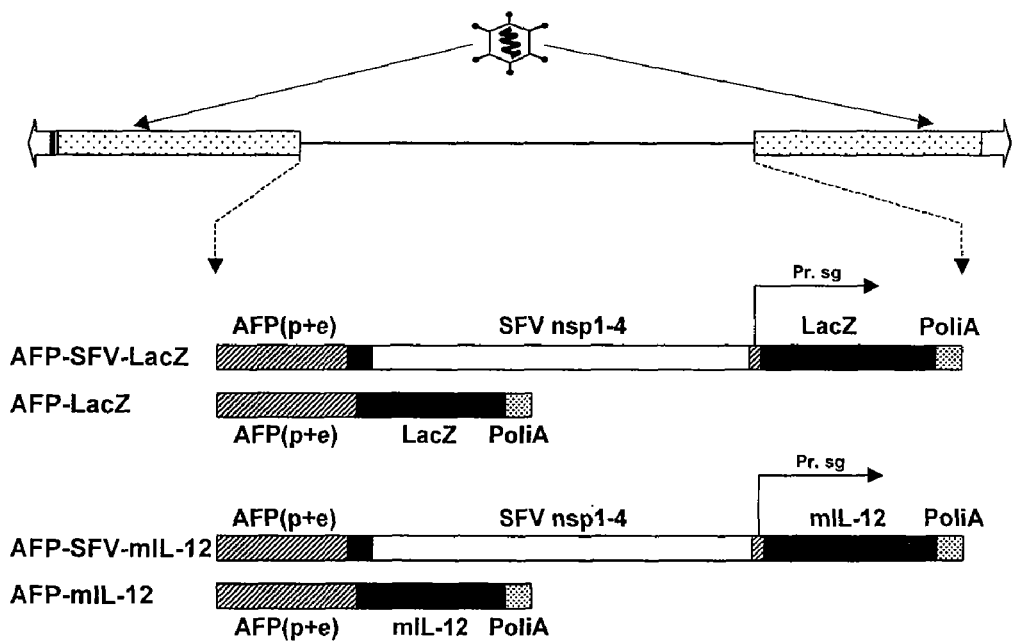

FIG. 2 shows the structure of the gutless adenoviral hybrid vectors and gutless adenoviral vectors. AFP-SFV-LacZ and AFP-SFV-mIL-12 are hybrid adenovirus vectors, in which the SFV replicon sequence is under the control of the AFP promoter/enhancer (AFP(p+e)), and the heterologous genes LacZ or mIL-12 have been cloned under the control of the SFV subgenomic promoter (Pr sg), respectively. AFP-lacZ and AFP-mIL-12 are adenoviral vectors containing LacZ or mIL-12 directly controlled by AFP (p+e). SFV nsp1-4, non-structural proteins of SFV.

FIG. 3 shows the specific expression of mIL-12 in vitro in hepatocarcinoma cells expressing AFP, HCC (A), and in cells not derived from HCC (B) following infection with the hybrid vectors of Ad-SFV: AFP-mIL-12 (AFP-12), AFP-SFV-mIL-12 (AFP-SFV-12), or with the control vector AdCMVmIL-12 (CMV-12). Different multiplicities of infection "moi" were tested (10, 100 and 1000). Hep3B, Huh-7, HepG2 and PLC/PRF/5: HCC cell lines; Hela, A549, MHC1, SK-Hep-1 and Clon 9: lines not derived from HCC. FIG. 3B only shows the expression corresponding to moi 1000.

Figure 4:
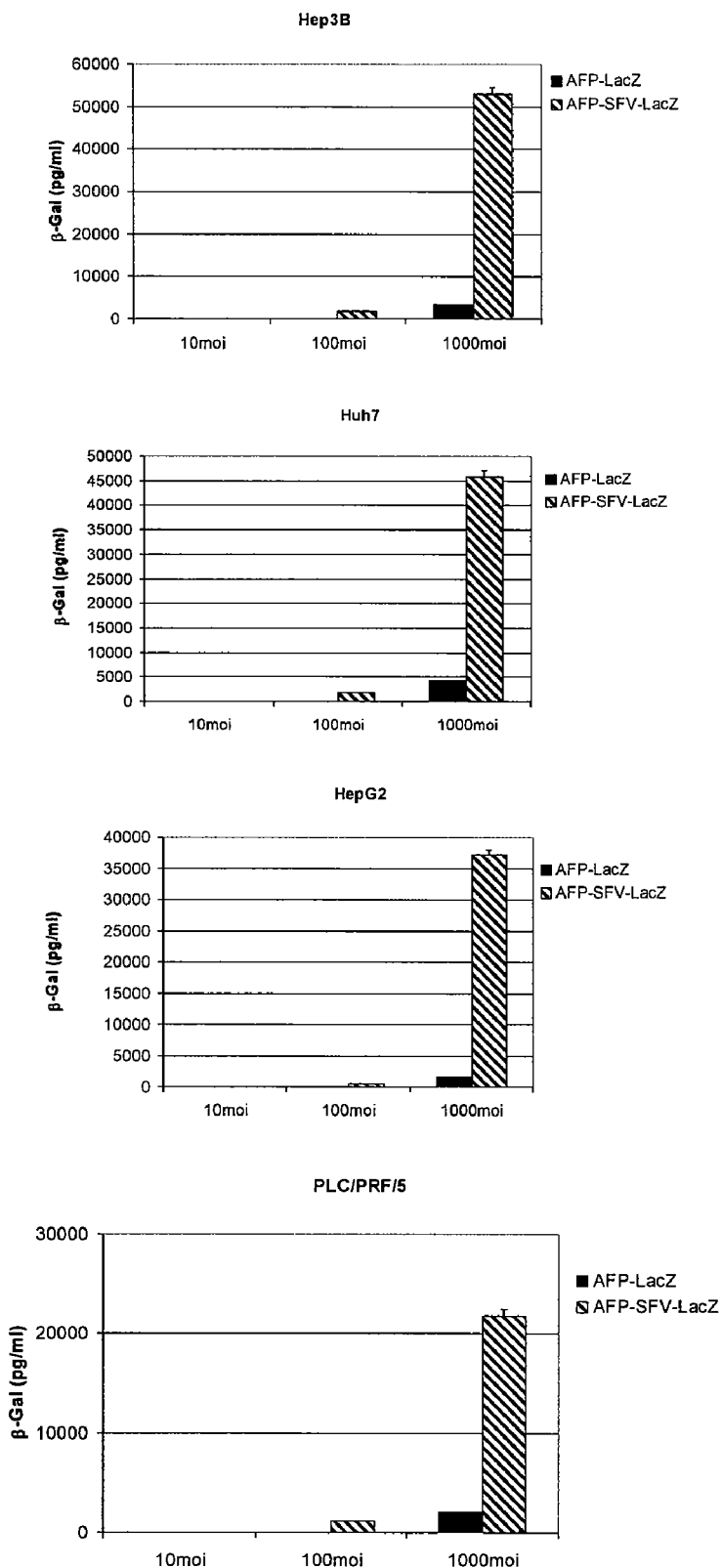

FIG. 4 shows the specific expression of β-gal in 4 HCC cell lines (Hep3B, Huh-7, HepG2 and PLC/PRF/5) following in vitro infection with the hybrid vector AFP-SFV-lacZ or with the control vector AFP-LacZ at different "moi" (10, 100, or 1000).

Figure 5:
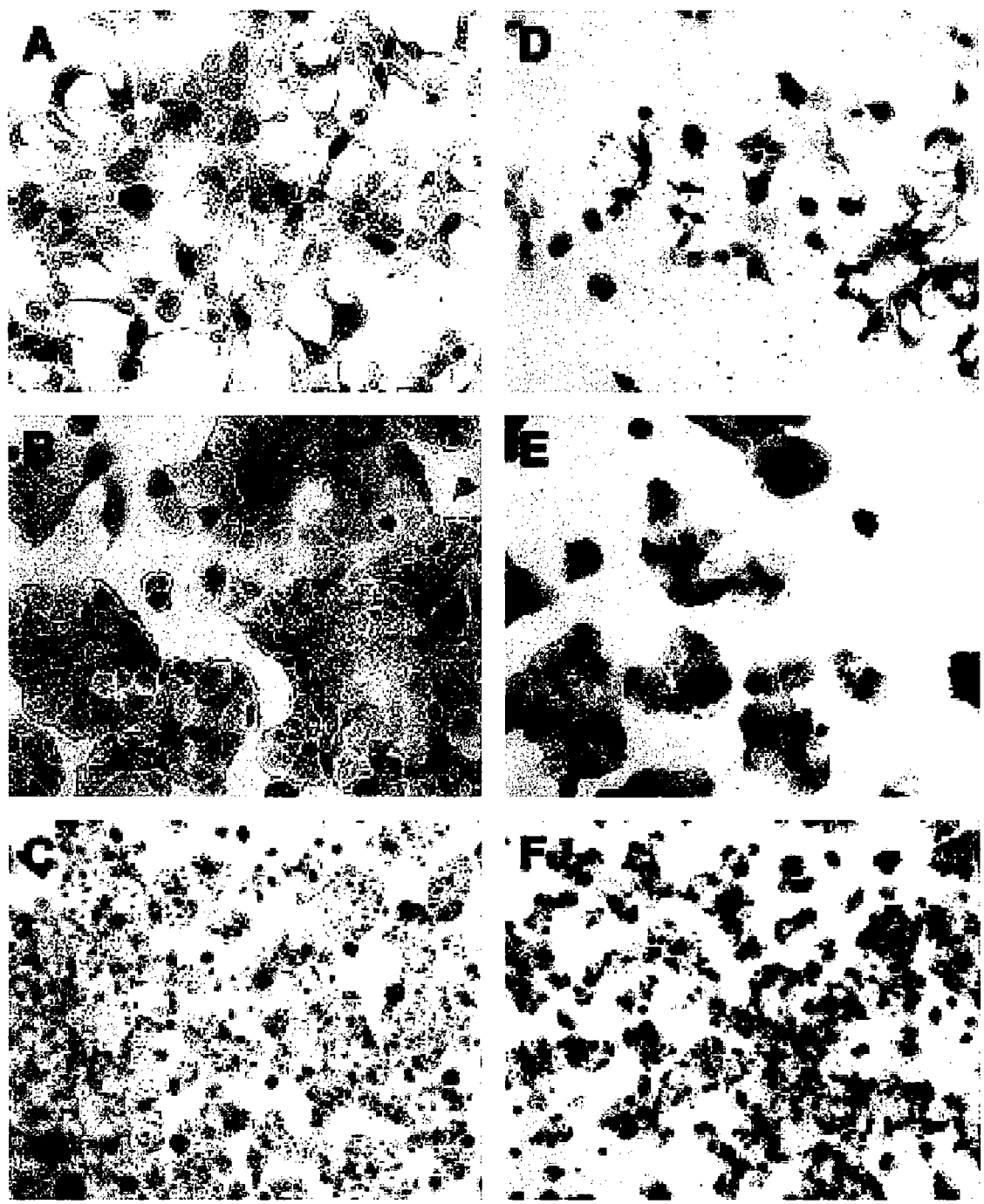

FIG. 5 shows the analysis of the expression of β-gal in HCC cell lines infected with AFP-LacZ and AFP-SFV-LacZ. Microphotographs of cells infected with AFP-LacZ (A-C) or AFP-SFV-LacZ (D-F) and stained with X-Gal. A and D, Hep3B; B and E, Huh7; C and F, HepG2.

Figure 6A:
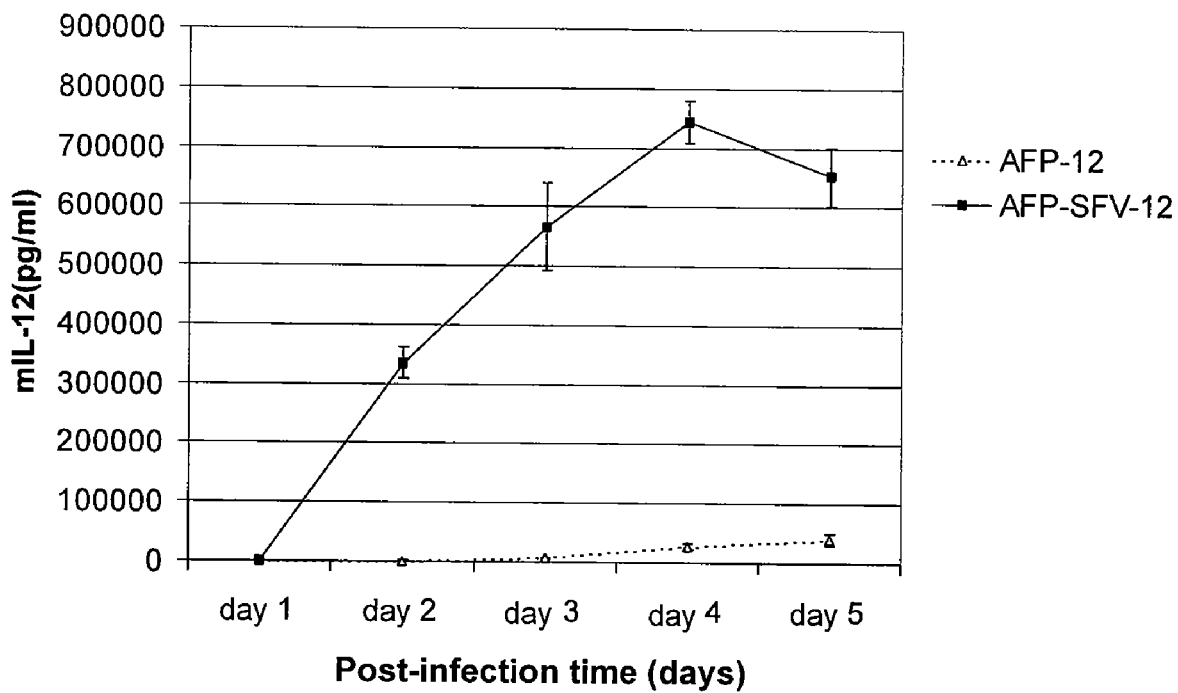
Figure 6B:
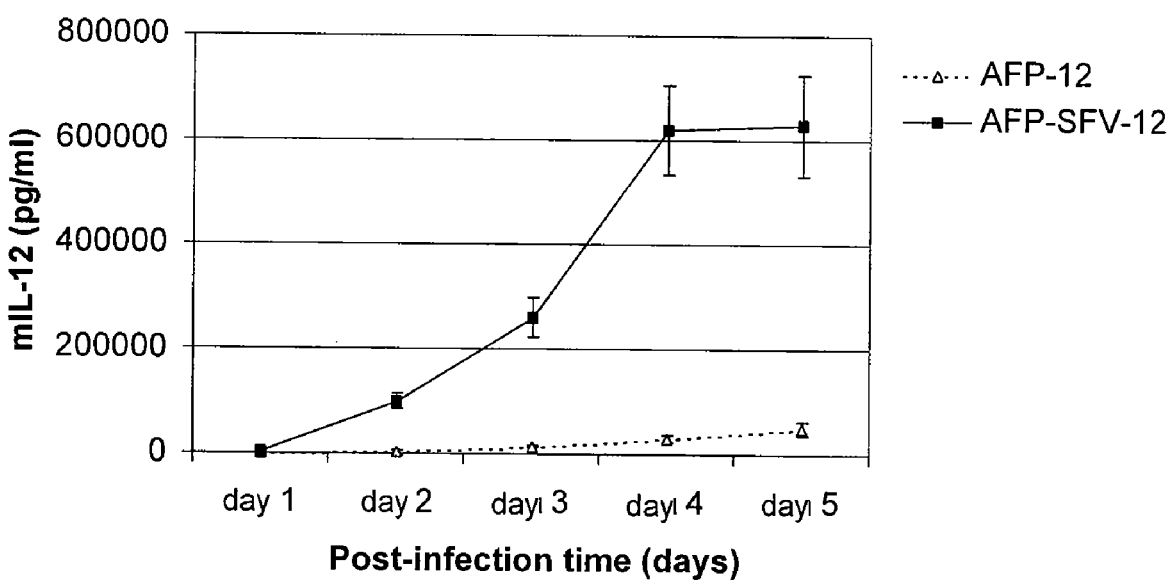

FIG. 6 shows the expression kinetics of IL-12 in HCC cell lines Hep3B (A) and Huh-7 (B), infected in vitro with adenoviral vectors AFP-mIL-12 (AFP-12) or AFP-SFV-mIL-12 (AFP-SFV-12), at a "moi" of 1000.

Figure 7A:
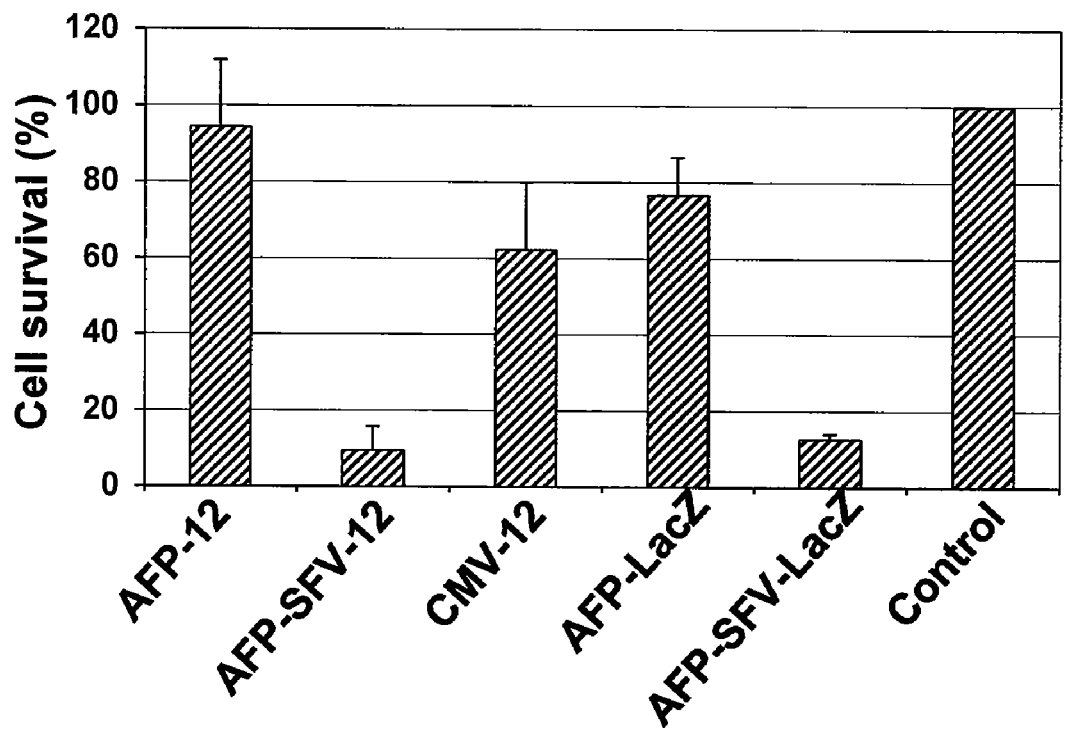
Figure 7B:
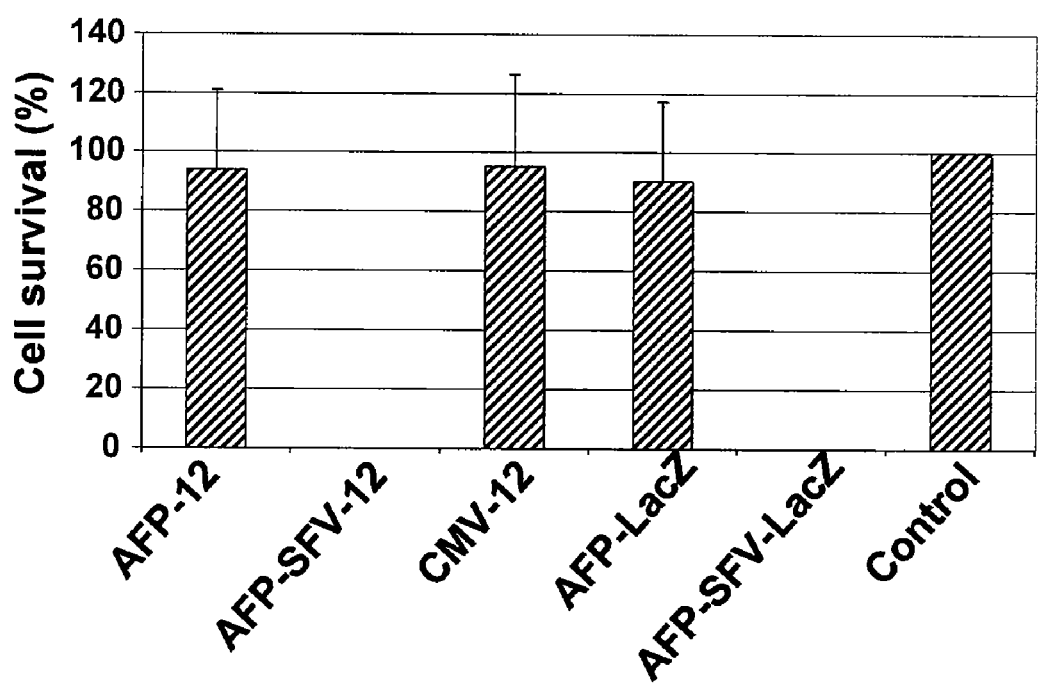

FIG. 7 shows the induction of cell death following the in vitro infection of HCC cell lines—Hep3B (A) and McA-RH7777 (B)—with vectors AFP-IL-12 (AFP-12), AFP-SFV-IL-12 (AFP-SFV-12), AFP-LacZ, AFP-SFV-LacZ, or control vector Ad/CMVmIL-12 (CMV-12). Cell survival is shown as the percentage of live cells in infected wells compared with the live cells in uninfected control wells.

Figure 8:
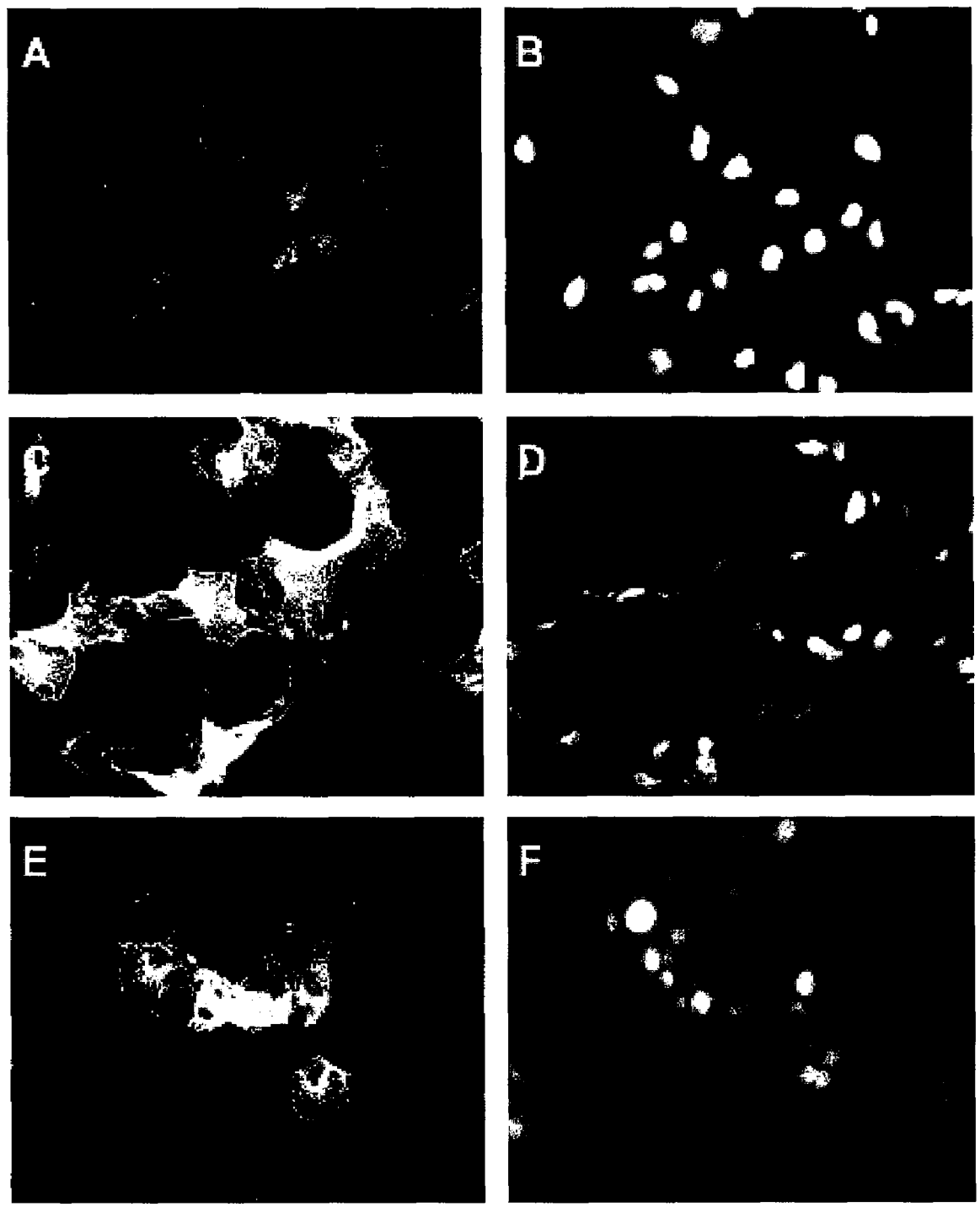

FIG. 8 shows the expression of SFV Rep in HCC cells—Hep3B (A-D) and Huh-7 (E and F)—following infection with vectors AFP-mIL-12 (A and B) or AFP-SFV-mIL-12 (C-F), at a "moi" of 1000. Two days after infection the cells were fixed and analyzed by immunofluorescence with a specific antibody for Rep. The cells expressing Rep were visualized under a fluorescence microscope with an FITC filter (A, C, and E), while the nuclei stained with DAPI in all cells were visualized with a UV filter (B, D, and F).

Figure 9:
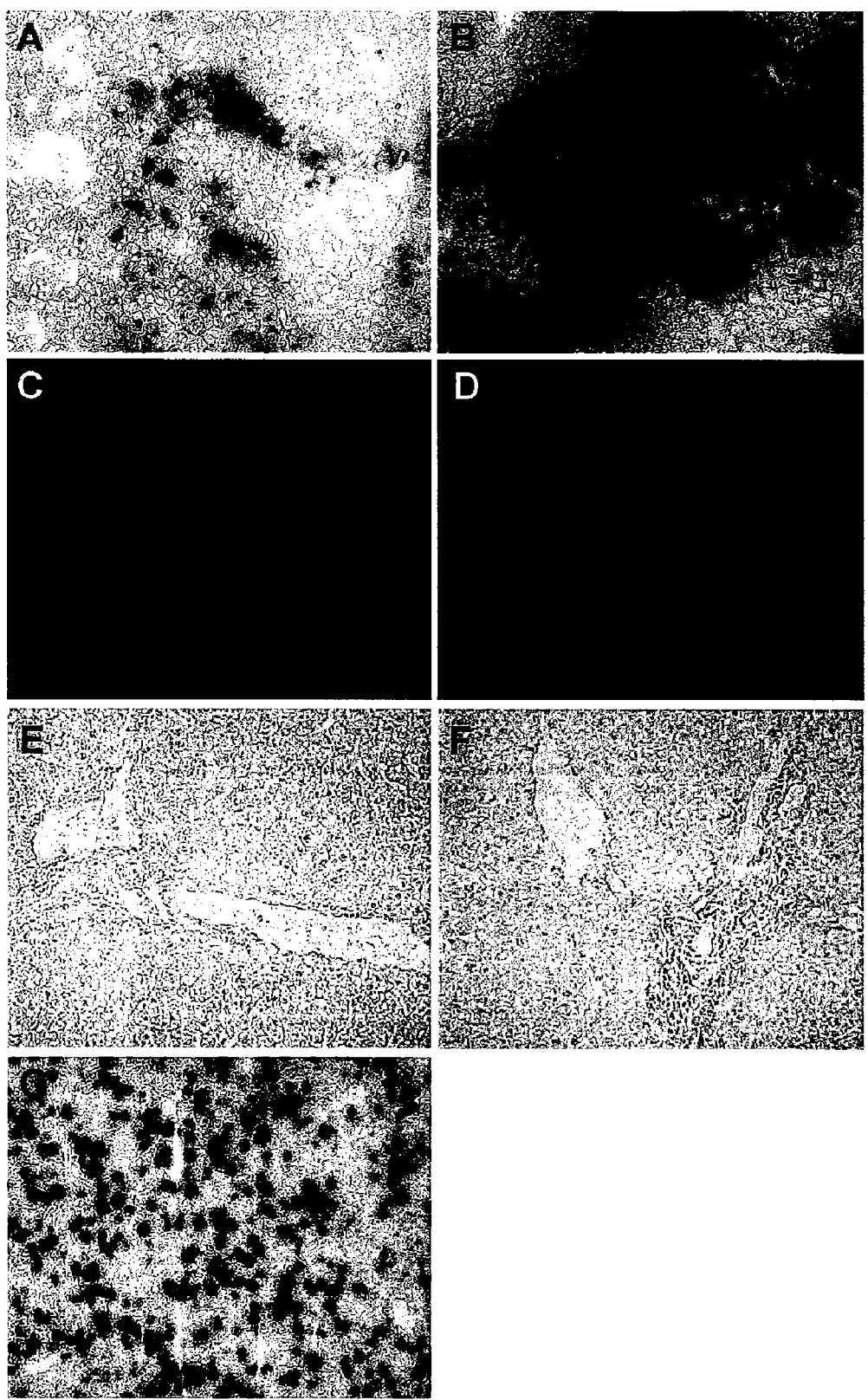

FIG. 9 shows the gene transfer with gutless hybrid vectors in vivo, (A-D), efficiency of the gene transfer and induction of apoptosis in Huh-7 tumors. Human Huh-7 tumors established in nude immunodeficient mice were treated via intratumor injection with the vectors AFP-LacZ (n=4) or AFP-SFV-LacZ (n=4), at $1\times10^{10}$ viral particles/animal. Three days after the administration of the virus, the mice were sacrificed and sections of the tumor were analyzed to study the transgene expression by staining with X-Gal (A-B) or to study the induction of apoptosis by means of TUNEL (C-D). A, C; Microphotographs or tumors that received AFP-LacZ. B, D. Microphotographs of tumors that received AFP-SFV-LacZ. (E-G), Specificity of the gene expression with gutless hybrid vectors. Healthy Balb/c mice were injected intravenously with $1\times10^{10}$ viral particles of the vectors AFP-LacZ (E), AFP-SFV-LacZ (F) or Ad/CMV-LacZ (G). Microphotographs of hepatic tissue sections taken three days after the inoculation and stained with X-Gal are shown.

FIG. 10 shows the treatment of HCC tumors with hybrid vectors. Orthotopic HCC tumors were established via the implantation of McH-RH7777 cells in rat liver. When the tumor reached a size of 7-10 mm in diameter, the animals were treated with $10^{11}$ (A-C) or with $2\times10^{11}$ (D-G) viral particles of AFP-mIL-12, AFP-SFV-mIL-12, or saline solution as control. The size of the tumor was measured on days 15 and 30 following the administration of saline solution (A and E), AFP-mIL-12 (B and F) or AFP-SFV-mIL-12 (C and G). G; Animal survival rate.

FIG. 11 shows the toxicity study in rats inoculated with vectors expressing IL-12. The level of transaminases (GPT, GOLT, and GGTL) (A) or of IL-12 (B) was determined in the serum of rats carrying HCC tumors in liver and which had been inoculated intratumorally with the adenovirus vectors AFP-SFV-IL-12, AFP-SFV-mIL-12, alphavirus vector SFV-IL-12, or with saline solution. The measurement was made on days 4 and 8 after the treatment.

Figure 12:
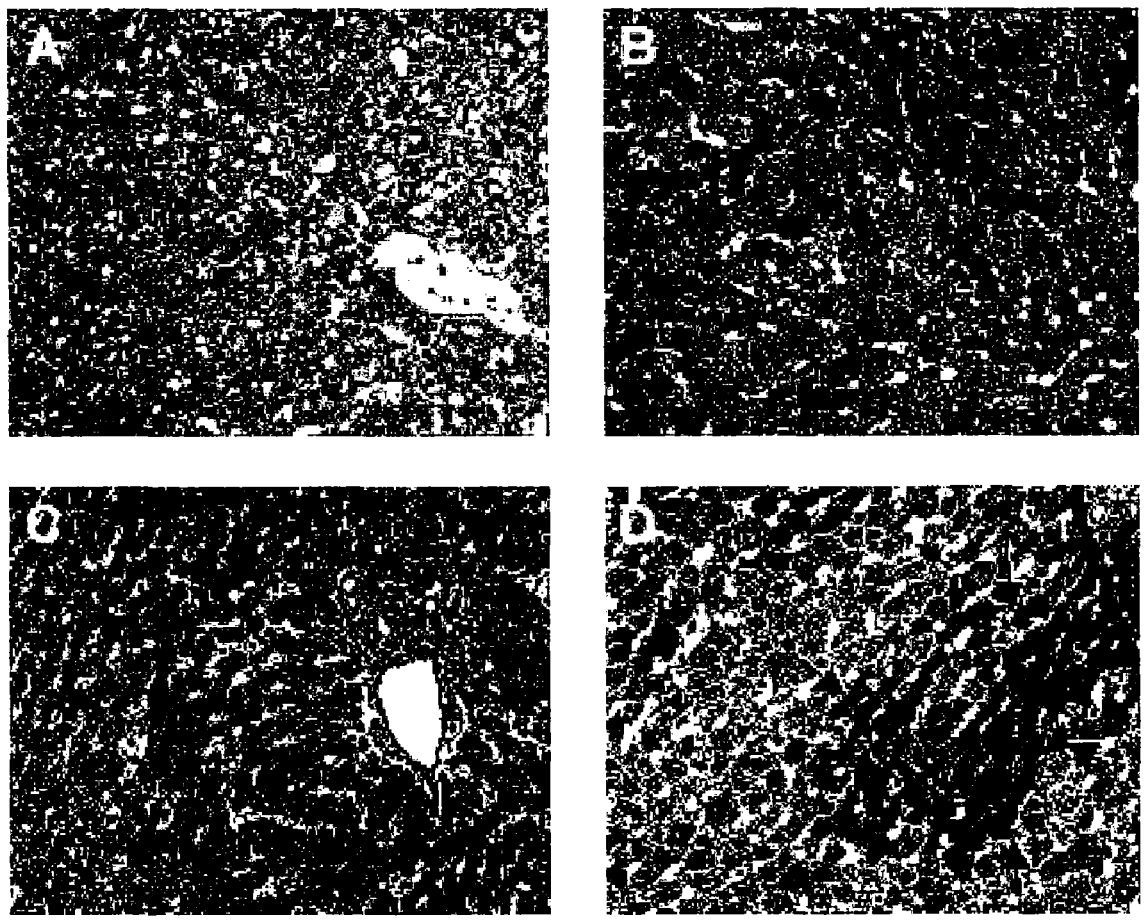

FIG. 12 shows the staining with hematoxylin/eosin of liver sections of rats treated with the adenoviral hybrid vectors. Rats carrying HCC tumors were treated via intratumor injection with saline solution (A), with the adenoviral vectors AFP-IL-12 (B), AFP-SFV-IL-12 (C), or with viral particles of SFV-IL-12 (D). Three days after the treatment the animals were sacrificed, the livers were removed and fixed with formol, and sections were obtained and stained with hematoxylin/eosin. The black arrows indicate areas with eosinophilic hepatocytes.

Figure 13A:
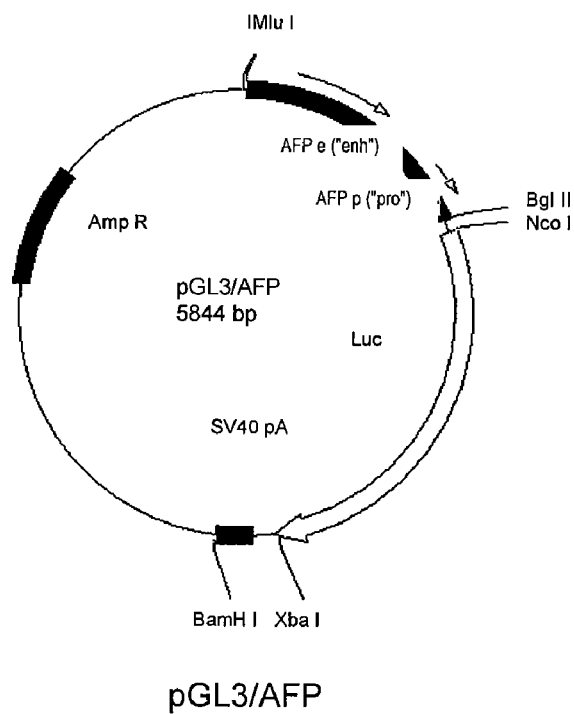
Figure 13B:
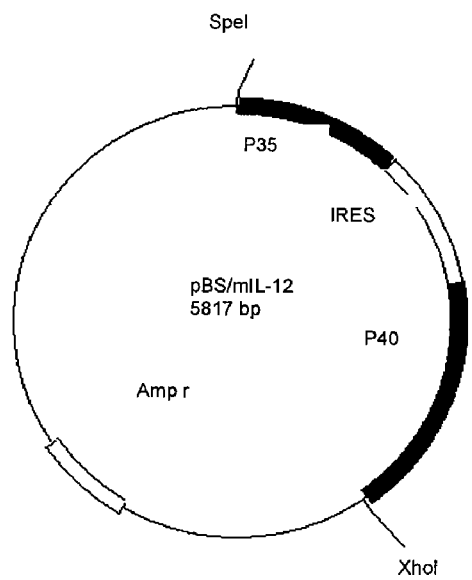

FIGS. 13A and 13B show restriction maps of plasmids pGL3/AFP and pBS/mIL-12, respectively.

Figure 14A:
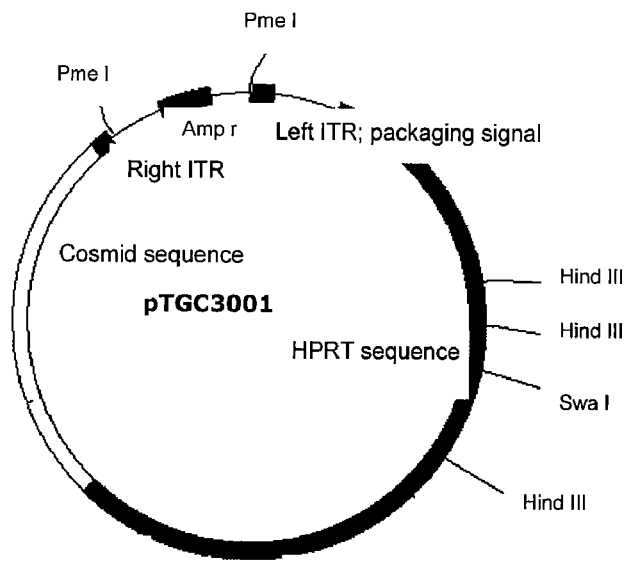
Figure 14B:
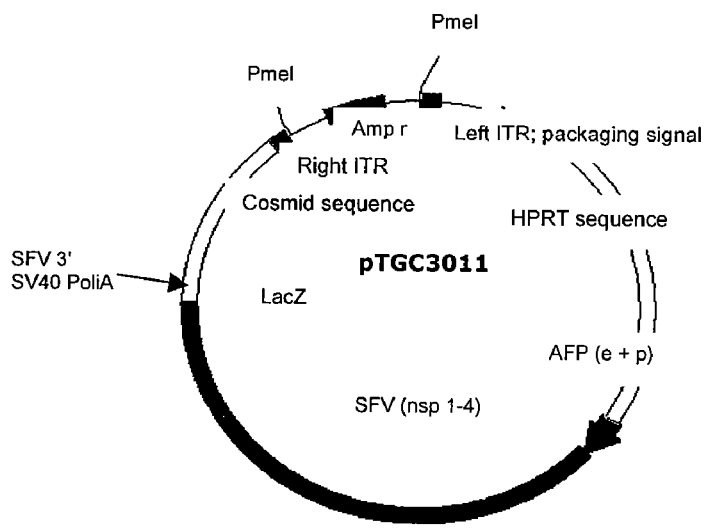

FIGS. 14A and 14B show restriction maps of plasmids pTGC3001 and pTGC3011, respectively.

Figures 15A, 15B:
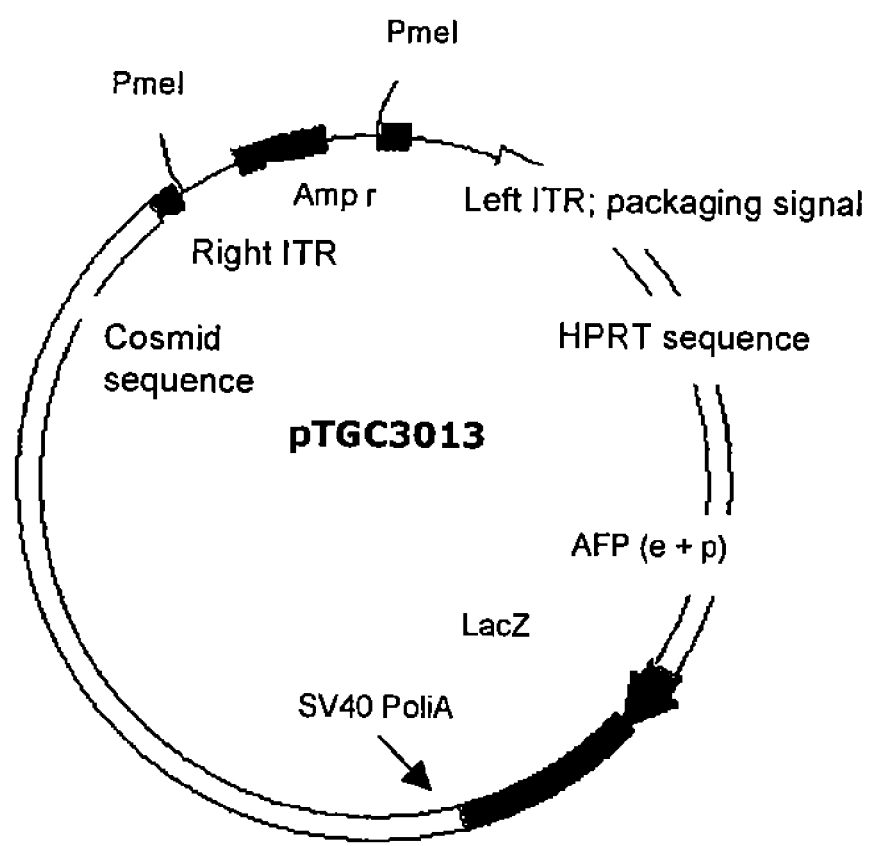

FIGS. 15A and 15B show restriction maps of plasmids pTGC3012 and pTGC3013, respectively.

Figure 16:
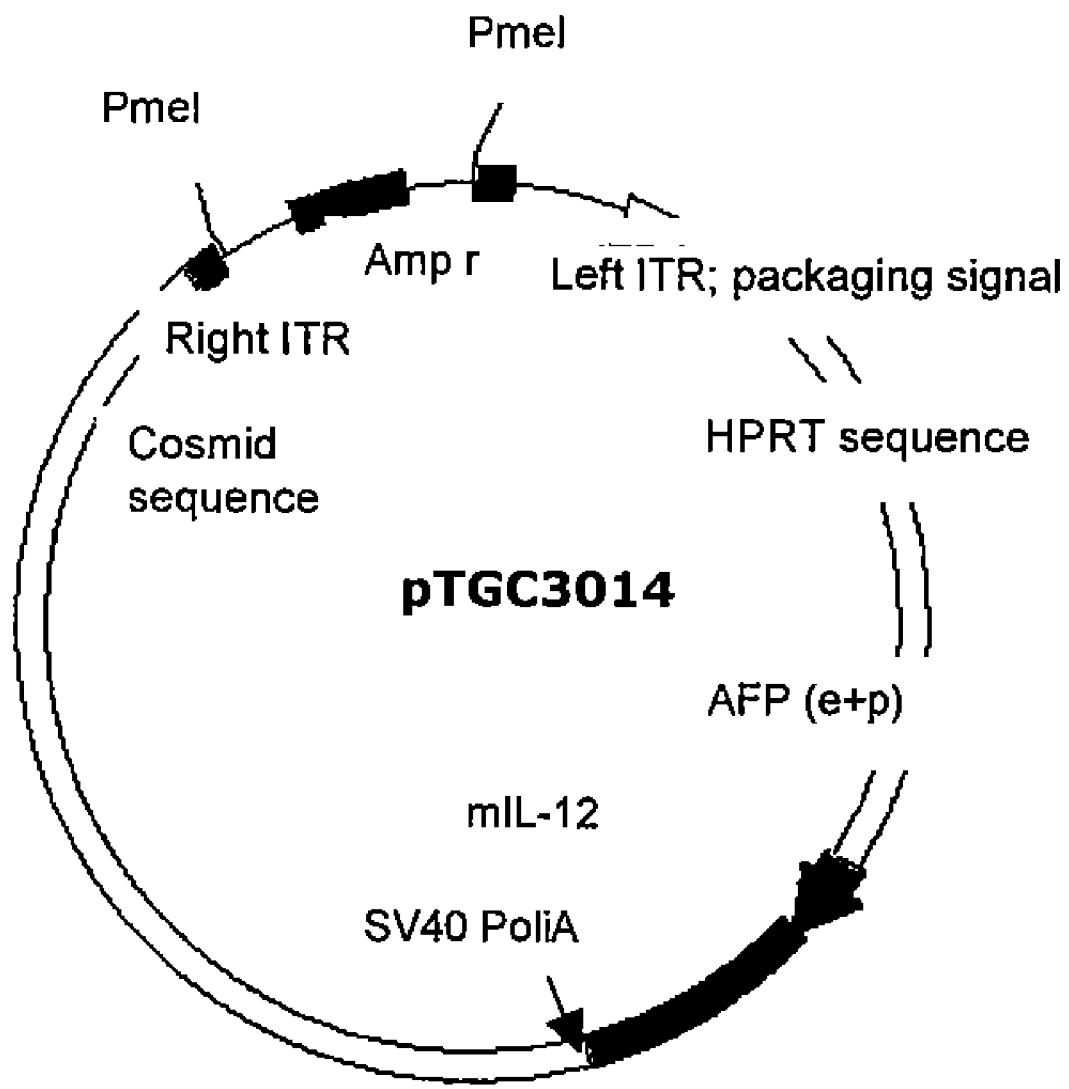

FIG. 16 shows the restriction map of plasmid pTGC3014.

INVENTION EMBODIMENTS

Plasmids pGEM-T "easy" and pCMVb were obtained from Promega, U.S.A., and PBS-SK+ from Stratagene, U.S.A. pSTK120 was kindly donated by Dr. Kochanek (University of Ulm, Germany). pBK-SFV-1 and pBK-SFV-3 have been described by Berglund P. et al. "Enhancing immune responses using suicidal DNA vaccines". *Nature Biotechnology* 1998, 16:562-565. pGL3/AFP and pBS/mIL-12 (Yonglian Sun, Cheng Qian, Dacheng Peng and Jesús Prieto. 2000. Gene transfer to liver cancer cells of B7-1 in addition to IL-12 changes immunoeffector mechanisms and suppresses Th1 cytokine production induced by IL-12 alone. *Human Gene Therapy* 11:127-138) were produced in our laboratory.

For the construction of pGL3/AFP, the regions of the AFP promoter/enhancer (p+e) were obtained via PCR amplification of human genomic DNA. The primers used for amplification of the AFP promoter (AFP pro) were SEQ ID NO. 16: CTCTAGATTTTCTGCCCCAAAGAGCTC and SEQ ID NO. 17: CGGGATCCTGTTATTGGCAGTGGTGGAA. The primers used for amplification of the AFP enhancer were SEQ ID NO. 18: CGGAATTCGCCTGTCATACAGCTAATAA and SEQ ID NO. 19: CTCTAGACTGTCAAATAAGTGG CCTGG. The sequences of the promoter (217 base pairs) and of the enhancer (785 base pairs) were cloned in pGEM-T plasmids. Subsequently, confirmation of the amplified fragments was carried out via sequencing. The AFP promoter was removed from the pGEM-T/AFP-p plasmid by restriction with Xba I/BamHI, and inserted by blunt-end ligation in a pGL3-basic plasmid digested with Sma I. In this way a pGL3/AFP-p plasmid was obtained. The AFP enhancer was removed from the pGEM-T/AFP-e plasmid by restriction with Xba I/Eco RI and was inserted via blunt-end ligation in the pGL3/AFP-p plasmid digested with Nhe I, to finally obtain the pGL3/AFP plasmid.

Cell Lines and Tissue Cultures

The human HCC cell lines Hep3B, PLC/PRF/5, HepG2 and SK-Hep-1, the human cervical epithelial adenocarcinoma cell line HeLa, the human lung carcinoma cell line A549, the human embryonic kidney cell line 293, the rat HCC cell McA-RH7777, MHC1, and Clone 9 of normal rat hepatocytes and the rat HCC cell line Hepa1-6, were obtained from the ATCC. The 293 cells expressing Cre recombinase (293Cre4) were obtained from Merck Research Laboratories. The Hep3B, PLC/PRF/5, HeLa, SK-Hep-1, Clone 9, Huh-7 and Hepa1-6 cells were grown in DMEM medium supplemented with 10% fetal bovine serum (FBS) inactivated by heating and penicillin/streptomycin. The HepG2 and A549 cells were grown in RPMI 1640 medium supplemented with 10% FBS inactivated by heating and penicillin/streptomycin. The McH-RH7777 and MHC1 cells were grown in DMEM medium supplemented with 20% horse serum and 5% FBS. The 293Cre4 cells were grown in DMEM medium supplemented with 10% FBS and 0.4 mg/ml G418.

Animals

Seven-week-old female nude immunodeficient BALB/c mice were obtained from Charles Rivers Laboratories (Barcelona, Spain). Male Buffalo rats aged 4-6 weeks were obtained from CIFA (Animal Installations of the University of Navarra). Mice and rats were housed under the usual conditions in CIFA. The nude mice received an irradiated diet with autoclaved drinking water. Handling of the nude mice was always carried out under a laminar flow chamber. All procedures with animals were carried out in adherence to the standard recommendations and protocols for the care and use of laboratory animals.

Construction of Vectors

Construction of Expression Cassettes AFP-SFV

The 5' end sequence of SFV (1-292 nt) was amplified by PCR using the pBK-SFV-1 plasmid (containing the full sequence of the SFV replicon) as a template. Primer 1 contained an Spe I restriction site at the 5' end (underlined) followed by 50 nt of the AFP promoter sequence and the first 20 nt of the SFV sequence (in italics): SEQ ID NO. 20: 5'-ACTAGT TAA CAG GCA TTG CCT GAA AAG AGT ATA AAA GAA TTTCAG GAT TTT CCA TGG CGG ATG TGT GAC ATA C-3'. Primer 2 contained a Xho I restriction site (underlined) followed by 20 nt of the SFV sequence (in italics): SEQ ID NO. 21: 5'-CTCGAG GAT ATC CAA GAT GAG TGT GT-3'. A DNA fragment with 342 by was generated by PCR and cloned directly into the pGEM-T-easy plasmid to generate pGEM-Te-SFV-1. The absence of PCR errors in this plasmid was confirmed by sequencing. The 342 by fragment was released from pGEM-Te-SFV-1 by digestion with Spe I and Xho I and cloned into pGL3/AFP digested with the same enzymes to yield pGL3/AFP-SFV-1, which possesses the complete AFP promoter (217 bp) and enhancer (785 bp) followed by the 5' end sequence of SFV (SFV-1, comprising 292 bp). An AFP-SFV-1 (1342 bp) cassette was obtained from pGL3/AFP-SFV-1 by Mlu I/Xho I digestion, treated with Klenow and cloned into pBS-SK+ digested with EcoR V, generating pBS/AFP-SFV-1. The SV40 late polyA (262 bp) was removed from pGL3/AFP by Xba I/BamH I digestion, blunted with Klenow and inserted into the Sal I site of pBS/AFP-SFV-1 also blunted with Klenow, thus giving rise to pBS/AFP-SFV-1-pA. A polylinker containing both unique Apa I and Nru I sites was inserted between Bam HI and Xma I sites in pBS/AFP-SFV-1-pA. The 3' end sequence of SFV comprising 7985 bp was removed by digestion with Spe I/EcoR V from pBK-SFV-1, blunted with Klenow and inserted into the EcoR V position of pBS/AFP-SFV-1-pA, giving rise to pBS/AFP-SFV-pA.

LacZ reporter gene was obtained from pCMVb by digestion with Not I, treated with Klenow and inserted into the BamH I site of pBS/AFP-SFV-pA treated with Klenow to form pBS/AFP-SFV-LacZ-pA. A mIL-12 cassette containing the genes encoding for the p35 and p40 subunits linked by the internal ribosome entry site (IRES) was separated from pBS/mIL-12 by digestion with Spe I/Xho I, treated with Klenow and inserted into the BamHI position of pBS/AFP-SFV-mIL-12-pA, also blunted with Klenow, the plasmid pBS/AFP-SFV-mIL-12-pA being generated.

Construction of Hybrid Gutless Adenoviral Vectors

Four gutless adenoviral vectors have been constructed, as shown in FIG. 2. AFP-SFV-lacZ and AFP-SFV-mIL-12 contain a recombinant SFV replicon sequence controlled by the AFP promoter and enhancer. In these vectors the reporter gene LacZ or the therapeutic gene mIL-12 were cloned under the control of the SFV subgenomic promoter, respectively. AFP-lacZ and AFP-mIL-12 are also gutless adenovirus vectors, which contain LacZ and mIL-12 genes, directly controlled by the AFP promoter/enhancer, respectively. The process followed for the construction of these vectors is described below. In order to generate an adenoviral vector with sufficient cloning space to house the AFP-SFV-IL-12 expression cassette, the pSTK120 plasmid containing the sequence of a gutless adenovirus was modified. To that end, a 9-kb fragment was eliminated from the pSTK120 plasmid via digestion with Apa I. In addition, a polylinker containing the sites Asc I and Sbf I was inserted into this new plasmid, giving rise to pTGC3001. This plasmid contains the left ITR, the packaging signal, stuffer DNA from HPRT and C346, and the right ITR. The AFP-SFV-LacZ cassette was separated by digestion with Apa I from pBS/AFP-SFV-lacZ-pA and inserted in the Apa I site of pTGC3001, giving rise to pTGC3011. Similarly, the AFP-SFV-mIL-12 cassette was released from pBS/AFP-SFV-mIL-12-pA by digestion with BssH II, treated with Klenow and inserted in the Asc I site of pTGC3001, likewise treated with Klenow to generate pTGC3012.

Construction of Control Vectors

Construction of the Gutless Adenoviral Vector AFP-LacZ

The AFP enhancer/promoter (AFP p+e) sequence was separated from pGL3/AFP by digestion with Mlu I/Xho I, treated with Klenow and inserted into pCMVb, which had been previously digested with EcoRI/Xho I and treated with Klenow. In this way the CMV immediate early promoter was removed from pCMVb and substituted by AFP (p+e) to generate pAFPb. The AFP-LacZ cassette (5077 bp) was subsequently removed from pAFPb by digestion with Xba I/Nar I, treated with Klenow, and inserted into the Swa I site of pSTK120, also blunted with Klenow, giving rise to pTGC3013.

Construction of the Gutless Adenoviral Vector AFP-mIL-12

The mIL-12 cassette was removed from pBS/mIL-12 by digestion with Xho I/Spe I, and inserted in pGL3/AFP previously digested with Xho I/Xba I, which eliminated the luciferase gene from this latter plasmid and generated pAFP-mIL-12. The AFP-mIL-12 cassette (3760 bp) was removed from pAFP-mIL-12 by digestion with BamH I/Sca I, treated with Klenow and inserted in pSTK120 digested by Swa I, and likewise treated with Klenow to generate pTGC3014.

Rescue of the Gutless Adenoviral Vectors

Following Pme I digestion, phenol/chloroform extraction, and ethanol precipitation, 2 μg of pTGC3011, pTGC3012, pTGC3013, or pTGC3014 DNA were transfected into 293Cre4 cells, respectively. After transfection, cells were infected with helper virus AdLC8cluc. Subsequent large-scale amplification and preparation steps were performed as previously described (Philip Ng., Robin J. Parks, and Frank L. Graham. Preparation of helper-dependent adenoviral vectors. *Methods in Molecular Medicine*, Vol. 69, *Gene Therapy Protocols*, $2^{nd}$. Ed. 69, 371-88, 2002; H. Zhou, L. Pastore, A. L. Beaudet. Helper-dependent adenoviral vectors. *Methods in Enzymology, vol*, 346, 177-198, 2002; Hillgenberg M., et al. System for efficient helper-dependent minimal adenovirus constructions and rescue. *Hum Gene Ther.*, 12; 643-657, 2001). All vector preparations were purified twice by CsCl gradient centrifugation. The purified DNA vectors were analyzed by digestion with restriction enzymes and showed no sequence rearrangements. Titration of gutless adenovirus and helper virus contamination was evaluated using quantitative PCR. The proportion of total viral particles versus the infectious units (iu) was 20:1. Contamination by helper virus particles was approximately 0.5-1%.

Quantitative PCR

To determine the degree of helper virus contamination, a probe and primers for the quantitative PCR of the Ad5 E4 region were designed using the TaqMan program (TaqMan Probe #2), and were synthesized by Sigma-Genosys Ltd. (primer) and Applied Biosystems (probe). To determine the titer of gutless adenoviruses, probes and primers for the quantitative PCR of the LacZ and mIL-12 sequences from mice were designed using the TaqMan program (TaqMan Probe #2), and were synthesized by Sigma-Genosys Ltd (primer) and Applied Biosystems (probe). To determine the contamination by wild-type Ad, probes and primers for the quantitative PCR of the Ad5 E1 region were designed using the TaqMan program (TaqMan Probe #2), and were synthesized by Sigma-Genosys Ltd. (primer) and Applied Biosystems (probe).

In Vitro Experiments

Transgenic Expression in Cells Infected with Gutless Adenoviral Vectors

Cell lines derived from HCC (Hep3B, Huh7, HepG2, and PLC/PRF/5) and cell lines that are not derived from HCC (A549, HeLa, MHC1 and Clone 9) or cell lines that are derived from HCC but do not express AFP (SK-Hep-1) were infected with each of the four gutless adenoviral vectors (AFP-LacZ, AFP-SFV-LacZ, AFP-mIL-12, or AFP-SFV-mIL-12) at "moi" 1000, 100, or 10 (particles/cell), respectively. Three first generation adenoviruses (Ad/CMV-mIL-12, Ad/CMV-LacZ Ad/AFP-LacZ) were used as control. Supernatants from cells infected with mIL-12 vectors and lysates from cells infected with LacZ vectors were collected in duplicate from wells for determination of mIL-12 and β-galactosidase (β-gal) levels, respectively. Cells infected with LacZ vectors were also stained with X-gal. The mIL-12 level (p70) was measured with an ELISA kit (Pharmingen, San Diego, Calif.). The β-gal level was measured with an ELISA kit (Roche, Switzerland). The time course of mIL-12 expression was evaluated in HCC cells (Hep3B, Huh7) after infection with AFP-mIL-12, AFP-SFV-mIL-12, or with the control vector Ad/CMV-mIL-12 at a "moi" of 1000. Supernatants were collected daily until 5 days after the infection.

Analysis of the Specificity of Transgenic Expression Using Ad-SFV Hybrid Vectors In Vitro To examine the specificity of transgenic expression with the previously described recombinant vectors, four human HCC cell lines (Hep3B, HepG2, Huh-7 and PLC/PRF/5) and two human cell lines that are not derived from HCC (HeLa and A549) or that are derived from HCC but do not express AFP (SK-Hep-1) were infected with AFP-mIL-12, AFP-SFV-mIL-12 or Ad-CMV-mIL-12 as positive control at different "moi" (10, 100, or 1000). Two days after infection, the supernatant was collected and its mIL-12 content was determined. The results are shown in FIG. 3 (A) and (B). No mIL-12 expression was observed in the human HCC cells when infected with AFP-mIL-12 at "moi" 10 or 100, and only at "moi" 1000 a very low level of mIL-12 was seen in some cell lines (FIG. 3A). In contrast, the infection of these cells with AFP-SFV-mIL-12 at "moi" 10, 100, or 1000 gave rise to the expression of mIL-12 in a dose-dependent manner (FIG. 3A). The level of mIL-12 expression in cells infected with "moi" 10 of AFP-SFV-mIL-12 was comparable to the level obtained in cells infected with AFP-mIL-12 at "moi" 1000. In addition, the level of mIL-12 in HCC cells infected with AFP-SFV-mIL-12 at different "moi" was comparable to that obtained with the control vector Ad-CMV-mIL-12. However, the infection of cells that do not express AFP with AFP-mIL-12 or AFP-SFV-mIL-12 yielded no detectable levels of mIL-12, even when using the highest "moi" (1000) (FIG. 3B). In these cells, only the control vector Ad-CMV-mII-12 was able to generate a high level expression of mIL-12.

On the other hand, four HCC cell lines (Hep3B, Huh-7, HepG2 and PLC/PRF/5) were infected with hybrid vectors of LacZ—AFP-lacZ, or AFP-SFV-lacZ—at different "moi" (10, 100, or 1000), and the specific expression of β-gal was determined. Similar data were likewise obtained in this case, the results of which are shown in FIG. 4.

FIG. 5 shows microphotographs of HCC cells infected with the gutless adenoviral vectors AFP-lacZ and AFP-SFV-lacZ, followed by staining with X-gal. The infection of HCC cells with AFP-lacZ resulted in a low level expression in the infected cells, which were only weakly stained. In contrast, the infection of HCC cells with AFP-SFV-lacZ led to a high level expression of β-gal, reflected by intense staining with X-gal. This data indicates that a hybrid vector Ad-SFV comprising an SFV replicon under the control of the AFP promoter may give rise a high level of intense transgenic expression in tumor cells that express AFP.

Time Course of the Expression of mIL-12 in HCC Cells In Vitro

To study the production of mIL-12 at different times following infection with the Ad-SFV hybrid vectors, two HCC cell lines (Hep3B and Huh-7) were infected with AFP-mIL-12 or with AFP-SFV-mIL-12, and the supernatants were collected daily for 5 days following infection. FIG. 6 shows the transgenic expression results obtained after the infection of the mentioned cells. Said results reflect a constant increase in the expression of mIL-12 from day 1 to day 4 after the infection in cells infected with AFP-SFV-mIL-12 (FIG. 6). However, on day 5 following infection, the mIL-12 levels decreased slightly. In the cells infected with AFP-mIL-12, the levels of expression were very low, and only a slight increase in the production of mIL-12 was noted over time.

Cytotoxicity Testing—Evaluation of Cell Proliferation by MTT Incorporation

HCC cells (Hep3B, Huh7, MCH-RH7777, Hep1-6) were infected with AFP-LacZ, AFP-SFV-LacZ, AFP-mIL-12, AFP-SFV-mIL-12, or Ad/CMV-mIL-12 at "moi" 1000. Five days after the infection, cell survival was determined by an MTT assay (3-(4,5-dimethylthiazolyl)-2,5-diphenyltetrazolium bromide) Mosmann, T. (1983) *J. Immunol. Meth.* 65, 55-63; Tada, H. et al. (1986) *J. Immunol. Meth.* 93, 157-65. Briefly, cells were washed once with PBS and 200 µl of freshly prepared MTT dye solution was added per well (in 48-well plates). Cells were further cultured for 3-4 hours followed by addition of 500 µl of solubilization buffer. 100 µl of each sample were taken for the measurement of absorbance in a spectrophotometer at a wavelength of 570 nm.

Induction of Cell Death Following HCC Cell Infection with Ad-SFV Hybrid Vectors In Vitro It has been described that the replication of SFV vectors induces cell death mediated by apoptosis in most cells of vertebrate origin. In order to evaluate whether this is also the case in HCC cells infected with Ad-SFV hybrid vectors, Hep3B and Huh-7 cells were infected with these vectors and cell survival was determined on day 5 following infection. As can be seen in FIG. 7, survival at this post-infection timepoint was less than 20% in cells infected with AFP-SFV-mIL-12, or with AFP-SFV-lacZ. However, infection of these same cells with AFP-mIL-12 or AFP-lacZ, or with the control vector AdCMVmIL-12, did not affect cell survival. These results indicate that SFV replicates in cells infected with AFP-SFV vectors.

Detection of SFV Rep by Immunofluorescence

HCC cells (Hep3B, Huh7, MCH-RH7777) were seeded on glass coverslips in 6-well plates ($1 \times 10^5$ cells/well) and infected with AFP-mIL-12, AFP-SFV-mIL-12, or Ad/CMV-mIL-12 at "moi" 1000. Two days after infection coverslips were washed twice with PBS, and cells were fixed with methanol at −20° C. for 6 min. The plates were again washed three times with PBS and incubated at room temperature (RT) during 30 min. with PBS containing 0.5% gelatin and 0.25% BSA to block nonspecific binding. The blocking buffer was then replaced with the primary antibody (anti-replicase MAb) diluted 1:10 in blocking buffer, and was incubated at RT for 30 min. The cells were again washed three times with PBS-0.25% BSA, and incubated for 30 min. at RT with the secondary antibody (antimouse rabbit serum conjugated with FITC, Sigma) diluted 1:250 in blocking buffer. Finally, the cells were washed three times with PBS-0.25% BSA, once with water, and arranged on glass slides using Vecta shield with Dapi in order to stain the cell nuclei.

Expression of SFV Rep in HCC Cells Infected with Ad-SFV Hybrid Vectors In Vitro

The expression of SFV Rep was examined in HCC cells infected with Ad-SFV hybrid vectors via immunofluorescence with a specific monoclonal antibody for this protein. FIG. 8 shows that the HCC cells infected with AFP-SFV-mIL-12 or AFP-SFV-lacZ exhibited intense cytoplasmic positivity for Rep. In contrast, the cells infected with AFP-mIL-12 or AFP-lacZ showed no staining.

In Vivo Experiments

Induction of HCC Xenografts and Study of In Vivo Gene Transfer Efficiency and Specificity Huh-7 cells were collected and washed twice with serum-free medium. $2 \times 10^6$ cells were resuspended in 100 µl saline serum and injected subcutaneously (s.c.) into the right flank of BALB/c nude mice. Four weeks after the inoculation of the cells, and when tumor nodules reached 6-8 mm in diameter, $1 \times 10^{10}$ viral particles of AFP-LacZ (n=4) or of AFP-SFV-LacZ (n=4) diluted in 80 µl of saline were injected intratumorally. Control animals (n=3) were injected intratumorally with 80 µl of saline. Mice were sacrificed on day 3 or 6 after the inoculation. At these times the tumors and livers were taken from each animal, embedded in O.C.T. (Sakura, Holland), and frozen at −80° C. Frozen tissues were sectioned and placed on glass slides to be stained with X-gal or analyzed by TUNEL., To study the specificity of the infection with the hybrid vector in vivo, normal Balb/c mice were injected intravenously with AFP-LacZ (n=4), AFP-SFV-LacZ (n=4) or Ad/CMV-LacZ at a dose of $10^{10}$ viral particles/mouse. The animals were sacrificed on the third day after the inoculation and the main organs were collected to analyze the expression of LacZ by means of staining with X-gal.

Efficiency of Gene Transfer of Ad-SFV Hybrid Vectors in Human HCC Xenografts in Nude Immunodeficient Mice To study the efficiency of the transduction of gutless hybrid vectors in vivo, a human HCC model based on Huh7 cells capable of expressing AFP was employed. The Huh7 cells were inoculated subcutaneously in nude immunodeficient Balb/c mice, and after the generation of tumor nodules after 30 days, the animals were injected intratumorally with $1 \times 10^{10}$ viral particles of AFP-SFV-LacZ or AFP-LacZ as control. The mice were sacrificed 3 or 6 days after the injection of the virus, and both the tumor and liver were removed and examined by staining with X-gal. As can be seen in FIG. 9A, there is a weak transgenic expression in tumor sections of animals that have received AFP-lacZ. In contrast, there is an intense expression of LacZ in tumor sections of animals that received AFP-SFV-LacZ (FIG. 9B). No transgenic expression was observed in liver sections from animals that received either AFP-LacZ or AFP-SFV-LacZ, indicating that the vectors were probably confined in the inoculation site (data not shown). With the aim of studying whether the Ad-SFV hybrid vectors induce apoptosis in infected tumor cells, treated tumor sections were analyzed by means of the TUNEL technique. No apoptosis was observed in the samples from mice inoculated with AFP-LacZ (FIG. 9C). However, an abundant amount of apoptotic cells was observed in the tumors of animals who had received AFP-SFV-LacZ (FIG. 9D). This data indicates that Ad-SFV hybrid vectors not only induce gene expression specifically in tumors but they also induce selective cell death by apoptosis in these same cells.

In Vivo Specificity of Ad-SFV Hybrid Vectors

To show the specificity of the hybrid vectors, $10^{10}$ viral particles of AFP-LacZ, AFP-SFV-LacZ or of the control vector Ad/CMV-LacZ were administered intravenously in Balb/c mice. Three days after the administration of the vectors, the expression of β-galactosidase in liver was analyzed. As shown in FIG. 9 (E-F), neither AFP-LacZ nor AFP-SFV-LacZ were able to induce detectable expression of the transgene in liver. However, a high proportion of β-galactosidase positive cells in hepatic tissue sections was observed in those animals that received Ad/CMV-LacZ (FIG. 9G). These data confirm that the expression mediated by the hybrid vectors is specific for tumor cells.

Orthotopic HCC Induction and Gene Therapy In Vivo $5 \times 10^5$ McA-RH7777 cells were inoculated in the left lobe of the liver of Buffalo rats. Ten days after the inoculation of the tumor cells, the appearance of a single tumor nodule of 7-10 mm in diameter was observed in each animal. The tumors were treated with $10^{11}$ or $2 \times 10^{11}$ viral particles of AFP-mIL-12, AFP-SFV-mIL-12, or with saline solution as control. Two and four weeks after treatment, the animals were anesthetized and subjected to laparotomy to observe the evolution of the tumor. An analysis of animal survival was also made. The size of the tumors was assessed by measuring the length and width of each nodule and applying the formula: Tumor volume=(length in mm)×(width in mm)$^2$×0.5236 (Janik et al., 1975).

Efficiency of Orthotopic HCC Treatment in Buffalo Rats

In order to investigate the anti-tumor efficiency of the Ad-SFV hybrid vector carrying IL-12, orthotopic HCC tumors were established in rats by implanting rat McH-RH7777 cells in the liver. This model was chosen because it has been demonstrated that McH-RH7777 cells express AFP. In a first experiment, the animals were treated with a single intratumor injection of 1×10$^{11}$ viral particles of AFP-mIL-12, AFP-SFV-mIL-12, or with saline solution as control (FIG. 10A-C). The animals that received AFP-mIL-12 showed a reduced tumor size compared with the control animals, which suffered a constant increase in tumor size throughout the experiment (FIG. 10A-B). However, treatment with AFP-SFV-mIL-12 resulted in a complete regression of the tumor in 1 of 4 treated rats, stabilization of the disease in two, and an absence of response in 1 animal (FIG. 10C). For the purpose of verifying whether larger doses of the hybrid vector could increase the anti-tumor effect, a second experiment was carried out in which the animals were treated intratumorally with a dose of 2×10$^{11}$ viral particles of AFP-mIL-12, AFP-SFV-mIL-12, or with saline solution as control (FIG. 10 D-G). As in the previous experiment, the animals that received the AFP/IL-12 vector showed only a slight anti-tumor response, which translated into only one complete remission, 4 animals with tumors that grew more slowly than in the controls, and 7 animals with no response, of a total of 12 treated animals (FIG. 10E). However, treatment with the AFP-SFV-IL-12 vector had a much more potent effect, inducing a complete tumor regression in four animals (33%), partial regression in 6 animals (50%), delayed tumor growth progression in 2 animals (16%), and no response in another 2 animals (16%), of a total of 12 treated animals (FIG. 10F). In this second study the AFP/SFV-IL-12 vector allowed the survival of 50% of the animals treated, versus 0% survival among the animals treated with AFP-IL-12 or with saline solution (FIG. 10G).

In Vivo Toxicity Study: Determination of Serum Transaminases and IL-12 Levels, and Liver Histological Evaluation Blood samples were collected from the rats treated intratumorally with the adenoviral vectors AFP-SFV-IL-12 or AFP-IL-12 at a dose of 2×10$^{11}$, or with saline solution, 4 and 8 days after the inoculation. This study also included rats inoculated with 10$^8$ particles of the alphavirus SFV-IL-12. Serum was separated from blood by centrifugation at 2000 rpm for 15 minutes. Transaminase levels were determined using a Hitachi 911 Automatic Analyzer (Boehringer Mannheim, Germany). The IL-12 levels were determined by ELISA. The histological study was carried out by the extraction of the liver in the animals inoculated three days after the treatment. The organ was fixed in formol, embedded in paraffin and sectioned to a thickness of 6 microns with a microtome. These sections were then stained with hematoxylin/eosin.

Study of the Toxicity of Ad-SFV Hybrid Vectors in Rats

Figure 11A:
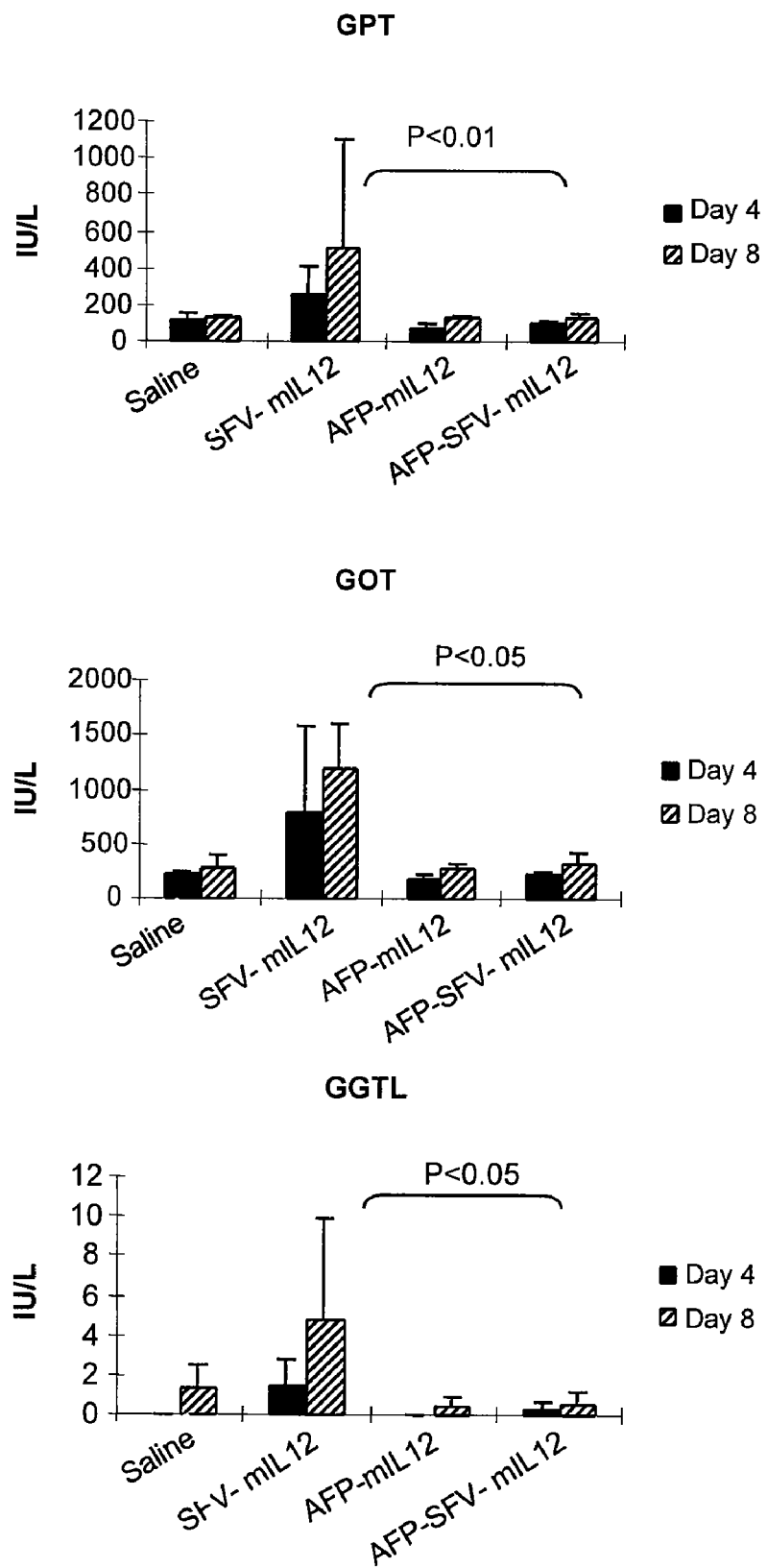
Figure 11B:
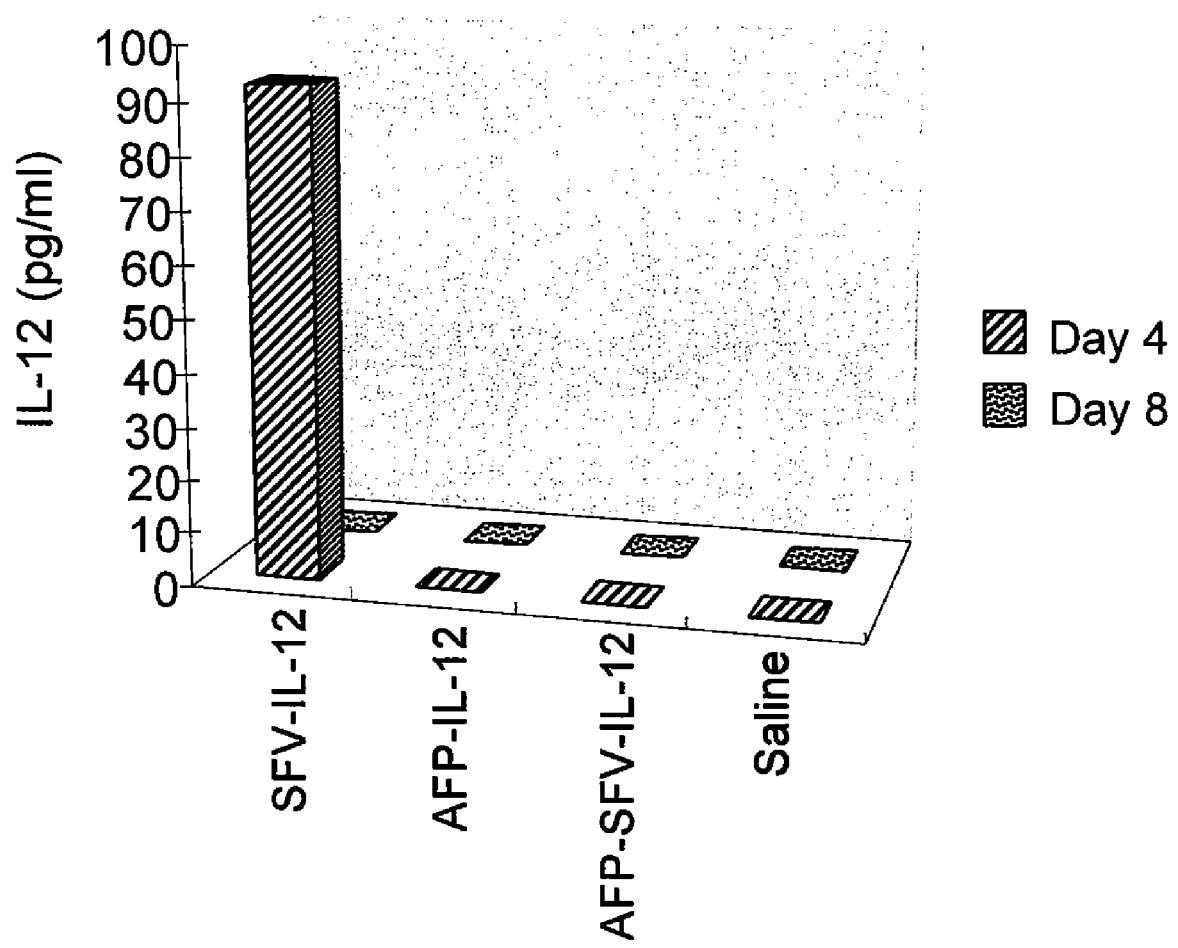

To evaluate toxicity associated with the administration of the AFP-SFV-IL-12 hybrid vector, the levels of transaminases (GOT, GPT and GGTL) were determined in the serum of rats treated intratumorally with 2×10$^{11}$ viral particles of the different vectors (see previous section). This study also included a group of rats also inoculated intratumorally with 10$^8$ viral particles of alphaviral vector SFV-IL-12 (FIG. 11A). The rats inoculated with the AFP-SFV-IL-12 or AFP-IL-12 adenoviral vectors showed very low transaminase levels that were very similar to the levels of control animals inoculated with saline solution. However, the transaminase levels in the animals treated with the particles of SFV-IL-12 were significantly greater than in the other groups (p<0.05). In this study, determinations of the IL-12 level present in the serum of the animals at the same timepoints were also made. No IL-12 was detected in the serum of the animals inoculated with the Ad AFP-SFV-IL-12 or AFP-IL-12 vectors, or with saline solution (FIG. 11B), indicating that expression of the transgene in these vectors is restricted to the tumors, and suggesting that the toxicity of the Ad-SFV hybrid vector is very low. Treatment with the SFV-IL-12 viral particles, however, induced high serum levels of IL-12 after short periods of time, a situation that could cause liver toxicity. Finally, the toxicity study was completed with a histological analysis of liver sections stained with hematoxylin/eosin from rats treated intratumorally with the same vectors and at the same doses already described (FIG. 12). This study showed no histological differences between the rats that received saline solution and those that received the AFP-SFV-IL-12 or AFP-IL-12 adenoviral vectors. However, areas with eosinophilic hepatocytes as well as the fusion of these hepatocytes was observed in liver sections of rats treated with SFV-IL-12 viral particles, indicating a certain degree of toxicity (black arrows, FIG. 12D).

The invention claimed is:

1. A genic expression adenoviral hybrid vector for expressing a gene of interest directly in an adenovirus-permissive cell in which a tissue-specific promoter is active, wherein said tissue specific promoter is the tumor specific promoter AFP, characterized in that the genic expression adenoviral hybrid vector comprises at least the following elements, oriented in the direction 5' to 3':
   i. a first chain of adenoviral origin comprising a first inverted terminal repeat (ITR) sequence and a signal sequence for packaging of the adenovirus;
   ii. a first non-encoding stuffer sequence;
   iii. a sequence corresponding to a tissue specific promoter, wherein said tissue specific promoter is the tumor specific promoter AFP;
   iv. a chain of cDNA derived from an alphavirus, the sequence of which is partly complementary to an alphaviral RNA sequence, comprising at least a sequence encoding for at least one exogenous gene of interest; said chain of cDNA derived from an alphavirus comprising:
   (a) a 5' sequence necessary for replication of the alphavirus,
   (b) a sequence encoding for the non-structural proteins required for replication of the alphaviral RNA,
   (c) at least one subgenomic promoter of the alphavirus, and
   (d) a 3' sequence necessary for replication of the alphavirus;
      wherein said sequence encoding for at least one exogenous gene of interest is under the control of said at least one subgenomic promoter of the alphavirus; and said chain of cDNA derived from an alphavirus is functionally controlled by the promoter iii;

v. a polyadenylation sequence; and vi. a second adenoviral inverted terminal repeat (ITR) sequence.

2. A genic expression adenoviral hybrid vector according to claim 1, further comprising an element vii which is a second non-encoding stuffer sequence located between element v and element vi.

3. A genic expression adenoviral hybrid vector according to claim 1, characterized in that element ii is a human non-encoding stuffer sequence.

4. A genic expression adenoviral hybrid vector according to claim 3, characterized in that element ii is the intron region of human genomic hypoxanthine phosphoribosyltransferase, HPRT.

5. A genic expression adenoviral hybrid vector according to claim 1, characterized in that element i comprises the sequence SEQ ID NO: 1.

6. A genic expression adenoviral hybrid vector according to claim 1, characterized in that element iii is a tumor specific promoter having the sequence SEQ ID NO: 7, corresponding to AFP p+e.

7. A genic expression adenoviral hybrid vector characterized in that the genic expression adenoviral hybrid vector comprises at least the following elements, oriented in the direction 5' to 3':

i. a first chain of adenoviral origin comprising a first inverted terminal repeat (ITR) sequence and a signal sequence for packaging of the adenovirus;

ii. a first non-encoding stuffer sequence;

iii. a sequence corresponding to a tissue specific promoter, wherein said tissue specific promoter is the tumor specific promoter AFP;

iv. a chain of cDNA derived from an alphavirus, the sequence of which is partly complementary to an alphaviral RNA sequence, comprising at least a sequence encoding for at least one exogenous gene of interest; said chain of cDNA derived from an alphavirus comprising:

(a) a 5' sequence necessary for replication of the alphavirus, (b) a sequence encoding for the non-structural proteins required for replication of the alphaviral RNA, (c) at least one subgenomic promoter of the alphavirus, and (d) a 3' sequence necessary for replication of the alphavirus;

wherein said sequence encoding for at least one exogenous gene of interest is under the control of said at least one subgenomic promoter of the alphavirus; and said chain of cDNA derived from an alphavirus is functionally controlled by the promoter iii;

v. a polyadenylation sequence; and vi. a second adenoviral inverted terminal repeat (ITR) sequence;

wherein said at least one exogenous gene of interest is expressed directly in an adenovirus-permissive cell in which a tissue-specific promoter is active, and wherein said tissue specific promoter is the tumor specific promoter AFP.

8. The genic expression adenoviral hybrid vector according to claim 1, wherein said element iv comprises a sequence derived from the Semliki Forest Virus (SFV).

9. A genic expression adenoviral hybrid vector according to claim 8, characterized in that element iv a), b) and c) comprises, as a whole, a sequence selected from the group consisting of SEQ ID NO: 3 and SEQ ID NO: 4.

10. A genic expression adenoviral hybrid vector according to claim 9, characterized in that element iv d) has the sequence SEQ ID NO: 5.

11. A genic expression adenoviral hybrid vector according to claim 1, characterized in that the exogenous gene of interest is selected from the group consisting of one or more therapeutic genes, one or more reporter genes, and combinations thereof.

12. A genic expression adenoviral hybrid vector according to claim 11, characterized in that the exogenous gene of interest is the mammalian interleukin IL-12 therapeutic gene.

13. A genic expression adenoviral hybrid vector according to claim 11, characterized in that the exogenous gene of interest is the human interleukin hIL-12 therapeutic gene.

14. A genic expression adenoviral hybrid vector according to claim 9, characterized in that element iv comprises (subgenomic promoter+exogenous gene of interest) in series or in several subsets.

15. A genic expression adenoviral hybrid vector according to claim 1, characterized in that element iv forms a replicon functionally controlled by the promoter iii, and in that the alphaviral subgenomic promoter in iv.c) functionally controls the expression of the exogenous gene of interest.

16. A genic expression adenoviral hybrid vector according to claim 1, characterized in that element v is a polyadenylation sequence of SV40.

17. A genic expression adenoviral hybrid vector according to claim 16, characterized in that element v comprises the sequence SEQ ID NO: 6.

18. A genic expression adenoviral hybrid vector according to claim 2, characterized in that the second non-encoding stuffer sequence is C346.

19. A genic expression adenoviral hybrid vector comprising:

i. a first chain of adenoviral origin comprising a first inverted terminal repeat (ITR) sequence and a signal sequence for packaging of the adenovirus;

ii. a first non-encoding stuffer sequence, which is the intron region of human genomic hypoxanthine phosphoribosyltransferase (HPRT);

iii. a sequence corresponding to a tissue specific promoter, which is the AFP promoter, iv. a cDNA chain derived from an alphavirus, the sequence of which is partly complementary to an alphaviral RNA derived from the SFV virus, which comprises a sequence encoding for an exogenous gene of interest which is hIL-12, v. a polyadenylation sequence of SV40, vi. a second adenoviral inverted terminal repeat (ITR) sequence and vii. a second non-encoding stuffer sequence, which is human genomic C346, located between element v and element vi.

20. A genic expression adenoviral hybrid vector according to claim 1, characterized in that said vector has a length comprised between 27 and 38 kilobases.

21. A genic expression adenoviral hybrid vector characterized in that the genic expression adenoviral hybrid vector comprises at least the following elements, oriented in the direction 5' to 3':

i. a first chain of adenoviral origin comprising a first inverted terminal repeat (ITR) sequence and a signal sequence for packaging of the adenovirus;

ii. a first non-encoding stuffer sequence;

iii. a sequence corresponding to a tissue specific promoter;

iv. a cDNA chain derived from an alphavirus, the sequence of which is partly complementary to an alphaviral RNA sequence derived from the SFV virus, comprising at least a sequence encoding for at least one exogenous gene of interest;

v. a polyadenylation sequence;

vi. a second adenoviral inverted terminal repeat (ITR) sequence; AND vii. a second non-encoding stuffer sequence located between element v and element vi, wherein the vector comprises the sequence of SEQ ID NO:8.

22. A method of transferring genetic material to a cell comprising the steps of administering the adenoviral hybrid vector of claim 1 to a subject.

23. The method according to claim 22 wherein said cell is a tumor cell.

24. The method according to claim 23 wherein said cell is a tumor cell expressing AFP.

25. A method of treating hepatocarcinoma tumors in a subject comprising the step of directly administering the adenoviral vector of claim 1 comprising a nucleotide sequence encoding IL-12 to said tumor in a subject.

26. A method for inducing an immune response against foreign antigens comprising the steps of administering said adenoviral hybrid vector of claim 1 to a subject.

27. A pharmaceutical composition comprising at least one adenoviral hybrid vector according to claim 1.

28. The pharmaceutical composition according to claim 27, characterized in that said composition comprises at least one adenoviral hybrid vector defined according to claim 1, wherein the exogenous gene of interest is hIL-12.

29. A method of inducing an immune response against foreign antigens in a subject comprising the steps of administering to said subject the pharmaceutical composition of claim 27, the hybrid vector further comprising a sequence encoding a foreign antigen of interest.

* * * * *

UNITED STATES PATENT AND TRADEMARK OFFICE
CERTIFICATE OF CORRECTION

PATENT NO.         : 7,850,957 B2                    Page 1 of 1
APPLICATION NO.    : 11/569303
DATED              : December 14, 2010
INVENTOR(S)        : Cheng Qian et al.

It is certified that error appears in the above-identified patent and that said Letters Patent is hereby corrected as shown below:

In item (73) on the cover page, please change the name of the Assignee to:

"Proyecto De Biomedicina Cima, S.L."

In column 11, please change line 48 to:

"(underlined) followed by 19 nt of the SFV sequence (in ital-"

In column 11, please change line 50 to:

"CAG TGT GT-3', A DNA fragment with 342 bp was gener-"

In column 11, please change line 53 to:

"in this plasmid was confirmed by sequencing. The 342 bp"

Signed and Sealed this
Fifteenth Day of March, 2011

David J. Kappos
*Director of the United States Patent and Trademark Office*

SEQUENCE LISTING

```
<160> NUMBER OF SEQ ID NOS: 21

<210> SEQ ID NO 1
<211> LENGTH: 438
<212> TYPE: DNA
<213> ORGANISM: Adenovirus

<400> SEQUENCE: 1
aaacatcatc aataatatac cttattttgg attgaagcca atatgataat gaggggggtgg      60 agtttgtgac gtggcgcggg gcgtgggaac ggggcgggtg acgtagtagt gtggcggaag     120
tgtgatgttg caagtgtggc ggaacacatg taagcgacgg atgtggcaaa agtgacgttt     180
ttggtgtgcg ccggtgtaca caggaagtga caattttcgc gcggttttag gcggatgttg     240
```

-continued

```
tagtaaattt gggcgtaacc gagtaagatt tggccatttt cgcgggaaaa ctgaataaga      300
ggaagtgaaa tctgaataat tttgtgttac tcatagcgcg taatatttgt ctagggccgc      360
ggggactttg accgtttacg tggagactcg cccaggtgtt tttctcaggt gttttccgcg      420
ttccgggtca aagttggc                                                    438

<210> SEQ ID NO 2
<211> LENGTH: 161
<212> TYPE: DNA
<213> ORGANISM: Adenovirus

<400> SEQUENCE: 2
caagcttatc gataccgtcg agacctcgag ggggggcatc actccgccct aaaacctacg       60
tcacccgccc cgttcccacg ccccgcgcca cgtcacaaac tccaccccct cattatcata      120
ttggcttcaa tccaaaataa ggtatattat tgatgatgtt t                          161

<210> SEQ ID NO 3
<211> LENGTH: 7412
<212> TYPE: DNA
<213> ORGANISM: Semliki Forest Virus (SFV)

<400> SEQUENCE: 3
gatggcggat gtgtgacata cacgacgcca aaagattttg ttccagctcc tgccacctcc       60
gctacgcgag agattaacca cccacgatgg ccgccaaagt gcatgttgat attgaggctg      120
acagcccatt catcaagtct ttgcagaagg catttccgtc gttcgaggtg gagtcattgc      180
aggtcacacc aaatgaccat gcaaatgcca gagcattttc gcacctggct accaaattga      240
tcgagcagga gactgacaaa gacacactca tcttggatat cggcagtgcg ccttccggaa      300
gaatgatgtc tacgcacaaa taccactgcg tatgccctat gcgcagcgca gaagaccccg      360
aaaggctcga tagctacgca aagaaactgg cagcggcctc cgggaaggtg ctggatagag      420
agatcgcagg aaaaatcacc gacctgcaga ccgtcatggc tacgccagac gctgaatctc      480 ctacctttg cctgcataca gacgtcacgt gtcgtacggc agccgaagtg gccgtatacc      540
aggacgtgta tgctgtacat gcaccaacat cgctgtacca tcaggcgatg aaaggtgtca      600
gaacggcgta ttggattggg tttgacacca cccgtttat gtttgacgcg ctagcaggcg      660
cgtatccaac ctacgccaca aactgggccg acgagcaggt gttacaggcc aggaacatag      720
gactgtgtgc agcatccttg actgagggaa gactcggcaa actgtccatt ctccgcaaga      780
agcaattgaa accttgcgac acagtcatgt tctcggtagg atctacattg tacactgaga      840
gcagaaagct actgaggagc tggcacttac cctccgtatt ccacctgaaa ggtaaacaat      900
cctttaccct taggtgcgat accatcgtat catgtgaagg tacgtagtt aagaaaatca      960 ctatgtgccc cggcctgtac ggtaaaacgg tagggtacgc cgtgacgtat cacgcggagg     1020
gattcctagt gtgcaagacc acagacactg tcaaaggaga aagagtctca ttccctgtat     1080
gcacctacgt cccctcaacc atctgtgatc aaatgactgg catactagcg accgacgtca     1140
caccggagga cgcacagaag ttgttagtgg gattgaatca gaggatagtt gtgaacggaa     1200
gaacacagcg aaacactaac acgatgaaga actatctgct tccgattgtg gccgtcgcat     1260
ttagcaagtg ggcgagggaa tacaaggcag accttgatga tgaaaaacct ctgggtgtcc     1320
gagagaggtc acttacttgc tgctgcttgt gggcatttaa aacgaggaag atgcacacca     1380
tgtacaagaa accagacacc cagacaatag tgaaggtgcc ttcagagttt aactcgttcg     1440
tcatcccgag cctatggtct acaggcctcg caatcccagt cagatcacgc attaagatgc     1500
```

```
ttttggccaa gaagaccaag cgagagttaa tacctgttct cgacgcgtcg tcagccaggg    1560
atgctgaaca agaggagaag gagaggttgg aggccgagct gactagagaa gccttaccac    1620
ccctcgtccc catcgcgccg gcggagacgg gagtcgtcga cgtcgacgtt gaagaactag    1680
agtatcacgc aggtgcaggg gtcgtggaaa cacctcgcag cgcgttgaaa gtcaccgcac    1740
agccgaacga cgtactacta ggaaattacg tagttctgtc cccgcagacc gtgctcaaga    1800
gctccaagtt ggcccccgtg caccctctag cagagcaggt gaaaataata acacataacg    1860
ggagggccgg ccgttaccag gtcgacggat atgacggcag ggtcctacta ccatgtggat    1920
cggccattcc ggtccctgag tttcaagctt tgagcgagag cgccactatg gtgtacaacg    1980
aaagggagtt cgtcaacagg aaactatacc atattgccgt tcacggaccg tcgctgaaca    2040
ccgacgagga gaactacgag aaagtcagag ctgaaagaac tgacgccgag tacgtgttcg    2100
acgtagataa aaaatgctgc gtcaagagag gaagcgtc gggtttggtg ttggtgggag      2160
agctaaccaa ccccccgttc catgaattcg cctacgaagg gctgaagatc aggccgtcgg    2220
caccatataa gactcagta gtaggagtct ttggggttcc gggatcaggc aagtctgcta     2280
ttattaagag cctcgtgacc aaacacgatc tggtcaccag cggcaagaag gagaactgcc    2340
aggaaatagt taacgacgtg aagaagcacc gcgggaaggg gacaagtagg gaaaacagtg    2400
actccatcct gctaaacggg tgtcgtcgtg ccgtggacat cctatatgtg gacgaggctt    2460
tcgcttgcca ttccggtact ctgctggccc taattgctct tgttaaacct cggagcaaag    2520
tggtgttatg cggagacccc aagcaatgcg gattcttcaa tatgatgcag cttaaggtga    2580
acttcaacca caacatctgc actgaagtat gtcataaaag tatatccaga cgttgcacgc    2640
gtccagtcac ggccatcgtg tctacgttgc actacgagg caagatgcgc acgaccaacc     2700
cgtgcaacaa acccataatc atagacacca caggacagac caagcccaag ccaggagaca    2760
tcgtgttaac atgcttccga ggctgggcaa agcagctgca gttggactac cgtggacacg    2820
aagtcatgac agcagcagca tctcagggcc tcacccgcaa aggggtatac gccgtaaggc    2880
agaaggtgaa tgaaatccc ttgtatgccc ctgcgtcgga gcacgtgaat gtactgctga    2940
cgcgcactga ggataggctg gtgtggaaaa cgctggccgg cgatccctgg attaaggtcc    3000
tatcaaacat tccacagggt aactttacgg ccacattgga agaatggcaa gaagaacacg    3060
acaaaataat gaaggtgatt gaaggaccgg ctgcgcctgt ggacgcgttc cagaacaaag    3120
cgaacgtgtg ttgggcgaaa agcctggtgc ctgtcctgga cactgccgga atcagattga    3180
cagcagagga gtggagcacc ataattacag catttaagga ggacagagct tactctccag    3240
tggtggcctt gaatgaaatt tgcaccaagt actatgagt tgacctggac agtggcctgt    3300
tttctgcccc gaaggtgtcc ctgtattacg agaacaacca ctgggataac agacctggtg    3360
gaaggatgta tggattcaat gccgcaacag ctgccaggct ggaagctaga catacccttcc   3420
tgaaggggca gtggcatacg ggcaagcagg cagttatcgc agaaagaaaa atccaaccgc    3480
tttctgtgct ggacaatgta attcctatca accgcaggct gccgcacgcc ctggtggctg    3540
agtacaagac ggttaaaggc agtagggttg agtggctggt caataaagta agagggtacc    3600
acgtcctgct ggtgagtgag tacaacctgg ctttgcctcg acgcagggtc acttggttgt    3660
caccgctgaa tgtcacaggc gccgataggt gctacgacct aagtttagga ctgccggctg    3720
acgccggcag gttcgacttg gtcttttgtga acattcacac ggaattcaga atccaccact    3780
accagcagtg tgtcgaccac gccatgaagc tgcagatgct tgggggagat gcgctacgac    3840
```

-continued

```
tgctaaaacc cggcggcagc ctcttgatga gagcttacgg atacgccgat aaaatcagcg   3900
aagccgttgt ttcctcctta agcagaaagt tctcgtctgc aagagtgttg cgcccggatt   3960
gtgtcaccag caatacagaa gtgttcttgc tgttctccaa ctttgacaac ggaaagagac   4020
cctctacgct acaccagatg aataccaagc tgagtgccgt gtatgccgga gaagccatgc   4080
acacggccgg gtgtgcacca tcctacagag ttaagagagc agacatagcc acgtgcacag   4140
aagcggctgt ggttaacgca gctaacgccc gtggaactgt aggggatggc gtatgcaggg   4200
ccgtggcgaa gaaatggccg tcagccttta agggagaagc aacaccagtg ggcacaatta   4260
aaacagtcat gtgcggctcg tacccccgtca tccacgctgt agcgcctaat ttctctgcca   4320
cgactgaagc ggaaggggac cgcgaattgg ccgctgtcta ccgggcagtg gccgccgaag   4380
taaacagact gtcactgagc agcgtagcca tcccgctgct gtccacagga gtgttcagcg   4440
gcggaagaga taggctgcag caatccctca accatctatt cacagcaatg gacgccacgg   4500
acgctgacgt gaccatctac tgcagagaca aagttgggga agagaaaatc caggaagcca   4560
tagacatgag gacggctgtg gagttgctca atgatgacgt ggagctgacc acagacttgg   4620
tgagagtgca cccggacagc agcctggtgg gtcgtaaggg ctacagtacc actgacgggt   4680
cgctgtactc gtactttgaa ggtacgaaat tcaaccaggc tgctattgat atggcagaga   4740
tactgacgtt gtgccccaga ctgcaagagg caaacgaaca gatatgccta tacgcgctgg   4800
gcgaaacaat ggacaacatc agatccaaat gtccggtgaa cgattccgat tcatcaacac   4860
ctcccaggac agtgccctgc ctgtgccgct acgcaatgac agcagaacgg atcgcccgcc   4920
ttaggtcaca ccaagttaaa agcatggtgg tttgctcatc ttttcccctc ccgaaatacc   4980
atgtagatgg ggtgcagaag gtaaagtgcg agaaggttct cctgttcgac ccgacggtac   5040
cttcagtggt tagtccgcgg aagtatgccg catctacgac ggaccactca gatcggtcgt   5100
tacgagggtt tgacttggac tggaccaccg actcgtcttc cactgccagc gataccatgt   5160
cgctacccag tttgcagtcg tgtgacatcg actcgatcta cgagccaatg gctcccatag   5220
tagtgacggc tgacgtacac cctgaacccg caggcatcgc ggacctggcg gcagatgtgc   5280
accctgaacc cgcagaccat gtggacctcg agaacccgat tcctccaccg cgcccgaaga   5340
gagctgcata ccttgcctcc cgcgcggcg agcgaccggt gccggcgccg agaaagccga   5400
cgcctgcccc aaggactgcg tttaggaaca agctgccttt gacgttcggc gactttgacg   5460
agcacgaggt cgatgcgttg gcctccggga ttactttcgg agacttcgac gacgtcctgc   5520
gactaggccg cgcgggtgca tatattttct cctcggacac tggcagcgga catttacaac   5580
aaaaatccgt taggcagcac aatctccagt gcgcacaact ggatgcggtc caggaggaga   5640
aaatgtaccc gccaaaattg gatactgaga gggagaagct gttgctgctg aaaatgcaga   5700
tgcacccatc ggaggctaat aagagtcgat accagtctcg caaagtggag aacatgaaag   5760
ccacggtggt ggacaggctc acatcggggg ccagattgta cacgggagcg gacgtaggcc   5820
gcataccaac atacgcggtt cggtaccccc gccccgtgta ctcccctacc gtgatcgaaa   5880
gattctcaag ccccgatgta gcaatcgcag cgtgcaacga atacctatcc agaaattacc   5940
caacagtggc gtcgtaccag ataacagatg aatacgacgc atacttggac atggttgacg   6000
ggtcggatag ttgcttggac agagcgacat tctgcccggc gaagctccgg tgctacccga   6060
aacatcatgc gtaccaccag ccgactgtac gcagtgccgt cccgtcaccc tttcagaaca   6120
cactacagaa cgtgctagcg gccgccacca agagaaactg caacgtcacg caaatgcgag   6180
aactacccac catggactcg gcagtgttca acgtggagtg cttcaagcgc tatgcctgct   6240
```

-continued ccggagaata ttgggaagaa tatgctaaac aacctatccg gataaccact gagaacatca 6300
ctacctatgt gaccaaattg aaaggcccga aagctgctgc cttgttcgct aagacccaca 6360
acttggttcc gctgcaggag gttcccatgg acagattcac ggtcgacatg aaacgagatg 6420
tcaaagtcac tccagggacg aaacacacag aggaaagacc caaagtccag gtaattcaag 6480
cagcggagcc attggcgacc gcttacctgt gcggcatcca cagggaatta gtaaggagac 6540
taaatgctgt gttacgccct aacgtgcaca cattgtttga tatgtcggcc gaagactttg 6600
acgcgatcat cgcctctcac ttccacccag gagacccggt tctagagacg gacattgcat 6660
cattcgacaa aagccaggac gactccttgg ctcttacagg tttaatgatc ctcgaagatc 6720
taggggtgga tcagtacctg ctggacttga tcgaggcagc ctttggggaa atatccagct 6780
gtcacctacc aactggcacg cgcttcaagt tcggagctat gatgaaatcg ggcatgtttc 6840
tgactttgtt tattaacact gttttgaaca tcaccatagc aagcagggta ctggagcaga 6900
gactcactga ctccgcctgt gcggccttca tcggcgacga caacatcgtt cacggagtga 6960
tctccgacaa gctgatggcg gagaggtgcg cgtcgtgggt caacatggag gtgaagatca 7020
ttgacgctgt catgggcgaa aaacccccat atttttgtgg gggattcata gtttttgaca 7080
gcgtcacaca gaccgcctgc cgtgtttcag acccacttaa gcgcctgttc aagttgggta 7140
agccgctaac agctgaagac aagcaggacg aagacaggcg acgagcactg agtgacgagg 7200
ttagcaagtg gttccggaca ggcttggggg ccgaactgga ggtggcacta acatctaggt 7260
atgaggtaga gggctgcaaa agtatcctca tagccatggc caccttggcg agggacatta 7320
aggcgtttaa gaaattgaga ggacctgtta tacacctcta cggcggtcct agattggtgc 7380
gttaatacac agaattctga ttggatcccg gg 7412

<210> SEQ ID NO 4
<211> LENGTH: 7521
<212> TYPE: DNA
<213> ORGANISM: Semliki Forest Virus (SFV)

<400> SEQUENCE: 4
gatggcggat gtgtgacata cacgacgcca aaagattttg ttccagctcc tgccacctcc 60
gctacgcgag agattaacca cccacgatgg ccgccaaagt gcatgttgat attgaggctg 120
acagcccatt catcaagtct ttgcagaagg catttccgtc gttcgaggtg gagtcattgc 180
aggtcacacc aaatgaccat gcaaatgcca gagcattttc gcacctggct accaaattga 240
tcgagcagga gactgacaaa gacacactca tcttggatat cggcagtgcg ccttccagga 300
gaatgatgtc tacgcacaaa taccactgcg tatgccctat gcgcagcgca gaagaccccg 360
aaaggctcga tagctacgca aagaaactgg cagcggcctc cgggaaggtg ctggatagag 420
agatcgcagg aaaaatcacc gacctgcaga ccgtcatggc tacgccagac gctgaatctc 480
ctaccttttg cctgcataca gacgtcacgt gtcgtacggc agccgaagtg gccgtatacc 540
aggacgtgta tgctgtacat gcaccaacat cgctgtacca tcaggcgatg aaaggtgtca 600
gaacggcgta ttggattggg tttgacacca ccccgtttat gtttgacgcg ctagcaggcg 660
cgtatccaac ctacgccaca aactgggccg acgagcaggt gttacaggcc aggaacatag 720
gactgtgtgc agcatccttg actgagggaa gactcggcaa actgtccatt ctccgcaaga 780
agcaattgaa accttgcgac acagtcatgt tctcggtagg atctacattg tacactgaga 840
gcagaaagct actgaggagc tggcacttac cctccgtatt ccacctgaaa ggtaaacaat 900

```
cctttacctg taggtgcgat accatcgtat catgtgaagg gtacgtagtt aagaaaatca    960
ctatgtgccc cggcctgtac ggtaaaacgg tagggtacgc cgtgacgtat cacgcggagg   1020
gattcctagt gtgcaagacc acagacactg tcaaaggaga aagagtctca ttccctgtat   1080
gcacctacgt cccctcaacc atctgtgatc aaatgactgg catactagcg accgacgtca   1140
caccggagga cgcacagaag ttgttagtgg gattgaatca gaggatagtt gtgaacggaa   1200
gaacacagcg aaacactaac acgatgaaga actatctgct tccgattgtg gccgtcgcat   1260
ttagcaagtg ggcgagggaa tacaaggcag accttgatga tgaaaaacct ctgggtgtcc   1320
gagagaggtc acttacttgc tgctgcttgt gggcatttaa aacgaggaag atgcacacca   1380
tgtacaagaa accagacacc cagacaatag tgaaggtgcc ttcagagttt aactcgttcg   1440
tcatcccgag cctatggtct acaggcctcg caatcccagt cagatcacgc attaagatgc   1500
ttttggccaa gaagaccaag cgagagttaa tacctgttct cgacgcgtcg tcagccaggg   1560
atgctgaaca agaggagaag gagaggttgg aggccgagct gactagagaa gccttaccac   1620
ccctcgtccc catcgcgccg gcggagacgg gagtcgtcga cgtcgacgtt gaagaactag   1680
agtatcacgc aggtgcaggg gtcgtggaaa cacctcgcag cgcgttgaaa gtcaccgcac   1740
agccgaacga cgtactacta ggaaattacg tagttctgtc cccgcagacc gtgctcaaga   1800
gctccaagtt ggccccgtg caccctctag cagagcaggt gaaaataata acacataacg   1860
ggagggccgg cggttaccag gtcgacggat atgacggcag ggtcctacta ccatgtggat   1920
cggccattcc ggtccctgag tttcaagctt tgagcgagag cgccactatg gtgtacaacg   1980
aaagggagtt cgtcaacagg aaactatacc atattgccgt tcacggaccg tcgctgaaca   2040
ccgacgagga gaactacgag aaagtcgagg ctgaaagaac tgacgccgag tacgtgttcg   2100
acgtagataa aaaatgctgc gtcaagagag aggaagcgtc gggtttggtg ttggtgggag   2160
agctaaccaa cccccccgttc catgaattcg cctacgaagg gctgaagatc aggccgtcgg   2220
caccatataa gactacagta gtaggagtct ttgggggttcc gggatcaggc aagtctgcta   2280
ttattaagag cctcgtgacc aaacacgatc tggtcaccag cggcaagaag gagaactgcc   2340
aggaaatagt taacgacgtg aagaagcacc gcgggaaggg gacaagtagg gaaaacagtg   2400
actccatcct gctaaacggg tgtcgtcgtg ccgtggacat cctatatgtg gacgaggctt   2460
tcgcttgcca ttccggtact ctgctggccc taattgctct tgttaaacct cggagcaaag   2520
tggtgttatg cggagacccc aagcaatgcg gattcttcaa tatgatgcag cttaaggtga   2580
acttcaacca caacatctgc actgaagtat gtcataaaag tatatccaga cgttgcacgc   2640
gtccagtcac ggccatcgtg tctacgttgc actacggagg caagatgcgc acgaccaacc   2700
cgtgcaacaa acccataatc atagacacca caggacagac caagcccaag ccaggagaca   2760
tcgtgttaac atgcttccga ggctgggcaa agcagctgca gttggactac cgtggacacg   2820
aagtcatgac agcagcagca tctcagggcc tcacccgcaa aggggtatac gccgtaaggc   2880
agaaggtgaa tgaaaatccc ttgtatgccc ctgcgtcgga gcacgtgaat gtactgctga   2940
cgcgcactga ggataggctg gtgtggaaaa cgctggccgg cgatccctgg attaaggtcc   3000
tatcaaacat tccacagggt aactttacgg ccacattgga agaatggcaa gaagaacacg   3060
acaaaataat gaaggtgatt gaaggaccgg ctgcgcctgt ggacgcgttc cagaacaaag   3120
cgaacgtgtg ttgggcgaaa gcctggtgc ctgtcctgga cactgccgga atcagattga   3180
cagcagagga gtgagcacc ataattacag catttaagga ggacagagct tactctccag   3240
tggtggcctt gaatgaaatt tgcaccaagt actatggagt tgacctggac agtggcctgt   3300
```

-continued

```
tttctgcccc gaaggtgtcc ctgtattacg agaacaacca ctgggataac agacctggtg    3360
gaaggatgta tggattcaat gccgcaacag ctgccaggct ggaagctaga catacct tcc    3420
tgaaggggca gtggcatacg ggcaagcagg cagttatcgc agaaagaaaa atccaaccgc    3480
tttctgtgct ggacaatgta attcctatca accgcaggct gccgcacgcc ctggtggctg    3540
agtacaagac ggttaaaggc agtagggttg agtggctggt caataaagta agagggtacc    3600
acgtcctgct ggtgagtgag tacaacctgg ctttgcctcg acgcagggtc acttggttgt    3660
caccgctgaa tgtcacaggc gccgataggt gctacgacct aagtttagga ctgccggctg    3720
acgccggcag gttcgacttg gtctttgtga acattcacac ggaattcaga atccaccact    3780
accagcagtg tgtcgaccac gccatgaagc tgcagatgct tggggagat gcgctacgac     3840
tgctaaaacc cggcggcatc ttgatgagag cttacggata cgccgataaa atcagcgaag    3900
ccgttgtttc ctccttaagc agaaagttct cgtctgcaag agtgttgcgc ccggattgtg    3960
tcaccagcaa tacagaagtg ttcttgctgt ctccaacttt gacaacgga aagagaccct     4020
ctacgctaca ccagatgaat accaagctga gtgccgtgta tgccggagaa gccatgcaca    4080
cggccgggtg tgcaccatcc tacagagtta agagagcaga catagccacg tgcacagaag    4140
cggctgtggt taacgcagct aacgcccgtg gaactgtagg ggatggcgta tgcagggccg    4200
tggcgaagaa atggccgtca gccttttaagg gagcagcaac accagtgggc acaattaaaa    4260
cagtcatgtg cggctcgtac cccgtcatcc acgctgtagc gcctaatttc tctgccacga    4320
ctgaagcgga aggggaccgc gaattggccg ctgtctaccg ggcagtggcc gccgaagtaa    4380
acagactgtc actgagcagc gtagccatcc cgctgctgtc cacaggagtg ttcagcggcg    4440
gaagagatag gctgcagcaa tccctcaacc atctattcac agcaatggac gccacggacg    4500
ctgacgtgac catctactgc agagacaaaa gttgggagaa gaaaatccag gaagccattg    4560
acatgaggac ggctgtggag ttgctcaatg atgacgtgga gctgaccaca gacttggtga    4620
gagtgcaccc ggacagcagc ctggtgggtc gtaagggcta cagtaccact gacgggtcgc    4680
tgtactcgta ctttgaaggt acgaaattca accaggctgc tattgatatg cagagatac     4740
tgacgttgtg gccagactg caagaggcaa acgaacagat atgcctatac gcgctgggcg     4800
aaacaatgga caacatcaga tccaaatgtc cggtgaacga ttccgattca tcaacacctc    4860
ccaggacagt gccctgcctg tgccgctacg caatgacagc agaacggatc gcccgcctta    4920
ggtcacacca agttaaaagc atggtggttt gctcatcttt tccctcccg aaataccatg     4980
tagatggggt gcagaaggta aagtgcgaga aggttctcct gttcgacccg acggtacctt    5040
cagtggttag tccgcggaag tatgccgcat ctacgacgga ccactcagat cggtcgttac    5100
gagggtttga cttggactgg accaccgact cgtcttccac tgccagcgat accatgtcgc    5160
tacccagttt gcagtcgtgt gacatcgact cgatctacga gccaatggct cccatagtag    5220
tgacggctga cgtacaccct gaacccgcag gcatcgcgga cctgcggca gatgtgcacc     5280
ctgaacccgc agaccatgtg gacctcgaga acccgattcc tccaccgcgc ccgaagagag    5340
ctgcatacct tgcctcccgc gcggcggagc gaccggtgcc ggcgccgaga agccgacgc     5400
ctgccccaag gactgcgttt aggaacaagc tgccttttgac gttcggcgac tttgacgagc    5460
acgaggtcga tgcgttggcc tccgggatta ctttcggaga cttcgacgac gtcctgcgac    5520
taggccgcgc gggtgcatat atttctcct cggacactgg cagcggacat ttacaacaaa     5580
aatccgttag gcagcacaat ctccagtgcg cacaactgga tgcggtccag gaggagaaaa    5640
```

-continued

```
tgtacccgcc aaaattggat actgagaggg agaagctgtt gctgctgaaa atgcagatgc    5700
acccatcgga ggctaataag agtcgatacc agtctcgcaa agtggagaac atgaaagcca    5760
cggtggtgga caggctcaca tcggggcca gattgtacac gggagcggac gtaggccgca     5820
taccaacata cgcggttcgg tacccccgcc ccgtgtactc ccctaccgtg atcgaaagat    5880
tctcaagccc cgatgtagca atcgcagcgt gcaacgaata cctatccaga aattacccaa    5940
cagtggcgtc gtaccagata acagatgaat acgacgcata cttggacatg gttgacgggt    6000
cggatagttg cttggacaga gcgacattct gcccggcgaa gctccggtgc tacccgaaac    6060
atcatgcgta ccaccagccg actgtacgca gtgccgtccc gtcacccttt cagaacacac    6120
tacagaacgt gctagcggcc gccaccaaga gaaactgcaa cgtcacgcaa atgcgagaac    6180
tacccaccat ggactcggca gtgttcaacg tggagtgctt caagcgctat gcctgctccg    6240
gagaatattg ggaagaatat gctaaacaac ctatccggat aaccactgag aacatcacta    6300
cctatgtgac caaattgaaa ggcccgaaag ctgctgcctt gttcgctaag acccacaact    6360
tggttccgct gcaggaggtt cccatggaca gattcacggt cgacatgaaa cgagatgtca    6420
aagtcactcc agggacgaaa cacacagagg aaagacccaa agtccaggta attcaagcag    6480
cggagccatt ggcgaccgct tacctgtgcg gcatccacag ggaattagta aggagactaa    6540
atgctgtgtt acgccctaac gtgcacacat tgtttgatat gtcggccgaa gacttttgacg    6600 cgatcatcgc ctctcacttc cacccaggag accggttct agagacggac attgcatcat    6660
tcgacaaaag ccaggacgac tccttggctc ttacaggttt aatgatcctc gaagatctag    6720
gggtggatca gtacctgctg gacttgatcg aggcagcctt tggggaaata tccagctgtc    6780
acctaccaac tggcacgcgc ttcaagttcg gagctatgat gaaatcgggc atgtttctga    6840
cttttgttta taacactgtt ttgaacatca ccatagcaag cagggtactg gagcagagac    6900
tcactgactc cgcctgtgcg gccttcatcg gcgacgacaa catcgttcac ggagtgatct    6960
ccgacaagct gatggcggag aggtgcgcgt cgtgggtcaa catggaggtg aagatcattg    7020
acgctgtcat gggcgaaaaa ccccccatatt tttgtggggg attcatagtt tttgacagcg    7080
tcacacagac cgcctgccgt gtttcagacc cacttaagcg cctgttcaag ttgggtaagc    7140
cgctaacagc tgaagacaag caggacgaag acaggcgacg agcactgagt gacgaggtta    7200
gcaagtggtt ccggacaggc ttgggggccg aactggaggt ggcactaaca tctaggtatg    7260
aggtagaggg ctgcaaaagt atcctcatag ccatggccac cttggcgagg gacattaagg    7320
cgtttaagaa attgagagga cctgttatac acctctacgg cggtcctaga ttggtgcgtt    7380
aatacacaga attctgatta tagcgcacta ttatagcacc atgaattaca tccctacgca    7440
aacgttttac ggccgccgt ggcgcccgcg cccggcggcc cgtccttggc cgttgcaggc    7500
cactccggtg gctcccgtcg t                                              7521
```

<210> SEQ ID NO 5
<211> LENGTH: 841
<212> TYPE: DNA
<213> ORGANISM: Semliki Forest Virus (SFV)

<400> SEQUENCE: 5

```
attacatccc tacgcaaacg ttttacggcc gccggtggcg cccgcgcccg gcggcccgtc      60
cttggccgtt gcaggccact ccggtggctc ccgtcgtccc cgacttccag gcccagcaga     120
tgcagcaact catcagcgcc gtaaatgcgc tgacaatgag acagaacgca attgctcctg     180
ctaggcctcc caaaccaaag aagaagaaga caaccaaacc aaagccgaaa acgcagccca     240
```

-continued

```
agaagatcaa cggaaaaacg cagcagcaaa agaagaaaga caagcaagcc gacaagaaga    300
agaagaaacc cggaaaaaga gaaagaatgt gcatgaagat tgaaaatgac tgtatcttcg    360
tatgcggcta gccacagtaa cgtagtgttt ccagacatgt cgggcaccgc actatcatgg    420
gtgcagaaaa tctcgggtgg tctggggggcc ttcgcaatcg gcgctatcct ggtgctggtt   480
gtggtcactt gcattgggct ccgcagataa gttagggtag gcaatggcat tgatatagca    540
agaaaattga aaacagaaaa agttagggta agcaatggca tataaccata actgtataac    600
ttgtaacaaa gcgcaacaag acctgcgcaa ttggccccgt ggtccgcctc acggaaactc    660
ggggcaactc atattgacac attaattggc aataattgga agcttacata agcttaattc    720
gacgaataat tggatttttta ttttattttg caattggttt ttaatatttc caaaaaaaaa   780
aaaaaaaaaa aaaaaaaaaa aaaaaaaaaa aaaaaaaaaa aaaaaaaaaa aaaaaaaaaa    840
a                                                                   841

<210> SEQ ID NO 6
<211> LENGTH: 260
<212> TYPE: DNA
<213> ORGANISM: SV40 Virus

<400> SEQUENCE: 6
agagtcgggg cggccggccg cttcgagcag acatgataag atacattgat gagtttggac     60
aaaccacaac tagaatgcag tgaaaaaaat gctttatttg tgaaatttgt gatgctattg    120
ctttatttgt aaccattata agctgcaata acaagttaa caacaacaat tgcattcatt     180
ttatgtttca ggttcagggg gaggtgtggg aggttttta aagcaagtaa aacctctaca    240
aatgtggtaa aatcgataag                                                260

<210> SEQ ID NO 7
<211> LENGTH: 940
<212> TYPE: DNA
<213> ORGANISM: Homo sapiens

<400> SEQUENCE: 7
aattcgcctg tcatacagct aataattgac cataagacaa ttagatttaa attagttttg     60
aatctttcta ataccaaagt tcagtttact gttccatgtt gcttctgagt ggcttcacag    120
acttatgaaa aagtaaacgg aatcagaatt acatcaatgc aaaagcattg ctgtgaactc    180
tgtacttagg actaaacttt gagcaataac acacatagat tgaggattgt ttgctgttag    240
catacaaact ctggttcaaa gctcctcttt attgcttgtc ttggaaaatt tgctgttctt    300
catggtttct cttttcactg ctatctattt ttctcaacca ctcacatggc tacaataact    360
gtctgcaagc ttatgattcc caaatatcta tctctagcct caatcttgtt ccagaagata    420
aaaagtagta ttcaaatgca catcaacgtc tccacttgga gggcttaaag acgtttcaac    480
atacaaaccg gggagttttg cctggaatgt ttcctaaaat gtgtcctgta gcacataggg    540
tcctcttgtt cctaaaaatc taattacttt tagcccagtg ctcatcccac ctatggggag    600
atgagagtga aagggagcc tgattaataa ttacactaag tcaataggca tagagccagg    660
actgtttggg taaactggtc actttatctt aaactaaata tatccaaaac tgaacatgta    720
cttagttact aagtctttga ctttatctca ttcataccac tcagctttat ccaggccact    780
tatttgacag tctagctagc ccctagagatt tctgccccaa agagctctgt gtccttgaac    840
ataaaataca aataaccgct atgctgttaa ttattggcaa atgtcccatt ttcaacctaa    900
```

```
ggaaatacca taaagtaaca gatataccaa caaaaggtta                            940
```

<210> SEQ ID NO 8
<211> LENGTH: 28892
<212> TYPE: DNA
<213> ORGANISM: Chimeric
<220> FEATURE:
<221> NAME/KEY: 5'ITR
<222> LOCATION: (1)..(438)
<223> OTHER INFORMATION: First inverted terminal sequence and signal
      sequence for packaging
<220> FEATURE:
<221> NAME/KEY: Stuffer
<222> LOCATION: (439)..(10990)
<223> OTHER INFORMATION: First non-encoding stuffer sequence
<220> FEATURE:
<221> NAME/KEY: AFP(p+e)
<222> LOCATION: (10991)..(11930)
<223> OTHER INFORMATION: Alpha-fetoprotein (AFP) promoter.  Includes
      promter region (p) and enhancer region (e)
<220> FEATURE:
<221> NAME/KEY: SFV
<222> LOCATION: (12257)..(19366)
<223> OTHER INFORMATION: SFV replicon sequence region
<220> FEATURE:
<221> NAME/KEY: mIL-12
<222> LOCATION: (19389)..(21722)
<223> OTHER INFORMATION: Mouse Interleukin-12 (IL-12) gene sequence
      (exogenous gene)
<220> FEATURE:
<221> NAME/KEY: PolyA
<222> LOCATION: (22621)..(22880)
<223> OTHER INFORMATION: Polyadenylation sequence derived from SV40
      virus
<220> FEATURE:
<221> NAME/KEY: Stuffer
<222> LOCATION: (22881)..(28731)
<223> OTHER INFORMATION: Second stuffer non-encoding sequence
<220> FEATURE:
<221> NAME/KEY: 3'ITR
<222> LOCATION: (28732)..(28892)
<223> OTHER INFORMATION: Second inverted terminal repeat sequence

<400> SEQUENCE: 8

```
aaacatcatc aataatatac cttatttgg attgaagcca atatgataat gaggggtgg       60 agtttgtgac gtggcgcggg gcgtgggaac ggggcgggtg acgtagtagt gtggcggaag    120
tgtgatgttg caagtgtggc ggaacacatg taagcgacgg atgtggcaaa agtgacgttt    180
ttggtgtgcg ccggtgtaca caggaagtga caattttcgc gcggttttag gcggatgttg    240
tagtaaattt gggcgtaacc gagtaagatt tggccatttt cgcggaaaa ctgaataaga    300 ggaagtgaaa tctgaataat tttgtgttac tcatagcgcg taatatttgt ctagggccgc    360
ggggactttg accgtttacg tggagactcg cccaggtgtt tttctcaggt gttttccgcg    420
ttccgggtca agttggcgt tttgatatca agcttatcga taccgtcaaa caagtcttta    480
attcaagcaa gactttaaca agttaaaagg agcttatggg taggaagtag tgttatgatg    540
tatgggcata aagggtttta atgggatagt gaaaatgtct ataataatac ttaaatggct    600
gcccaatcac ctacaggatt gatgtaaaca tggaaaaggt caaaaacttg ggtcactaaa    660
atagatgatt aatggagagg atgaggttga tagttaaatg tagataagtg gtcttattct    720
caataaaaat gtgaacataa ggcgagtttc tacaaagatg acaggactc attcatgaaa    780 cagcaaaaac tggacatttg ttctaatctt tgaagatgtat gaaaaattcc tattttaaag    840
gtaaaacagt aactcacagg aaataccaac ccaacataaa atcagaaaca atagtctaaa    900
gtaataaaaa tcaaacgttt gcacgatcaa attatgaatg aaattcacta ctaaaattca    960
cactgatttt gtttcatcca cagtgtcaat gttgtgatgc atttcaattg tgtgacacag   1020
```

```
gcagactgtg gatcaaaagt ggtttctggt gcgacttact ctcttgagta tacctgcagt    1080
cccctttctt aagtgtgtta aaaaaaaagg gggatttctt caattcgcca atactctagc    1140
tctccatgtg ctttctagga aacaagtgtt aacccacctt atttgtcaaa cctagctcca    1200
aaggactttt gactccccac aaaccgatgt agctcaagag agggtatctg tcaccagtat    1260
gtatagtgaa aaaagtatcc caagtcccaa cagcaattcc taaaaggagt ttatttaaaa    1320
aaccacacac acctgtaaaa taagtatata tcctccaagg tgactagttt taaaaaaaca    1380
gtattggctt tgatgtaaag tactagtgaa tatgttagaa aaatctcact gtaaccaagt    1440
gaaatgaaag caagtatggt ttgcagagat tcaaagaaaa tataagaaaa cctactgttg    1500
ccactaaaaa gaatcatata ttaaatatac tcacacaata gctcttcagt ctgataaaat    1560
ctacagtcat aggaatggat ctatcactat ttctattcag tgctttgatg taatccagca    1620
ggtcagcaaa gaatttatag ccccccttga gcacacagag ggctacaatg tgatggcctc    1680
ccatctcctt catcacatct cgagcaagac gttcagtcct acagaaataa aatcaggaat    1740
ttaatagaaa gtttcataca ttaaacttta taacaaacac ctcttagtca ttaaacttcc    1800
acaccaacct gggcaatata gtgagacccc atgcctgcaa aaaaaaaaaa attagccagg    1860
catggtagca tgtacctgta gtcccagcta cttgagaggt gaggtgggaa atcactttta    1920
gtgcaggatg ttgaggctgg agtgaactgt gattgtgcca ctgcactcca gcctggacaa    1980
tagagcaaga ccttgtctca aaaaaatgca ttaaaaattt ttttttaaatc ttccacgtat    2040 cacatccttt gccctcatgt ttcataaggt aaaaaatttg ataccttcaa aaaaaccaag    2100
cataccacta tcataatttt ttttaaatgc aaataaaaac aagataccat tttcacctat    2160
cagactggca ggttctgatt aaatgaaatt ttctggataa tatacaatat taagagagac    2220
tgtagaaact gggccagtgg ctcatgcctg taatcccagc actttgggag gctgggtaac    2280
atggcgaacc ctgtttctac aaaataaaaa tattagctgg gagtggtggc gcacacctat    2340
agtcccagct actcaggagg ctgaggtgga aggatcgctt gaacccagga ggttgagact    2400
gcagtgaact gtgatcattc tgctgcactg caccccagcc tgggcaacag agaccttgtc    2460
tcaaaaaaaa aaaaaaaaga gacaaattgt gaagagaaag gtactctcat ataacatcag    2520
gagtataaaa tgattcaact tcttagagga aaatttggca ataccaaaat attcaataaa    2580
ctctttcccc ttgacccaga aattccactt gaataaagct gaacaagtac caaacatgta    2640
aaagaatgtt tcttctagta cagtcggtaa gaacaaaata gtgtctatca atagtggact    2700
ggttaaatca gttatggtat ctccataaga cagaatgcta tgcaaccttt aaaatatatt    2760
agatagctct agacacacta atattaaaag tgtccaataa catttaaaac tatactcata    2820
cgttaaaata taaatgtata tatgtacttt tgcatatagt atacatgcat aggccagtgc    2880
ttgagaagaa atgtgtacag aaggctgaaa ggagagaact ttagtcttct tgtttatggc    2940
ctccatagtt agaatatttt ataacacaaa tattttgata ttataatttt aaaataaaaa    3000
cacagaatag ccagacatac aatgcaagca ttcaatacca ggtaaggttt ttcactgtaa    3060
ttgacttaac agaaaatttt caagctagat gtgcataata ataaaaatct gaccttgcct    3120
tcatgtgatt cagccccagt ccattaccct gtttaggact gagaaatgca agactctggc    3180
tagagttcct tcttccatct cccttcaatg tttactttgt tctggtccct acagagtccc    3240
actataccac aactgatact aagtaattag taaggccctc ctcttttatt tttaataaag    3300 aagatttag aaagcatcag ttatttaata agttggccta gttatgttc aaatagcaag    3360
```

```
tactcagaac agctgctgat gtttgaaatt aacacaagaa aaagtaaaaa acctcatttt    3420
aagatcttac ttacctgtcc ataattagtc catgaggaat aaacaccctt tccaaatcct    3480
cagcataatg attaggtatg caaaataaat caaggtcata acctggttca tcatcactaa    3540
tctgaaaaag aaatatagct gtttcaatga gagcattaca ggatacaaac atttgattgg    3600
attaagatgt taaaaaataa ccttagtcta tcagagaaat ttaggtgtaa gatgatatta    3660
gtaactgtta actttgtagg tatgataatg aattatgtaa gaaaacaaca ggccgggcgg    3720
gttggttcac acgtgtaatc ccagcacttt gggaggctga ggcaggcaga ctgcctgagc    3780
tcaggagttc gagaccagcc tgggcaacac ggtgaaatcc cgtctctact aaaaatacaa    3840
aaaaattagc cgggtgtggt gacacatgcc tgtagtccca gctacttggg aggctgaggc    3900
aggagaatca cttgaacctg ggaggtgaag gttgcagtga gccaagatgg caccacttca    3960
ctccagcctg ggaaacagag caagactctg tctctgagct gagatggcac cacttcactc    4020
cagcctggga aacagagcaa gactctgtct caaaaaaaac aaaacacaca aacaaaaaaa    4080
caggctgggc gcggtggctc acgcctgtaa tcccagcact ttgggaggcc gaggcgggtg    4140
gatcacctga ggtcaggagt tccagaccag ccttgtcaac atggtgaaac ctccccccgc    4200
cgtctctact aaaaatacaa aaattagcca ggcgtggtgg caggagcctg taatcccagc    4260
tacttgggag gctgaggcag gagaatcgct tgtacccaga aggcagaggt tgcactgagc    4320
tgagatggca ccattgcact ccagcctggg ggacaagagc gagatttcgt ctttaaaaaa    4380
caaaaacaaa acaaaaaacc atgtaactat atgtcttagt catcttagtc aagaatgtag    4440
aagtaaagtg ataagatatg gaatttcctt taggtcacaa agagaaaaag aaaaatttta    4500
aagagctaag acaaacgcag caaaatcttt atatttaata atattctaaa catgggtgat    4560
gaacatacgg gtattcatta tactattctc tccacttttg agtatgtttg aaaatttagt    4620
aaaacaagtt ttaacacact gtagtctaac aagataaaat atcacactga acaggaaaaa    4680
ctggcatggt gtggtggctc acacttgtaa tcccagtgct ttgggaggct gagacaggag    4740
agttgcttga ggccaggagt tcaagaccga catggggaat gtagcaagac cccgtcccta    4800
caaaaaactt tgtaaaaatt tgccaggtat ggtggtgcat acctgtagtc ccagctactc    4860
gggaggcgga ggcagaagga atcacttgag cccaggagtt tgaggctgca gtgagctacg    4920
atcataccac agcactccag cgtggacaac agagtaagac cctatctcaa aaacaaaaca    4980
aaacaaaaca aacaaaaaaa accacaagaa aaactgctgg ctgatgcagc ggctcatgcc    5040
tgtaatccca gtattttggg aggcccaggt gggcgtatca cctgaggtca ggagttagag    5100
accagcctgg ccaacatggt gaaaccccat ctctactaaa aatacaaaat tagccaggca    5160
tgtggcacgc gcctgtagtc ccagttactg ggaggctgaa gcaggaggat cacctgagcc    5220
cgggaggtgg aggttgcagt gagccgagat cacaccactg cactccagcc tgggtgacac    5280
agcaataccc tacctcaaaa taaaaaagaa aagaaaaga aagttgctg tccccgctac    5340 cccaatccca aatccaaaca gcctctctca tctcacagta aggggaaaa atcacccaaa    5400 aaagctaagt gatcttttga aaacccaaac tcttagaagt ctaagattat tatagtcaac    5460
tcatgaagtg tcatcataaa agatactcta atattattta agtagaacca catattggtt    5520
gtcttggtat gtctagcccc tggcatacaa aatatttaat aacactgata tggtacctgt    5580
gatgtgaaaa tgtactatga gtacagcttt ataaatacta tatatgtacc tatatacaga    5640
aaaaaataca acaaaatcat aaaagcactt atctttgaaa gaggagttac agcaatttta    5700
tttagttctt tattgctttg ctatatattc taaattttt tcaatgaata tatatcactt    5760
```

```
ttaaaaaaat tcaatggtct ttcttataaa ttatctttgg cagcatgcgt ttttatatat     5820
acatataaaa tgtatgggaa attttaaag gatacattaa attaaagcaa aatatacaaa      5880
caaaaaatca gaatacaaaa agataaaaag attgggaagg gagggaggga gtaaggagga    5940
agggtgggtg ggtatagaga aatataccaa ataatggtaa gaagtggggt cttgacactt    6000
tctacacttt ttttaaataa aaaaaatttt tttctctctc ttttttttt ttagagacga     6060 agtctcgcta tgttgcccag gctggtcttg aactcctggg atcaagagat cctcctgcct    6120
cagcctccca aggtgcttgg attacaggtg tgagccacca cgcctggtca cttttctacac    6180 tttaatatat atatttttc attttcaatg tcatttttat tagttaattt ataatacccca    6240 ttcaccatta tattcaaagt ctatttgaag aaataaacca gaaagaatga aatactctag    6300
ctcacatgct attcaatact aaattacctt tcaaatcaca ttcaagaagc tgatgattta    6360
agctttggcg gtttccaata aatattggtc aaaccataat taaatctcaa tatatcagtt    6420
agtacctatt gagcatctcc ttttacaacc taagcattgt attaggtgct taaatacaag    6480
cagcttgact tttaatacat ttaaaaatac atatttaaga cttaaaatct tatttatgga    6540
attcagttat attttgaggt ttccagtgct gagaaatttg aggtttgtgc tgtctttcag    6600
tccccaaagc tcagttctga gttctcagac tttggtggaa cttcatgtat tgtcaggttg    6660
gcccgtaata cctgtgggac aacttcagcc cctgtgcaca tggccaggag gctggttgca    6720
aacattttca ggtaggtgga ccaggacatg cccctggtca tggccaggtg gaggcatagt    6780
gctatacagc aggcagaagt caatattgat ttgttttaa agaaacatgt actactttca    6840
taagcagaaa aaatttctat tcttggggga aaagattatg ccagatcctc taggattaaa    6900
tgctgatgca tctgctaaac cttcacatat cagaacatat ttactataga aagaatgaaa    6960
atgggacatt tgtgtgtcac ctatgtgaac attccaaaaa tattttacaa caactaagta   7020 tttttataaat tttatgaact gaaatttagt tcaagttcta ggaaaataca aaccttgcta   7080
gatattataa aaatgataca atatatattc atttcaggct catcagaata tatctgttat    7140
cacttgacaa gaatgaaaat gcaccatttt gtagtgcttt aaaatcagga agatccagag    7200
tactaaaaat gacttcttcc ttgaagctta ctcaccaact tcctcccagt tactcactgc    7260
ttctgccaca agcataaact aggacccagc cagaactccc ttgaaatata cacttgcaac    7320
gattactgca tctatcaaaa tggttcagtg cctggctaca ggttctgcag atcgactaag    7380
aatttgaaaa gtcttgttta tttcaaagga agcccatgtg aattctgccc agagttcatc    7440
ccagatatgc agtctaagaa tacagacaga tcagcagaga tgtattctaa aacaggaatt    7500
ctggcaatat aacaaattga tttccaatca aaacagattt acataccata cttatgtcaa    7560
gaagttgttt tgttttattg catcctagat tttatttttt tgatttatgg tttacttaa    7620 gcataaaaaa tttgtcaata caactcttcc caaaaggcat aaacaaaaat tcataaaact    7680
tgcatcactt gagatacttc aggtatgaat tcacaacttt gttacaactt actatatata    7740
tgcacacata tatatatatt tgggtatatt gggggggttc taatttaaga aatgcataat    7800
tggctataga cagacagttg tcagaacttg gcaatgggta cgtgcaggtt cattatacca    7860
agtctacttg tagttgttca aaatgtatca taatacaagg ccgggcgagg tcgtcacgcc    7920
tgtaatccca gcattttggg aggctaaggc aggaggatt cttgaggtca ggagtttgtg     7980
accagcctgg gcaacagagc aagaccctgt ctccaaaaag aaaaaaaata attttttaca    8040
aaataaaaac aaaatgtatc atcagacgaa attaaataag aggcaattca tttaaatgac    8100
```

```
aacttttccc agcttgacat ttaacaaaaa gtctaagtcc tcttaattca tatttaatga    8160
tcaaatatca aatactaatt tttttttttt tttttttttt gagacggagt ctcgctctgt    8220
cgcccaggct ggagtgcagt ggcgcgatcc tggctcactg caagctccgc ctcccgggtt    8280
cacgccattc tcctgcctca gcctcccgag tagctgggat tacagacatg cgccaccacg    8340
cccggctaat tttgtatttt tagtagagat ggggtttctc catgttggtc aggctggtct    8400
tgaatttccc acctcaggtg atctgcctgc ctcagcctca caaagcagta gctgggacta    8460
caggcaccca ccaccacact tggttaattc ttttgtattt tttttgtaaa gacgggattt    8520
caccatgtta gccaggatgg tctcgatctc ctgatctcat gatccgcccg cctcagcctc    8580
ccaaagtgct gggattacag gcgtgagcca ccccgcccgg ccatcaaata ctaattctta    8640
aatggtaagg acccactatt cagaacctgt atccttatca ctaatatgca aatatttatt    8700
gaatacttac tatgtcatgc atactagaga gagttagata aatttgatac agctaccctc    8760
acagaactta cagtgtaata gatggcatga catgtacatg agtaactgtg aacagtgtta    8820
aattgctatt taaaaaaaaa gacggctggg cgctgtggct catgcctgta atcccagcac    8880
tttgggaggc caaggcaagt tgatcgctcg aggtcaagag ttcgagacca gcctggccaa    8940
cgtggtaaaa ccccgtctct actaaaaata caaaaaaaaa attagccagg catggtggca    9000
caggcctgta atcccagcta ctagggaggc tgagacatgg agaactgctt gaatccagga    9060
ggcagaggtt acagtgagcc gagatcatac cactcactc cagcctgagt gacagagcga    9120
gactcctgtc taaaaaaaaa aaaaaaaaaa aagatacagg ttaagtgtta tggtagttga    9180
agagagaact caaactctgt ctcagaagcc tcacttgcat gtggaccact gatatgaaat    9240
aatataaata ggtataattc aataaatagg aacttcagtt ttaatcatcc caaacaccaa    9300
aacttcctat caaacaggtc caataaactc aatctctata agagctagac agaaatctac    9360
ttggtggcct ataatcttat tagcccttac ttgtcccatc tgatattaat taacccccatc    9420 taatatggat tagttaacaa tccagtggct gctttgacag gaacagttgg agagagttgg    9480
ggattgcaac atattcaatt atacaaaaat gcattcagca tctaccttga ttaaggcagt    9540
gtgcaacaga atttgcagga gagtaaaaga atgattataa atttacaacc cttaaagagc    9600
tatagctggg cgtggtggct catgcctgta aatcccagca cttttgggagg ctgaggcggg    9660 tggatcacct gaggccagaa gttcaagacc agcctagcca acatggcgaa accctgtctc    9720
tacaaaaaat acaaaaatta gccgggtgtg gtggcacgtg cctgtagtcc cagttacttg    9780
ggaggccgag gcaggagaat cgcttgaacc taggaggtgg aggctgcagt gagccgagat    9840
tgtgccactg cactccactt cagcctgggc gacaagagca agactccgtc acaaaaaaaa    9900
aaaaaaaaaa aaagcttaaa atctagtggg aaaggcatat atacatacaa ctaactgtat    9960
agcataataa agctcataat ctgtaacaaa atctaattcg acaagcccag aaacttgtga   10020
tttaccaaaa acagttatat atacacaaaa agtaaaccta gaacccaaag ttacccagca   10080
ccaatgattc tctccctaag cagtatcaag tttaaagcag tgattacatt ctactgccta   10140
gattgtaaac tgagtaaagg agaccagcac ctttctgcta ctgaactagc acagccgtgt   10200
aaaccaacaa ggcaatggca gtgcccaact ttctgtatga atataagtta catctgtttt   10260
attatttgtg acttggtgtt gcatgtggtt attatcaaca ccttctgaaa gaacaactac   10320
ctgctcaggc tgccataaca aaataccaca gactgagtga cttaacagaa acttatttct   10380
cacagttttg gaggctggga agtccaaaat taaggtacct gcaaggtagg tttcaatctc   10440
aggcctcttc tttggcttga aggtcttcta actgtgtgct cacatgacct cttctaacaa   10500
```

```
gctctctggt gtctcttttt ttttttttt cttttttgag acagagtctc actctgtcac    10560
ccaggctgga gtacagtggc acaatctggg ctcactgcaa cctccaactc ccggttcaa    10620
gtgattctca tgcctcaccc tcccgagtag cttggatgac aggagcccgc taccacaccc    10680
agctaatttt tgtattttta gtagagatgg tgtttcacta cattggccag ctggtctca    10740
aactcctgac ctcgtgatcc acccaccttg gcctcccaaa gtgctgggat tacaggtgtg    10800
agccactgcg cccgtcctgg tgtcttttca tataagggca ctaatccaat cagacctggg    10860
cccggcgcgc aattaaccct cactaaaggg aacaaaagct ggagctccac cgcggtggcg    10920
gccgctctag aactagtgga tcgggcccga gctctcgcga ccgggctgca ggaattcgat    10980
cgcgtgctag aattcgcctg tcatacagct aataattgac cataagacaa ttagatttaa    11040
attagttttg aatctttcta ataccaaagt tcagtttact gttccatgtt gcttctgagt    11100
ggcttcacag acttatgaaa aagtaaacgg aatcagaatt acatcaatgc aaaagcattg    11160
ctgtgaactc tgtacttagg actaaacttt gagcaataac acacatagat tgaggattgt    11220
ttgctgttag catacaaact ctggttcaaa gctcctcttt attgcttgtc ttggaaaatt    11280
tgctgttctt catggtttct cttttcactg ctatctattt ttctcaacca ctcacatggc    11340
tacaataact gtctgcaagc ttatgattcc caaatatcta tctctagcct caatcttgtt    11400
ccagaagata aaaagtagta ttcaaatgca catcaacgtc tccacttgga gggcttaaag    11460
acgtttcaac atacaaaccg gggagttttg cctggaatgt ttcctaaaat gtgtcctgta    11520
gcacataggg tcctcttgtt ccttaaaatc taattacttt tagcccagtg ctcatcccac    11580
ctatggggag atgagagtga aaagggagcc tgattaataa ttacactaag tcaataggca    11640
tagagccagg actgtttggg taaactggtc actttatctt aaactaaata tatccaaaac    11700
tgaacatgta cttagttact aagtctttga ctttatctca ttcataccac tcagctttat    11760
ccaggccact tatttgacag tctagctagc ccctagattt tctgcccaa agagctctgt     11820
gtccttgaac ataaaataca aataaccgct atgctgttaa ttattggcaa atgtcccatt    11880
ttcaacctaa ggaaatacca taaagtaaca gatataccaa caaaaggtta ctagttaaca    11940
ggcattgcct gaaaagagta taaaagaatt tcagcatgat tttccatggc ggatgtgtga    12000
catacacgac gccaaaagat tttgttccag ctcctgccac ctccgctacg cgagagatta    12060
accacccacg atggccgcca agtgcatgt tgatattgag gctgacagcc cattcatcaa      12120
gtctttgcag aaggcatttc cgtcgttcga ggtggagtca ttgcaggtca caccaaatga    12180
ccatgcaaat gccagagcat tttcgcacct ggctaccaaa ttgatcgagc aggagactga    12240
caaagacaca ctcatcttgg atatcggcag tgcgccttcc aggagaatga tgtctacgca    12300
caaataccac tgcgtatgcc ctatgcgcag cgcagaagac cccgaaaggc tcgtatgcta    12360
cgcaaagaaa ctggcagcgg cctccgggaa ggtgctggat agagagatcg caggaaaaat    12420
caccgacctg cagaccgtca tggctacgcc agacgctgaa tctcctacct tttgcctgca    12480
tacagacgtc acgtgtcgta cggcagccga agtggccgta taccaggacg tgtatgctgt    12540
acatgcacca acatcgctgt accatcaggc gatgaaaggt gtcagaacgg cgtattggat    12600
tgggtttgac accaccccgt ttatgtttga cgcgctagca ggcgcgtatc caacctacgc    12660
cacaaactgg gccgacgagc aggtgttaca ggccaggaac ataggactgt gtgcagcatc    12720
cttgactgag ggaagactcg gcaaactgtc cattctccgc aagaagcaat tgaaaccttg    12780
cgacacagtc atgttctcgg taggatctac attgtacact gagagcagaa agctactgag    12840
```

```
gagctggcac ttaccctccg tattccacct gaaaggtaaa caatcccttta cctgtaggtg    12900
cgataccatc gtatcatgtg aagggtacgt agttaagaaa atcactatgt gccccggcct    12960
gtacggtaaa acggtagggt acgccgtgac gtatcacgcg gagggattcc tagtgtgcaa    13020
gaccacagac actgtcaaag gagaaagagt ctcattccct gtatgcacct acgtcccctc    13080
aaccatctgt gatcaaatga ctggcatact agcgaccgac gtcacaccgg aggacgcaca    13140
gaagttgtta gtgggattga atcagaggat agttgtgaac ggaagaacac agcgaaacac    13200
taacacgatg aagaactatc tgcttccgat tgtggccgtc gcatttagca agtgggcgag    13260
ggaatacaag gcagaccttg atgatgaaaa acctctgggt gtccgagaga ggtcacttac    13320
ttgctgctgc ttgtgggcat ttaaaacgag gaagatgcac accatgtaca agaaaccaga    13380
cacccagaca atagtgaagg tgccttcaga gtttaactcg ttcgtcatcc cgagcctatg    13440
gtctacaggc ctcgcaatcc cagtcagatc acgcattaag atgcttttgg ccaagaagac    13500
caagcgagag ttaatacctg ttctcgacgc gtcgtcagcc agggatgctg aacaaggagga    13560
gaaggagagg ttggaggccg agctgactag agaagcctta ccaccccctcg tccccatcgc    13620
gccggcggag acgggagtcg tcgacgtcga cgttgaagaa ctagagtatc acgcaggtgc    13680
aggggtcgtg gaaacacctc gcagcgcgtt gaaagtcacc gcacagccga acgacgtact    13740
actaggaaat tacgtagttc tgtccccgca gaccgtgctc aagagctcca agttggcccc    13800
cgtgcaccct ctagcagagc aggtgaaaat aataacacat aacgggaggg ccggcggtta    13860
ccaggtcgac ggatatgacg gcagggtcct actaccatgt ggatcggcca ttccggtccc    13920
tgagtttcaa gctttgagcg agagcgccac tatggtgtac aacgaaaggg agttcgtcaa    13980
caggaaaacta taccatattg ccgttcacgg accgtcgctg aacaccgacg aggagaacta    14040
cgagaaagtc agagctgaaa gaactgacgc cgagtacgtg ttcgacgtag ataaaaaatg    14100
ctgcgtcaag agagaggaag cgtcgggttt ggtgttggtg ggagagctaa ccaacccccc    14160
gttccatgaa ttcgcctacg aagggctgaa gatcaggccg tcggcaccat ataagactac    14220
agtagtagga gtctttgggg ttccgggatc aggcaagtct gctattatta agagcctcgt    14280
gaccaaacac gatctggtca ccagcggcaa gaaggagaac tgccaggaaa tagttaacga    14340
cgtgaagaag caccgcggga aggggacaag tagggaaaac agtgactcca tcctgctaaa    14400
cgggtgtcgt cgtgccgtgg acatcctata tgtggacgag gctttcgctt gccattccgg    14460
tactctgctg gccctaattg ctcttgttaa acctcggagc aaagtggtgt tatgcggaga    14520
ccccaagcaa tgcggattct tcaatatgat gcagcttaag gtgaacttca accacaacat    14580
ctgcactgaa gtatgtcata aagtatatc cagacgttgc acgcgtccag tcacggccat    14640
cgtgtctacg ttgcactacg gaggcaagat gcgcacgacc aacccgtgca acaaacccat    14700
aatcatagac accacaggac agaccaagcc caagccagga gacatcgtgt aacatgctt    14760
ccgaggctgg gcaaagcagc tgcagttgga ctaccgtgga cacgaagtca tgacagcagc    14820
agcatctcag ggcctcaccc gcaaaggggt atacgccgta aggcagaagg tgaatgaaaa    14880
tccccttgtat gccctgcgt cggagcacgt gaatgtactg ctgacgcgca ctgaggatag    14940
gctggtgtgg aaaacgctgg ccggcgatcc ctggattaag gtcctatcaa acattccaca    15000
gggtaacttt acggccacat tggaagaatg gcaagaagaa cacgcaaaaa taatgaaggt    15060
gattgaagga ccggctgcgc ctgtggacgc gttccagaac aaagcgaacg tgtgttgggc    15120
gaaaagcctg gtgcctgtcc tggacactgc cggaatcaga ttgacagcag aggagtggag    15180
caccataatt acagcattta aggaggacag agcttactct ccagtggtgg ccttgaatga    15240
```

```
aatttgcacc aagtactatg gagttgacct ggacagtggc ctgttttctg ccccgaaggt   15300
gtccctgtat tacgagaaca accactggga taacagacct ggtggaagga tgtatggatt   15360
caatgccgca acagctgcca ggctggaagc tagacatacc ttcctgaagg ggcagtggca   15420
tacgggcaag caggcagtta tcgcagaaag aaaaatccaa ccgctttctg tgctggacaa   15480
tgtaattcct atcaaccgca ggctgccgca cgccctggtg gctgagtaca agacggttaa   15540
aggcagtagg gttgagtggc tggtcaataa agtaagaggg taccacgtcc tgctggtgag   15600
tgagtacaac ctggctttgc ctcgacgcag ggtcacttgg ttgtcaccgc tgaatgtcac   15660
aggcgccgat aggtgctacg acctaagttt aggactgccg gctgacgccg gcaggttcga   15720
cttggtcttt gtgaacattc acacggaatt cagaatccac cactaccagc agtgtgtcga   15780
ccacgccatg aagctgcaga tgcttggggg agatgcgcta cgactgctaa acccggcgg   15840 catcttgatg agagcttacg gatacgccga taaaatcagc gaagccgttg tttcctcctt   15900
aagcagaaag ttctcgtctg caagagtgtt gcgcccggat tgtgtcacca gcaatacaga   15960
agtgttcttg ctgttctcca actttgacaa cggaaagaga ccctctacgc tacaccagat   16020
gaataccaag ctgagtgccg tgtatgccgg agaagccatg cacacggccg ggtgtgcacc   16080
atcctacaga gttaagagag cagacatagc cacgtgcaca gaagcggctg tggttaacgc   16140
agctaacgcc cgtggaactg tagggggatgg cgtatgcagg gccgtggcga agaaatggcc   16200
gtcagccttt aagggagcag caacaccagt gggcacaatt aaaacagtca tgtgcggctc   16260
gtaccccgtc atccacgctg tagcgcctaa tttctctgcc acgactgaag cggaagggga   16320
ccgcgaattg gccgctgtct accgggcagt ggccgccgaa gtaaacagac tgtcactgag   16380
cagcgtagcc atcccgctgc tgtccacagg agtgttcagc ggcggaagag ataggctgca   16440
gcaatccctc aaccatctat tcacagcaat ggacgccacg gacgctgacg tgaccatcta   16500
ctgcagagac aaaagttggg agaagaaaat ccaggaagcc attgacatga ggacggctgt   16560
ggagttgctc aatgatgacg tggagctgac cacagacttg gtgagagtgc acccggacag   16620
cagcctggtg ggtcgtaagg gctacagtac cactgacggg tcgctgtact cgtactttga   16680
aggtacgaaa ttcaaccagg ctgctattga tatggcagag atactgacgt tgtggcccag   16740
actgcaagag gcaaacgaac agatatgcct atacgcgctg ggcgaaacaa tggacaacat   16800
cagatccaaa tgtccggtga acgattccga ttcatcaaca cctcccagga cagtgccctg   16860
cctgtgccgc tacgcaatga cagcagaacg gatcgcccgc cttaggtcac accaagttaa   16920
aagcatggtg gtttgctcat cttttcccct cccgaaatac catgtagatg gggtgcagaa   16980
ggtaaagtgc gagaaggttc tcctgttcga cccgacggta ccttcagtgg ttagtccgcg   17040
gaagtatgcc gcatctacga cggaccactc agatcggtcg ttacgagggt ttgacttgga   17100
ctggaccacc gactcgtctt ccactgccag cgataccatg tcgctaccca gtttgcagtc   17160
gtgtgacatc gactcgatct acgagccaat ggctcccata gtagtgacgg ctgacgtaca   17220
ccctgaaccc gcaggcatcg cggacctggc ggcagatgtg caccctgaac cgcagacca   17280 tgtggacctc gagaacccga ttcctccacc gcgcccgaag agagctgcat accttgcctc   17340
ccgcgcggcg gagcgaccgg tgccggcgcc gagaaagccg acgcctgccc caaggactgc   17400
gtttaggaac aagctgccctt tgacgttcgg cgactttgac gagcacgagg tcgatgcgtt   17460
ggcctccggg attactttcg gagacttcga cgacgtcctg cgactaggcc gcgcgggtgc   17520
atatattttc tcctcggaca ctggcagcgg acatttacaa caaaaatccg ttaggcagca   17580
```

```
caatctccag tgcgcacaac tggatgcggt ccaggaggag aaaatgtacc cgccaaaatt    17640
ggatactgag agggagaagc tgttgctgct gaaaatgcag atgcacccat cggaggctaa    17700
taagagtcga taccagtctc gcaaagtgga aacatgaaa gccacggtgg tggacaggct     17760
cacatcgggg gccagattgt acacgggagc ggacgtaggc cgcataccaa catacgcggt    17820
tcggtacccc cgcccgtgt actccctac cgtgatcgaa agattctcaa gccccgatgt      17880
agcaatcgca gcgtgcaacg aataccatc cagaaattac ccaacagtgg cgtcgtacca    17940
gataacagat gaatacgacg catacttgga catggttgac gggtcggata gttgcttgga    18000
cagagcgaca ttctgcccgg cgaagctccg gtgctacccg aaacatcatg cgtaccacca   18060
gccgactgta cgcagtgccg tcccgtcacc ctttcagaac acactacaga acgtgctagc   18120
ggccgccacc aagagaaact gcaacgtcac gcaaatgcga gaactaccca ccatggactc   18180
ggcagtgttc aacgtggagt gcttcaagcg ctatgcctgc tccggagaat attgggaaga   18240
atatgctaaa caacctatcc ggataaccac tgagaacatc actacctatg tgaccaaatt    18300
gaaaggcccg aaagctgctg ccttgttcgc taagacccac aacttggttc cgctgcagga    18360
ggttcccatg gacagattca cggtcgacat gaaacgagat gtcaaagtca ctccagggac    18420
gaaacacaca gaggaaagac ccaaagtcca ggtaattcaa gcagcggagc cattggcgac    18480
cgcttacctg tgcggcatcc acagggaatt agtaaggaga ctaaatgctg tgttacgccc   18540
taacgtgcac acattgtttg atatgtcggc cgaagacttt gacgcgatca tcgcctctca    18600
cttccaccca ggagacccgg ttctagagac ggacattgca tcattcgaca aaagccagga    18660
cgactccttg gctcttacag gtttaatgat cctcgaagat ctaggggtgg atcagtacct    18720
gctggacttg atcgaggcag cctttgggga aatatccagc tgtcacctac caactggcac   18780
gcgcttcaag ttcggagcta tgatgaaatc gggcatgttt ctgactttgt ttattaacac    18840
tgttttgaac atcaccatag caagcagggt actggagcag agactcactg actccgcctg    18900
tgcggccttc atcggcgacg acaacatcgt tcacggagtg atctccgaca gctgatggc    18960 ggagaggtgc gcgtcgtggg tcaacatgga ggtgaagatc attgacgctg tcatgggcga    19020
aaaaccccca tattttttgtg ggggattcat agtttttgac agcgtcacac agaccgcctg   19080
ccgtgtttca gacccactta agcgcctgtt caagttgggt aagccgctaa cagctgaaga   19140
caagcaggac gaagacaggc gacgagcact gagtgacgag gttagcaagt ggttccggac   19200
aggcttgggg gccgaactgg aggtggcact aacatctagg tatgaggtag agggctgcaa    19260
aagtatcctc atagccatgg ccaccttggc gagggacatt aaggcgttta agaaattgag    19320
aggacctgtt atacacctct acggcggtcc tagattggtg cgttaataca cagaattctg   19380
attggatctc gaggtcgacg gtatcgataa gcttgggctg caggtcgatc gactctagag    19440
gatcgatccc caccatgggt caatcacgct acctcctctt tttggccacc cttgccctcc    19500
taaaccacct cagtttggcc agggtcattc cagtctctgg acctgccagg tgtcttagcc   19560
agtcccgaaa cctgctgaag accacagatg acatggtgaa gacggccaga gaaaactga     19620 aacattattc ctgcactgct gaagacatcg atcatgaaga catcacacgg gaccaaacca    19680
gcacattgaa gacctgttta ccactggaac tacacaagaa cgagagttgc ctggctacta    19740
gagagacttc ttccacaaca gagggagct gcctgccccc acagaagacg tctttgatga     19800
tgaccctgtg ccttggtagc atctatgagg acttgaagat gtaccagaca gagttccagg    19860
ccatcaacgc agcacttcag aatcacaacc atcagcagat cattctagac aagggcatgc    19920
tggtggccat cgatgagctg atgcagtctc tgaatcataa tggcgagact ctgcgccaga    19980
```

```
aacctcctgt gggagaagca gacccttaca gagtgaaaat gaagctctgc atcctgcttc    20040
acgccttcag cacccgcgtc gtgaccatca acagggtgat gggctatctg agctccgcct    20100
gagaattccg cccctctccc tccccccccc ctaacgttac tggccgaagc cgcttggaat    20160
aaggccggtg tgcgtttgtc tatatgttat tttccaccat attgccgtct tttggcaatg    20220
tgagggcccg gaaacctggc cctgtcttct tgacgagcat tcctaggggt cttcccctc     20280
tcgccaaagg aatgcaaggt ctgttgaatg tcgtgaagga agcagttcct ctggaagctt    20340
cttgaagaca acaacgtct  gtagcgaccc tttgcaggca gcggaacccc ccacctggcg    20400
acaggtgcct ctgcggccaa agccacgtg  tataagatac acctgcaaag gcggcacaac    20460
cccagtgcca cgttgtgagt tggatagttg tggaaagagt caaatggctc tcctcaagcg    20520
tattcaacaa ggggctgaag gatgcccaga aggtacccca ttgtatggga tctgatctgg    20580
ggcctcggtg cacatgcttt acatgtgttt agtcgaggtt aaaaaacgtc taggcccccc    20640
gaaccacggg gacgtggttt cctttgaaa  acacgatga  taatatggcc acaaccatgg    20700
gtcctcagaa gctaaccatc tcctggtttg ccatcgtttt gctggtgtct ccactcatgg    20760
ccatgtggga gctggagaaa gacgtttatg ttgtagaggt ggactggact cccgatgccc    20820
ctggagaaac agtgaacctc acctgtgaca cgcctgaaga agatgacatc acctggacct    20880
cagaccagag acatggagtc ataggctctg gaaagaccct gaccatcact gtcaaagagt    20940
ttctagatgc tggccagtac acctgccaca aggaggcga  gactctgagc cactcacatc    21000
tgctgctcca caagaaggaa aatggaattt ggtccactga atttttaaaa aatttcaaaa    21060
acaagacttt cctgaagtgt gaagcaccaa attactccgg acggttcacg tgctcatggc    21120
tggtgcaaag aaacatggac ttgaagttca acatcaagag cagtagcagt tcccctgact    21180
ctcgggcagt gacatgtgga atggcgtctc tgtctgcaga aaggtcaca  ctggaccaaa    21240
gggactatga gaagtattca gtgtcctgcc aggaggatgt cacctgccca actgccgagg    21300
agaccctgcc cattgaactg gcgttggaag cacggcagca gaataaatat gagaactaca    21360
gcaccagctt cttcatcagg gacatcatca accagaccc  gcccaagaac ttgcagatga    21420
agcctttgaa gaactcacag gtggaggtca gctgggagta ccctgactcc tggagcactc    21480
cccattccta cttctccctc aagttctttg ttcgaatcca gcgcaagaaa gaaagatga    21540
aggagacaga ggagggtgt  aaccagaaag gtgcgttcct cgtagagaag acatctaccg    21600
aagtccaatg caaaggcggg aatgtctgcg tgcaagctca ggatcgctat tacaattcct    21660
catgcagcaa gtgggcatgt gttccctgca gggtccgatc ctagaattca ttgatccact    21720
aggatcccgg gtaattaatt gaattacatc cctacgcaaa cgttttacgg ccgccggtgg    21780
cgcccgcgcc cggcggcccg tccttggccg ttgcaggcca ctccggtggc tcccgtcgtc    21840
cccgacttcc aggcccagca gatgcagcaa ctcatcagcg ccgtaaatgc gctgacaatg    21900
agacagaacg caattgctcc tgctaggcct cccaaaccaa agaagaagaa gacaaccaaa    21960
ccaaagccga aaacgcagcc caagaagatc aacggaaaaa cgcagcagca aaagaagaaa    22020
gacaagcaag ccgacaagaa gaagaagaaa cccggaaaaa gagaaagaat gtgcatgaag    22080
attgaaaatg actgtatctt cgtatgcggc tagccacagt aacgtagtgt ttccagacat    22140
gtcgggcacc gcactatcat gggtgcagaa aatctcgggt ggtctggggg ccttcgcaat    22200
cggcgctatc ctggtgctgg ttgtggtcac ttgcattggg ctccgcagat aagttagggt    22260
aggcaatggc attgatatag caagaaaatt gaaaacagaa aaagttaggg taagcaatgg    22320
```

-continued

```
catataacca taactgtata acttgtaaca aagcgcaaca agacctgcgc aattggcccc   22380
gtggtccgcc tcacggaaac tcggggcaac tcatattgac acattaattg gcataattg    22440
gaagcttaca taagcttaat tcgacgaata attggatttt tattttattt tgcaattggt   22500
ttttaatatt tccaaaaaaa aaaaaaaaaa aaaaaaaaaa aaaaaaaaaa aaaaaaaaaa   22560
aaaaaaaaaa aaaaaaaaaa aaactagatc ctcgaatcaa gcttatcgat accgtcgact   22620
agagtcgggg cggccggccg cttcgagcag acatgataag atacattgat gagtttggac   22680
aaaccacaac tagaatgcag tgaaaaaaat gctttatttg tgaaatttgt gatgctattg   22740
ctttatttgt aaccattata agctgcaata aacaagttaa caacaacaat tgcattcatt   22800
ttatgtttca ggttcagggg gaggtgtggg aggtttttta aagcaagtaa aacctctaca   22860
aatgtggtaa aatcgataag gatctcgacc tcgagggggg gcccggtacc caattcgccc   22920
tatagtgagt cgtattacgc gcgccctgc aggggggccct gtaccgggct ctgcctgagg   22980
ctctggctgc ccagcaggct gaagctgggg ttgttggcca gggcacttg  tgttcccatc   23040
gcagcgggca cttgtgcctc ccaatcagat ggcctctgaa ggcaggcctg ccagaaggt    23100
gagtgctgct gaacgctatt atccacttgg ctgaggggtg ttttcccga  aactgctgtg   23160
gtcacagctg ctgccgctgt gacccatgca gcattgttga acgcagtggg cattcttggc   23220
acactaggcc gtctgagctg gtggggactc aaggactggg tgcccaggga gctgggacag   23280
aacccaggca ggggcacttc tggtggggtg gccttgggc  tctgcatatg ctggcagaca   23340
gagtcaagtc tgcccagggg agtctggcct gagtgtgaga ggatgggaca ctggggtgctg  23400
gaggtgaaaa ttccttgccg cttccccaga gttggtgaga tcactcccat gccctcgcag   23460
ctctggtgcc tggtgagtgg gatcattcct ggactcagat tgttctgaag aagcccagtt   23520
ctgggtggca tcaagtgctt gctagatggg gggcttgcct tgatccggct acacttggag   23580
gtgacttgtt cttggacggc tacatacaga aagagaag   tggggatgag ttccaaaggc   23640
atcctcgact tcggctgtgg ccaccggagg gtagctcctg gcccaacacg gacttctcac   23700
ctcccgccct tggctctcta ctgagctccc ccctgctccc caattcctcg ccattccct    23760
catttctctg ccctcagcct ggactgcagt tcttctggga agctgccca  actccctagg   23820
tctgtgctca ccaagagcag atcacactgg actgaaatgc cagctgattt gtctcttcaa   23880
gaaaattgga agctcctgga ggtcagggtc catgtctgct tttacactca gtgctctgta   23940
tgcaggcctg gcactgccca ccctttgaca ggtggtgcat attttgtaga aggaaggaag   24000
gggccaggtg gggtgggctg ggctggtggc gggagctagc tcagcctctt agattctcta   24060
cccgatggat gtgacctggg acagcaagtg agtgtggtga gtgagtgcag acggtgcttt   24120
gttccctct  tgtctcatag cctagatggc ctctgagccc agatctgggg ctcagacaac   24180
atttgttcaa ctgaacggta atgggtttcc tttctgaagg ctgaaatctg ggagctgaca   24240
ttctggactc cctgagttct gaagagcctg gggatggaga gacacggagc agaagatgga   24300
aggtagagtc ccaggtgcct aagatgggga atacatctcc cctcattgtc atgagagtcc   24360
actctagcta atatctactg tggccaatat ctaccggtac ttttttgggg tggacactga   24420
gtcatgcagc agtcttatgg tttacccaag gtcaggtagg ggagacagtg cagtcagagc   24480
acaagcccag tgtgtctgac ccacccaaga atccatgctc gtatctacaa aaatgatttt   24540
ttctcttgta atggtgccta ggttctttta ttatcatggc atgtgtatgt ttttcaacta   24600
ggttacaatc tggcccttata aggttaacct cctggaggcc accagccttc ctgaaacttg   24660
tctgtgctgt ccctgcaact ggagtgtgcc tgatgtggca ctccagcctg gacaagtggg   24720
```

```
acacagactc cgctgttatc aggcccaaag atgtcttcca taagaccaga agagcaatgg    24780
tgtagaggtg tcatgggcta caataaagat gctgacctcc tgtctgaggg caagcagcct    24840
cttctggccc tcagacaaat gctgagtgtt cccaagacta ccctcggcct ggtccaatct    24900
catcccactg gtgcgtaagg gttgctgaac tcatgacttc ttggctagcc tgcaacctcc    24960
acggagtggg aactacatca ggcattttgc taactgctgt atcctaggcc aataaatgtt    25020
gatcacattt atagctgcca tggtagggtg gggacccctg ctatctatct gtggaggctc    25080
tgggagcccc tgacacaaac tttctgaagc agagcctccc caaccccttt tccattccct    25140
atacctgaca gatggcccag gaacccatta gaaatggaag gtcactgcag cagtatgtga    25200
atgtgcgtgt gggagaaggg caggatcaga gccctggggg tgtggcagcc cccaagtgat    25260
tctaatccag atcctagggt tgtttccctg tcccattgaa atagctgctt taagggcct     25320 gactcaggga aatcagtctc ttgaattaag tggtgatttt ggagtcattt agaccaggcc    25380
ttcaattggg atcctgctct tagagttgga tgaattattt aactgatttt cagatctcct    25440
ctttctcaat gctttcagaa gcacagtaac tgcttactct gaaatgaatt ctcaccccac    25500
ttccacatat gcaccccttg cccacccctt tgggaacact ggccttaact gcttaccttc    25560
aaatggactc atctgttggg agatatatgc attctgccgt tcagggtca ttgccataag     25620 acctgatctc tgttcctctt gctaaacaga agatgaaaaa gacaaattag attacagcta    25680
ccaattaata attagcctta ggatcgctgc gtggggacct aggacttggc tttggtgcag    25740
cagaaagcat gaataaacac accagcatac actcgcatgc atgccccacc ctctcgagca    25800
aaattccaca ggtataaata aagtaagatt ctgcacctgg gttaaaaaca caactgcaac    25860
agcatagaat ggggcaggag agacagaact taatagcaag agcacacaga aaaaagtttt    25920
aggcattttg gatgtccatc tgctcaggat gggtcagcag tgagatgcgg tcaccaaaag    25980
aacaaatgta acattaggct gcattaatag aagcagagta tgtagaagga gggaggtgac    26040
agtcctatgc taactctgcc ttggccagac tatacccaca ggagtctggg catgccagtc    26100
tcagggagac ccagacagac tggctgcatt cagaggatgg taagtaatga gagtgggat     26160 tggacttcaa actacccaga caaagaatgg ctgagcaagc caaggatgct gtggctgggg    26220
cagagcagac tgtgggctat gtagtggtgg atacctagcc tctgcagggc tgtcataggg    26280
aaaggacatt gagaagagga ctgaggcttg ttcctggtgg tcctggcatg aacggccaga    26340
tgatcacatg tcaggtgga cacagtctcc aacactggga gtagccaaac acttactgcc      26400
aacctcccgc ccttctcctg actagttgca gcataggcaa ttgggaggag cttcctgtct    26460
ccatctgaaa gctggctggg tgggcagggg gaggagcgag ccaagtttca aggccgcagt    26520
ttcagcactc agtctgggat cggctcaagg agcaaagggg aagaacatag ccaggaggga    26580
ataacatgaa ggcccccaga cccagaaaag gcatgacttg ctctgagacc ctcagccggt    26640
tggtgtcagg ttgtgactcg gatccaggtc tgactcccag tccagtgctt gaagcctcac    26700
cccacacagt gaggggagcc cggccatctc tgctcaactg ctgccatctc tctccccttc    26760
tcaaccacca aggcagctct gtctgggagc acaagctcca agtccacttt ctggtctgtg    26820 tccccccaa gatgccagag gacttgcctc tacaacacgg gctgcccgtg cagtgcctgc     26880
ttttccagca aagggcttct gggaaccctt ctctgcactc agtggggctg gtgggagtgg    26940
ggcggggtag cgacccagtg cttgggactg tgcccagctc tcaggcctgg cagcagttcc    27000
tggccttggt tcctgccaag gcagagagga caaacacatg gcaccgggaa gactacacca    27060
```

```
gaagcgattc caccagactg gggtttgctt ttctatcccg cccttagcct gcttcctgtc   27120
ctggtccctg cctcccctc cactggagct gccgtgtggg cagtgagggg ctgtttctca    27180
gctgccctat ggagctgccc tctccctgcc aaagcattgg caaggcggca agggtgggg    27240 gtggggatgg ggggtgggat ctgccttctc aagctctcat tatactgagc acgtctcacc   27300
cattatttta tgtcatctag caacacccca tgtggacact gaggagcatg ggggtcacat   27360
gaccactgcc caaggccaca ccatccggat ctgcctgaga tggtcagggt tggcagccat   27420
ttctgaaggc agtcctttcg ctttggctct tcttgtacca gtctcaggac atcagggcag   27480
aagatctaca gtccccagct tactgatgtg acagcagagc tcagagagg ttaaatgact    27540 tgcccaaggt gacacggcta agaagtacag tatctcctaa ctgcagacca ggtgcttctg   27600
ctgcttctgg ggacagattc ctgcgtggct ggctaggtct aaacggtcct taactccatc   27660
cccaccggtt gctgcattag tttcatcaaa taacacagtt gtacagaggt aggggttcag   27720
gggcaggggc agatggaggc tggagagtgt gactaaggaa acagcagggg aagtgcggta   27780
aagtccgaag ggagggacgg aaagagaaag ccaagcccag gggcgtgcca gacaaaagga   27840
aaggccacgc cggggcaggg caggcttcag cgggtgctgg ggcgtcttca tcccgggaag   27900
cacacattcc agaggacccc ggagtctaat ggaaaagctg gccagcctat cactatggaa   27960
actgccaagg ccacacagcg ctgctgacac ccagcctggg tgccggtggc cagctctgca   28020
ggatcttcaa gtctggggtg ccaccagcaa gcgacggtcc tccatgggct cttcacctta   28080
cggcagtgtc cagaggcacc gccagtcctc tgctcctatg ctggtcctgc tgtccctggc   28140
aaaaggagcc agagcattct ctccaggcct cccgaggagg ctgcttcctt tgttttgcag   28200
atggaggctc ccatcctttg ttctgaatca atgtgctcca aagataagcc ccaagaaaac   28260
agttgttgcc ttttgacact gacaattaga atcgttggaa aatggagaaa acaggaaatg   28320
gcaaatggtt tcagtgacca ggaggaaacc gtgcctgaaa gttgctgctt agtgactggg   28380
acactcgctt tctgctctct tatgaaggac agcctaggcc gtgtggcctt ttataaacaa   28440
agctatgaag gggtcgtcaa attttctagg gctgcaactg tggcactacg tcctgttgtg   28500
ccaggtgaca ctgacaagca gcactgagtt ctatgcaagc ccaggtgtgc ttctctcatg   28560
gtgaccccca gagaactaag gcccagctct tcctctgtca cacccctccc agccccact   28620 gtcagacaag ggaccacatt cacagacagt ctcagccaag atggcaacct tggaagtcct   28680
ggggatgcct ttctagaagc tcgcgcccct aggggccggc cttaattaaa tcaagcttat   28740
cgataccgtc gagacctcga ggggggcat cactccgccc taaaacctac gtcacccgcc    28800
ccgttcccac gccccgcgcc acgtcacaaa ctccaccccc tcattatcat attggcttca   28860
atccaaaata aggtatatta ttgatgatgt tt                                 28892
```

<210> SEQ ID NO 9
<211> LENGTH: 29511
<212> TYPE: DNA
<213> ORGANISM: Chimeric
<220> FEATURE:
<221> NAME/KEY: 5'ITR
<222> LOCATION: (1)..(438)
<223> OTHER INFORMATION: First inverted terminal repeat sequence and
      signal sequence for packaging
<220> FEATURE:
<221> NAME/KEY: Stuffer
<222> LOCATION: (439)..(10905)
<223> OTHER INFORMATION: First non-encoding stuffer sequence
<220> FEATURE:
<221> NAME/KEY: AFP(p+e)
<222> LOCATION: (10906)..(11845)

<223> OTHER INFORMATION: Alpha-fetoprotein (AFP) promoter. Includes
      promoter region (p) and enhancer region (e)
<220> FEATURE:
<221> NAME/KEY: SFV
<222> LOCATION: (12175)..(19281)
<223> OTHER INFORMATION: SFV replicon sequence region
<220> FEATURE:
<221> NAME/KEY: LacZ
<222> LOCATION: (19325)..(22397)
<223> OTHER INFORMATION: Escherichia coli LacZ gene sequence (exogenous
      gene as reporter gene)
<220> FEATURE:
<221> NAME/KEY: PolyA
<222> LOCATION: (23295)..(23554)
<223> OTHER INFORMATION: Polyadenylation sequence derived from SV40
      virus
<220> FEATURE:
<221> NAME/KEY: Relleno
<222> LOCATION: (23555)..(29350)
<223> OTHER INFORMATION: Second stuffer non-coding sequence
<220> FEATURE:
<221> NAME/KEY: 3'ITR
<222> LOCATION: (29351)..(29511)
<223> OTHER INFORMATION: Second inverted terminal repeat sequence

<400> SEQUENCE: 9

```
aaacatcatc aataatatac cttattttgg attgaagcca atatgataat gaggggggtgg      60 agtttgtgac gtggcgcggg gcgtgggaac ggggcgggtg acgtagtagt gtggcggaag     120
tgtgatgttg caagtgtggc ggaacacatg taagcgacgg atgtggcaaa agtgacgttt     180
ttggtgtgcg ccggtgtaca caggaagtga caattttcgc gcggttttag gcggatgttg     240
tagtaaattt gggcgtaacc gagtaagatt tggccatttt cgcgggaaaa ctgaataaga     300
ggaagtgaaa tctgaataat tttgtgttac tcatagcgcg taatatttgt ctagggccgc     360
ggggactttg accgtttacg tggagactcg cccaggtgtt tttctcaggt gttttccgcg     420
ttccgggtca agttggcgt tttgatatca agcttatcga taccgtcaaa caagtcttta     480
attcaagcaa gactttaaca agttaaaagg agcttatggg taggaagtag tgttatgatg     540
tatgggcata aagggtttta atgggatagt gaaaatgtct ataataatac ttaaatggct     600
gcccaatcac ctacaggatt gatgtaaaca tggaaaaggt caaaaacttg ggtcactaaa     660
atagatgatt aatggagagg atgaggttga tagttaaatg tagataagtg gtcttattct     720
caataaaaat gtgaacataa ggcgagtttc tacaaagatg gacaggactc attcatgaaa     780
cagcaaaaac tggacatttg ttctaatctt tgaagagtat gaaaaattcc tattttaaag     840
gtaaaacagt aactcacagg aaataccaac ccaacataaa atcagaaaca atagtctaaa     900
gtaataaaaa tcaaacgttt gcacgatcaa attatgaatg aaattcacta ctaaaattca     960
cactgatttt gtttcatcca cagtgtcaat gttgtgatgc atttcaattg tgtgacacag    1020
gcagactgtg gatcaaaagt ggtttctggt gcgacttact ctcttgagta tacctgcagt    1080 ccccttttctt aagtgtgtta aaaaaaaagg gggattctt caattcgcca atactctagc    1140
tctccatgtg ctttctagga aacaagtgtt aacccacctt atttgtcaaa cctagctcca    1200
aaggactttt gactccccac aaaccgatgt agctcaagag agggtatctg tcaccagtat    1260
gtatagtgaa aaaagtatcc caagtcccaa cagcaattcc taaaggagt ttatttaaaa    1320 aaccacacac acctgtaaaa taagtatata tcctccaagg tgactagttt taaaaaaaca    1380
gtattggctt tgatgtaaag tactagtgaa tatgttagaa aaatctcact gtaaccaagt    1440
gaaatgaaag caagtatggt ttgcagagat tcaagaaaa tataagaaaa cctactgttg    1500
ccactaaaaa gaatcatata ttaaatatac tcacacaata gctcttcagt ctgataaaat    1560
```

```
ctacagtcat aggaatggat ctatcactat ttctattcag tgctttgatg taatccagca   1620
ggtcagcaaa gaatttatag ccccccttga gcacacagag ggctacaatg tgatggcctc   1680
ccatctcctt catcacatct cgagcaagac gttcagtcct acagaaataa aatcaggaat   1740
ttaatagaaa gtttcataca ttaaacttta taacaaacac ctcttagtca ttaaacttcc   1800
acaccaacct gggcaatata gtgagacccc atgcctgcaa aaaaaaaaaa attagccagg   1860
catggtagca tgtacctgta gtcccagcta cttgagaggt gaggtgggaa aatcacttta   1920
gtgcaggatg ttgaggctgg agtgaactgt gattgtgcca ctgcactcca gcctggacaa   1980
tagagcaaga ccttgtctca aaaaaatgca ttaaaaattt tttttaaatc ttccacgtat   2040
cacatccttt gccctcatgt ttcataaggt aaaaaatttg ataccttcaa aaaaaccaag   2100
cataccacta tcataatttt ttttaaatgc aaataaaaac aagataccat tttcacctat   2160
cagactggca ggttctgatt aaatgaaatt ttctggataa tatacaatat taagagagac   2220
tgtagaaact gggccagtgg ctcatgcctg taatcccagc actttgggag ctgggtaac   2280 atggcgaacc ctgtttctac aaaataaaaa tattagctgg gagtggtggc gcacacctat   2340
agtcccagct actcaggagg ctgaggtgga aggatcgctt gaacccagga ggttgagact   2400
gcagtgaact gtgatcattc tgctgcactg caccccagcc tgggcaacag agaccttgtc   2460
tcaaaaaaaa aaaaaaaaga gacaaattgt gaagagaaag gtactctcat ataacatcag   2520
gagtataaaa tgattcaact tcttagagga aaatttggca ataccaaaat attcaataaa   2580
ctctttcccc ttgacccaga aattccactt gaataaagct gaacaagtac caaacatgta   2640
aaagaatgtt tcttctagta cagtcggtaa gaacaaaata gtgtctatca atagtggact   2700 ggttaaaatca gttatggtat ctccataaga cagaatgcta tgcaacccttt aaaatatatt   2760 agatagctct agacacacta atattaaaag tgtccaataa catttaaaac tatactcata   2820
cgttaaaata taaatgtata tatgtactttt tgcatatagt atacatgcat aggccagtgc   2880
ttgagaagaa atgtgtacag aaggctgaaa ggagagaact ttagtcttct tgtttatggc   2940
ctccatagtt agaatatttt ataacacaaa tattttgata ttataatttt aaaataaaaa   3000
cacagaatag ccagacatac aatgcaagca ttcaatacca ggtaaggttt ttcactgtaa   3060
ttgacttaac agaaaatttt caagctagat gtgcataata ataaaaatct gaccttgcct   3120
tcatgtgatt cagccccagt ccattaccct gtttaggact gagaaatgca agactctggc   3180
tagagttcct tcttccatct cccttcaatg tttactttgt tctggtccct acagagtccc   3240
actataccac aactgatact aagtaattag taaggccctc ctcttttatt tttaataaag   3300
aagattttag aaagcatcag ttatttaata agttggccta gtttatgttc aaatagcaag   3360
tactcagaac agctgctgat gttttgaaatt aacacaagaa aaagtaaaaa acctcatttt   3420
aagatcttac ttacctgtcc ataattagtc catgaggaat aaacacccctt tccaaatcct   3480 cagcataatg attaggtatg caaaataaat caaggtcata acctggttca tcatcactaa   3540
tctgaaaaag aaatatagct gtttcaatga gagcattaca ggatacaaac atttgattgg   3600
attaagatgt taaaaaataa ccttagtcta tcagagaaat ttaggtgtaa gatgatatta   3660
gtaactgtta actttgtagg tatgataatg aattatgtaa gaaacaaca ggccgggcgg   3720 gttggttcac acgtgtaatc ccagcacttt gggaggctga ggcaggcaga ctgcctgagc   3780
tcaggagttc gagaccagcc tgggcaacac ggtgaaatcc cgtctctact aaaaatacaa   3840
aaaaattagc cgggtgtggt gacacatgcc tgtagtccca gctacttggg aggctgaggc   3900
aggagaatca cttgaacctg ggaggtgaag gttgcagtga gccaagatgg caccacttca   3960
```

```
ctccagcctg ggaaacagag caagactctg tctctgagct gagatggcac cacttcactc    4020
cagcctggga aacagagcaa gactctgtct caaaaaaaac aaaacacaca aacaaaaaaa    4080
caggctgggc gcggtggctc acgcctgtaa tcccagcact tgggaggcc gaggcgggtg    4140 gatcacctga ggtcaggagt tccagaccag ccttgtcaac atggtgaaac ctcccccgc    4200 cgtctctact aaaaatacaa aaattagcca ggcgtggtgg caggagcctg taatcccagc    4260
tacttgggag gctgaggcag gagaatcgct tgtacccaga aggcagaggt tgcactgagc    4320
tgagatggca ccattgcact ccagcctggg gacaagagc gagatttcgt ctttaaaaaa    4380
caaaaacaaa acaaaaaacc atgtaactat atgtcttagt catcttagtc aagaatgtag    4440
aagtaaagtg ataagatatg gaatttcctt taggtcacaa agagaaaaag aaaaatttta    4500
aagagctaag acaaacgcag caaaatcttt atatttaata atattctaaa catgggtgat    4560
gaacatacgg gtattcatta tactattctc tccacttttg agtatgtttg aaaatttagt    4620
aaaacaagtt ttaacacact gtagtctaac aagataaaat atcacactga acaggaaaaa    4680
ctggcatggt gtggtggctc acacttgtaa tcccagtgct ttgggaggct gagacaggag    4740
agttgcttga ggccaggagt tcaagaccga catggggaat gtagcaagac cccgtcccta    4800
caaaaaactt tgtaaaaatt tgccaggtat ggtggtgcat acctgtagtc ccagctactc    4860
gggaggcgga ggcagaagga atcacttgag cccaggagtt tgaggctgca gtgagctacg    4920
atcataccac agcactccag cgtggacaac agagtaagac cctatctcaa aaacaaaaca    4980
aaacaaaaca aacaaaaaaa accacaagaa aaactgctgg ctgatgcagc ggctcatgcc    5040
tgtaatccca gtattttggg aggcccaggt gggcgtatca cctgaggtca ggagttagag    5100
accagcctgg ccaacatggt gaaacccat ctctactaaa aatacaaaat tagccaggca    5160
tgtggcacgc gcctgtagtc ccagttactg ggaggctgaa gcaggaggat cacctgagcc    5220
cgggaggtgg aggttgcagt gagccgagat cacaccactg cactccagcc tgggtgacac    5280 agcaatacc tacctcaaaa taaaaagaa aagaaaaga aagttgctg tccccgctac    5340 cccaatccca aatccaaaca gcctctctca tctcacagta aggggaaaa atcacccaaa    5400 aaagctaagt gatctttga aaacccaaac tcttagaagt ctaagattat tatagtcaac    5460
tcatgaagtg tcatcataaa agatactcta atattattta agtagaacca catattggtt    5520
gtcttggtat gtctagcccc tggcatacaa atatttaat aacactgata tggtacctgt    5580
gatgtgaaaa tgtactatga gtacagcttt ataaatacta tatatgtacc tatatacaga    5640
aaaaaataca acaaaatcat aaaagcactt atctttgaaa gaggagttac agcaattta    5700 tttagttctt tattgctttg ctatatattc taaattttt tcaatgaata tatatcacttt    5760 ttaaaaaaat tcaatggtct ttcttataaa ttatctttgg cagcatgcgt ttttatatat    5820
acatataaaa tgtatgggaa atttttaaag gatacattaa attaaagcaa aatatacaaa    5880
caaaaaatca gaatacaaaa agataaaaag attgggaagg gagggaggga gtaaggagga    5940
agggtgggtg ggtatagaga aatataccaa ataatggtaa gaagtggggt cttgacactt    6000
tctacacttt ttttaaataa aaaaatttt tttctctctc ttttttttt ttagagacga    6060 agtctcgcta tgttgcccag gctggtcttg aactcctggg atcaagagat cctcctgcct    6120
cagcctccca aggtgcttgg attacaggtg tgagccacca cgcctggtca ctttctacac    6180
tttaatatat atatttttc attttcaatg tcatttttat tagttaattt ataatacccca    6240 ttcaccatta tattcaaagt ctatttgaag aaataaacca gaaagaatga aatactctag    6300
```

```
ctcacatgct attcaatact aaattacctt tcaaatcaca ttcaagaagc tgatgattta    6360
agctttggcg gtttccaata aatattggtc aaaccataat taaatctcaa tatatcagtt    6420
agtacctatt gagcatctcc ttttacaacc taagcattgt attaggtgct taaatacaag    6480
cagcttgact tttaatacat ttaaaaatac atatttaaga cttaaaatct tatttatgga    6540
attcagttat attttgaggt ttccagtgct gagaaatttg aggtttgtgc tgtctttcag    6600
tccccaaagc tcagttctga gttctcagac tttggtggaa cttcatgtat tgtcaggttg    6660
gcccgtaata cctgtgggac aacttcagcc cctgtgcaca tggccaggag gctggttgca    6720
aacattttca ggtaggtgga ccaggacatg cccctggtca tggccaggtg gaggcatagt    6780
gctatacagc aggcagaagt caatattgat ttgttttttaa agaaacatgt actactttca    6840
taagcagaaa aaatttctat tcttggggga aaagattatg ccagatcctc taggattaaa    6900
tgctgatgca tctgctaaac cttcacatat cagaacatat ttactataga aagaatgaaa    6960
atgggacatt tgtgtgtcac ctatgtgaac attccaaaaa tattttacaa caactaagta    7020
ttttataaat tttatgaact gaaatttagt tcaagttcta ggaaaataca aaccttgcta    7080
gatattataa aaatgataca atatatattc atttcaggct catcagaata tatctgttat    7140
cacttgacaa gaatgaaaat gcaccatttt gtagtgcttt aaaatcagga agatccagag    7200
tactaaaaat gacttcttcc ttgaagctta ctcaccaact tcctcccagt tactcactgc    7260
ttctgccaca agcataaact aggacccagc cagaactccc ttgaaatata cacttgcaac    7320
gattactgca tctatcaaaa tggttcagtg cctggctaca ggttctgcag atcgactaag    7380
aatttgaaaa gtcttgttta tttcaaagga agcccatgtg aattctgccc agagttcatc    7440
ccagatatgc agtctaagaa tacagacaga tcagcagaga tgtattctaa acaggaatt    7500 ctggcaatat aacaaattga tttccaatca aaacagattt acataccata cttatgtcaa    7560
gaagttgttt tgttttattg catcctagat tttatttttt tgatttatgg tttactttaa    7620
gcataaaaaa tttgtcaata caactcttcc caaaaggcat aaacaaaaat tcataaaact    7680
tgcatcactt gagatacttc aggtatgaat tcacaacttt gttacaactt actatatata    7740
tgcacacata tatatatatt tgggtatatt ggggggggttc taatttaaga aatgcataat    7800
tggctataga cagacagttg tcagaacttg gcaatgggta cgtgcaggtt cattatacca    7860
agtctacttg tagttgttca aaatgtatca taatacaagg ccgggcgagg tcgtcacgcc    7920
tgtaatccca gcattttggg aggctaaggc aggaggattg cttgaggtca ggagtttgtg    7980
accagcctgg gcaacagagc aagaccctgt ctccaaaaag aaaaaaaata attttttaca    8040
aaataaaaac aaaatgtatc atcagacgaa attaaataag aggcaattca tttaaatgac    8100
aacttttccc agcttgacat ttaacaaaaa gtctaagtcc tcttaattca tatttaatga    8160
tcaaatatca aatactaatt ttttttttttt tttttttttt gagacggagt ctcgctctgt    8220
cgcccaggct ggagtgcagt ggcgcgatcc tggctcactg caagctccgc ctcccgggtt    8280
cacgccattc tcctgcctca gcctcccgag tagctgggat tacagacatg cgccaccacg    8340
cccggctaat tttgtatttt tagtagagat ggggtttctc catgttggtc aggctggtct    8400
tgaatttccc acctcaggtg atctgcctgc ctcagcctca caaagcagta gctgggacta    8460
caggcaccca ccaccacact tggttaattc ttttgtattt tttttgtaaa gacgggattt    8520
caccatgtta gccaggatgg tctcgatctc ctgatctcat gatccgcccg cctcagcctc    8580
ccaaagtgct gggattacag gcgtgagcca ccccgcccgg ccatcaaata ctaattctta    8640
aatggtaagg acccactatt cagaacctgt atccttatca ctaatatgca aatatttatt    8700
```

```
gaatacttac tatgtcatgc atactagaga gagttagata aatttgatac agctaccctc    8760
acagaactta cagtgtaata gatggcatga catgtacatg agtaactgtg aacagtgtta    8820
aattgctatt taaaaaaaaa gacgctggg cgctgtggct catgcctgta atcccagcac    8880
tttgggaggc caaggcaagt tgatcgctcg aggtcaagag ttcgagacca gcctggccaa    8940
cgtggtaaaa ccccgtctct actaaaaata caaaaaaaaa attagccagg catggtggca    9000
caggcctgta atcccagcta ctagggaggc tgagacatgg agaactgctt gaatccagga    9060
ggcagaggtt acagtgagcc gagatcatac cactacactc cagcctgagt gacagagcga    9120
gactcctgtc taaaaaaaaa aaaaaaaaaa aagatacagg ttaagtgtta tggtagttga    9180
agagagaact caaactctgt ctcagaagcc tcacttgcat gtggaccact gatatgaaat    9240
aatataaata ggtataattc aataaatagg aacttcagtt ttaatcatcc caaacaccaa    9300
aacttcctat caaacaggtc caataaactc aatctctata agagctagac agaaatctac    9360
ttggtggcct ataatcttat tagcccttac ttgtcccatc tgatattaat taacccatc     9420 taatatggat tagttaacaa tccagtggct gctttgacag gaacagttgg agagagttgg    9480
ggattgcaac atattcaatt atacaaaaat gcattcagca tctaccttga ttaaggcagt    9540
gtgcaacaga atttcagga gagtaaaaga atgattataa atttacaacc cttaaagagc      9600
tatagctggg cgtggtggct catgcctgta atcccagca ctttgggagg ctgaggcggg      9660
tggatcacct gaggccagaa gttcaagacc agcctagcca acatggcgaa accctgtctc    9720
tacaaaaaat acaaaaatta gccgggtgtg gtggcacgtg cctgtagtcc cagttacttg    9780
ggaggccgag gcaggagaat cgcttgaacc taggaggtgg aggctgcagt gagccgagat    9840
tgtgccactg cactccactt cagcctgggc gacaagagca agactccgtc acaaaaaaaa    9900
aaaaaaaaaa aaagcttaaa atctagtggg aaaggcatat atacatacaa ctaactgtat    9960
agcataataa agctcataat ctgtaacaaa atctaattcg acaagcccag aaacttgtga   10020
tttaccaaaa acagttatat atacacaaaa agtaaaccta gaacccaaag ttacccagca   10080
ccaatgattc tctccctaag cagtatcaag tttaaagcag tgattacatt ctactgccta   10140
gattgtaaac tgagtaaagg agaccagcac ctttctgcta ctgaactagc acagccgtgt   10200
aaaccaacaa ggcaatggca gtgcccaact ttctgtatga atataagtta catctgtttt   10260
attatttgtg acttggtgtt gcatgtggtt attatcaaca ccttctgaaa gaacaactac   10320
ctgctcaggc tgccataaca aaataccaca gactgagtga cttaacagaa acttatttct   10380
cacagttttg gaggctggga agtccaaaat taaggtacct gcaaggtagg tttcaatctc   10440
aggcctcttc tttggcttga aggtcttcta actgtgtgct cacatgacct cttctaacaa   10500
gctctctggt gtctcttttt tttttttttt ctttttttgag acagagtctc actctgtcac   10560
ccaggctgga gtacagtggc acaatctggg ctcactgcaa cctccaactc ccgggttcaa   10620
gtgattctca tgcctcaccc tcccgagtag cttggatgac aggagcccgc taccacaccc   10680
agctaatttt tgtattttta gtagagatgg tgtttcacta cattggccag gctggtctca   10740
aactcctgac ctcgtgatcc acccaccttg gcctcccaaa gtgctgggat tacaggtgtg   10800
agccactgcg cccgtcctgg tgtcttttca tataagggca ctaatccaat cagacctggg   10860
cccgagctct cgcgaccggg ctgcaggaat tcgatcgcgt gctagaattc gcctgtcata   10920
cagctaataa ttgaccataa gacaattaga tttaaattag ttttgaatct ttctaatacc   10980
aaagttcagt ttactgttcc atgttgcttc tgagtggctt cacagactta tgaaaaagta   11040
```

```
aacggaatca gaattacatc aatgcaaaag cattgctgtg aactctgtac ttaggactaa    11100
actttgagca ataacacaca tagattgagg attgtttgct gttagcatac aaactctggt    11160
tcaaagctcc tctttattgc ttgtcttgga aaatttgctg ttcttcatgg tttctctttt    11220
cactgctatc tattttttctc aaccactcac atggctacaa taactgtctg caagcttatg   11280
attcccaaat atctatctct agcctcaatc ttgttccaga agataaaaag tagtattcaa    11340
atgcacatca acgtctccac ttggagggct taaagacgtt tcaacataca aaccggggag    11400
ttttgcctgg aatgtttcct aaaatgtgtc ctgtagcaca tagggtcctc ttgttcctta    11460
aaatctaatt acttttagcc cagtgctcat cccacctatg gggagatgag agtgaaaagg    11520
gagcctgatt aataattaca ctaagtcaat aggcatagag ccaggactgt ttgggtaaac    11580
tggtcacttt atcttaaact aaatatatcc aaaactgaac atgtacttag ttactaagtc    11640
tttgacttta tctcattcat accactcagc tttatccagg ccacttattt gacagtctag    11700
ctagccccta gattttctgc cccaaagagc tctgtgtcct tgaacataaa atacaaataa    11760
ccgctatgct gttaattatt ggcaaatgtc ccattttcaa cctaaggaaa taccataaag    11820
taacagatat accaacaaaa ggttactagt taacaggcat tgcctgaaaa gagtataaaa    11880
gaatttcagc atgattttcc atggcggatg tgtgacatac acgacgccaa aagattttgt    11940
tccagctcct gccacctccg ctacgcgaga gattaaccac ccacgatggc cgccaaagtg    12000
catgttgata ttgaggctga cagcccattc atcaagtctt tgcagaaggc atttccgtcg    12060
ttcgaggtgg agtcattgca ggtcacacca aatgaccatg caaatgccag agcattttcg    12120
cacctggcta ccaaattgat cgagcaggag actgacaaag acacactcat cttggatatc    12180
ggcagtgcgc cttccaggag aatgatgtct acgcacaaat accactgcgt atgccctatg    12240
cgcagcgcag aagaccccga aaggctcgta tgctacgcaa agaaactggc agcggcctcc    12300
gggaaggtgc tggatagaga gatcgcagga aaaatcaccg acctgcagac cgtcatggct    12360
acgccagacg ctgaatctcc tacctttgtc ctgcatacag acgtcacgtg tcgtacggca    12420
gccgaagtgg ccgtatacca ggacgtgtat gctgtacatg caccaacatc gctgtaccat    12480
caggcgatga aaggtgtcag aacggcgtat tggattgggt ttgacaccac cccgtttatg    12540
tttgacgcgc tagcaggcgc gtatccaacc tacgccacaa actgggccga cgagcaggtg    12600
ttacaggcca ggaacatagg actgtgtgca gcatccttga ctgagggaag actcggcaaa    12660
ctgtccattc tccgcaagaa gcaattgaaa ccttgcgaca cagtcatgtt ctcggtagga    12720
tctacattgt acactgagag cagaaagcta ctgaggagct ggcacttacc ctccgtattc    12780
cacctgaaag gtaaacaatc ctttacctgt aggtgcgata ccatcgtatc atgtgaaggg    12840
tacgtagtta agaaaatcac tatgtgcccc ggcctgtacg gtaaaacggt agggtacgcc    12900
gtgacgtatc acgcggaggg attcctagtg tgcaagacca cagacactgt caaggagaa    12960 agagtctcat tccctgtatg cacctacgtc ccctcaacca tctgtgatca aatgactggc    13020
atactagcga ccgacgtcac accggaggac gcacagaagt tgttagtggg attgaatcag    13080
aggatagttg tgaacggaag aacacagcga aacactaaca cgatgaagaa ctatctgctt    13140
ccgattgtgg ccgtcgcatt tagcaagtgg gcgagggaat acaaggcaga ccttgatgat    13200
gaaaaacctc tgggtgtccg agagaggtca cttacttgct gctgcttgtg ggcatttaaa    13260
acgaggaaga tgcacaccat gtacaagaaa ccagacaccc agacaatagt gaaggtgcct    13320
tcagagttta actcgttcgt catcccgagc ctatggtcta caggcctcgc aatcccagtc    13380
agatcacgca ttaagatgct tttggccaag aagaccaagc gagagttaat acctgttctc    13440
```

```
gacgcgtcgt cagccaggga tgctgaacaa gaggagaagg agaggttgga ggccgagctg   13500
actagagaag ccttaccacc cctcgtcccc atcgcgccgg cggagacggg agtcgtcgac   13560
gtcgacgttg aagaactaga gtatcacgca ggtgcagggg tcgtggaaac acctcgcagc   13620
gcgttgaaag tcaccgcaca gccgaacgac gtactactag gaaattacgt agttctgtcc   13680
ccgcagaccg tgctcaagag ctccaagttg gcccccgtgc accctctagc agagcaggtg   13740
aaaataataa cacataacgg gagggccggc ggttaccagg tcgacggata tgacggcagg   13800
gtcctactac catgtggatc ggccattccg gtccctgagt ttcaagcttt gagcgagagc   13860
gccactatgg tgtacaacga aagggagttc gtcaacagga aactatacca tattgccgtt   13920
cacggaccgt cgctgaacac cgacgaggag aactacgaga aagtcagagc tgaaagaact   13980
gacgccgagt acgtgttcga cgtagataaa aaatgctgcg tcaagagaga ggaagcgtcg   14040
ggtttggtgt tggtgggaga gctaaccaac cccccgttcc atgaattcgc ctacgaaggg   14100
ctgaagatca ggccgtcggc accatataag actacagtag taggagtctt tggggttccg   14160
ggatcaggca agtctgctat tattaagagc ctcgtgacca aacacgatct ggtcaccagc   14220
ggcaagaagg agaactgcca ggaaatagtt aacgacgtga agaagcaccg cgggaagggg   14280
acaagtaggg aaaacagtga ctccatcctg ctaaacgggt gtcgtcgtgc cgtggacatc   14340
ctatatgtgg acgaggcttt cgcttgccat tccggtactc tgctggccct aattgctctt   14400
gttaaacctc ggagcaaagt ggtgttatgc ggagacccca agcaatgcgg attcttcaat   14460
atgatgcagc ttaaggtgaa cttcaaccac aacatctgca ctgaagtatg tcataaaagt   14520
atatccagac gttgcacgcg tccagtcacg gccatcgtgt ctacgttgca ctacggaggc   14580
aagatgcgca cgaccaaccc gtgcaacaaa cccataatca tagacaccac aggacagacc   14640
aagcccaagc caggagacat cgtgttaaca tgcttccgag gctgggcaaa gcagctgcag   14700
ttggactacc gtggacacga agtcatgaca gcagcagcat ctcagggcct cacccgcaaa   14760
ggggtatacg ccgtaaggca gaaggtgaat gaaaatccct tgtatgcccc tgcgtcggag   14820
cacgtgaatg tactgctgac gcgcactgag gataggctgg tgtggaaaac gctggccggc   14880
gatccctgga ttaaggtcct atcaaacatt ccacagggta actttacggc cacattggaa   14940
gaatggcaag aagaacacga caaaataatg aaggtgattg aaggaccggc tgcgcctgtg   15000
gacgcgttcc agaacaaagc gaacgtgtgt tgggcgaaaa gcctggtgcc tgtcctggac   15060
actgccggaa tcagattgac agcagaggag tggagcacca taattacagc atttaaggag   15120
gacagagctt actctccagt ggtggccttg aatgaaattt gcaccaagta ctatggagtt   15180
gacctggaca gtgccctgtt ttctgccccg aaggtgtccc tgtattacga gaacaaccac   15240
tgggataaca gacctggtgg aaggatgtat ggattcaatg ccgcaacagc tgccaggctg   15300
gaagctagac ataccttcct gaaggggcag tggcatacgg gcaagcaggc agttatcgca   15360
gaaagaaaaa tccaaccgct ttctgtgctg gacaatgtaa ttcctatcaa ccgcaggctg   15420
ccgcacgccc tggtggctga gtacaagacg gttaaaggca gtagggttga gtggctggtc   15480
aataaagtaa gagggtacca cgtcctgctg gtgagtgagt acaacctggc tttgcctcga   15540
cgcagggtca cttggttgtc accgctgaat gtcacaggcg ccgataggtg ctacgaccta   15600
agtttaggac tgccggctga cgccggcagg ttcgacttgg tctttgtgaa cattcacacg   15660
gaattcagaa tccaccacta ccagcagtgt gtcgaccacg ccatgaagct gcagatgctt   15720
gggggagatg cgctacgact gctaaaaccc ggcggcatct tgatgagagc ttacggatac   15780
```

```
gccgataaaa tcagcgaagc cgttgtttcc tccttaagca gaaagttctc gtctgcaaga   15840
gtgttgcgcc cggattgtgt caccagcaat acagaagtgt tcttgctgtt ctccaacttt   15900
gacaacggaa agagaccctc tacgctacac cagatgaata ccaagctgag tgccgtgtat   15960
gccggagaag ccatgcacac ggccgggtgt gcaccatcct acagagttaa gagagcagac   16020
atagccacgt gcacagaagc ggctgtggtt aacgcagcta acgcccgtgg aactgtaggg   16080
gatggcgtat gcagggccgt ggcgaagaaa tggccgtcag cctttaaggg agcagcaaca   16140
ccagtgggca caattaaaac agtcatgtgc ggctcgtacc ccgtcatcca cgctgtagcg   16200
cctaatttct ctgccacgac tgaagcggaa ggggaccgcg aattggccgc tgtctaccgg   16260
gcagtggccg ccgaagtaaa cagactgtca ctgagcagcg tagccatccc gctgctgtcc   16320
acaggagtgt tcagcggcgg aagagatagg ctgcagcaat ccctcaacca tctattcaca   16380
gcaatggacg ccacggacgc tgacgtgacc atctactgca gagacaaaag ttgggagaag   16440
aaaatccagg aagccattga catgaggacg gctgtggagt tgctcaatga tgacgtggag   16500
ctgaccacag acttggtgag agtgcacccg gacagcagcc tggtgggtcg taagggctac   16560
agtaccactg acgggtcgct gtactcgtac tttgaaggta cgaaattcaa ccaggctgct   16620
attgatatgg cagagatact gacgttgtgg cccagactgc aagaggcaaa cgaacagata   16680
tgcctatacg cgctgggcga aacaatggac aacatcagat ccaaatgtcc ggtgaacgat   16740
tccgattcat caacacctcc caggacagtg ccctgcctgt gccgctacgc aatgacagca   16800
gaacggatcg cccgccttag gtcacaccaa gttaaaagca tggtggtttg ctcatctttt   16860
cccctcccga ataccatgt agatgggggtg cagaaggtaa agtgcgagaa ggttctcctg   16920
ttcgacccga cggtaccttc agtggttagt ccgcggaagt atgccgcatc tacgacggac   16980
cactcagatc ggtcgttacg agggtttgac ttggactgga ccaccgactc gtcttccact   17040
gccagcgata ccatgtcgct acccagtttg cagtcgtgtg acatcgactc gatctacgag   17100
ccaatggctc ccatagtagt gacggctgac gtacaccctg aacccgcagg catcgcggac   17160
ctggcggcag atgtgcaccc tgaacccgca gaccatgtgg acctcgagaa cccgattcct   17220
ccaccgcgcc cgaagagagc tgcataccct tgcctccgcg cggcggagcg accggtgccg   17280
gcgccgagaa agccgacgcc tgccccaagg actgcgttta ggaacaagct gcctttgacg   17340
ttcggcgact ttgacgagca cgaggtcgat gcgttggcct ccgggattac tttcggagac   17400
ttcgacgacg tcctgcgact aggccgcgcg ggtgcatata ttttctcctc ggacactggc   17460
agcggacatt tacaacaaaa atccgttagg cagcacaatc tccagtgcgc acaactggat   17520
gcggtccagg aggagaaaat gtacccgcca aaattggata ctgagaggga gaagctgttg   17580
ctgctgaaaa tgcagatgca cccatcgag gctaataaga gtcgatacca gtctcgcaaa   17640
gtggagaaca tgaaagccac ggtggtggac aggctcacat cggggcccag attgtacacg   17700
ggagcggacg taggccgcat accaacatac gcggttcggt accccgccc cgtgtactcc   17760 cctaccgtga tcgaaagatt ctcaagcccc gatgtagcaa tcgcagcgtg caacgaatac   17820
ctatccagaa attacccaac agtggcgtcg taccagataa cagatgaata cgacgcatac   17880
ttggacatgg ttgacgggtc ggatagttgc ttggacagag cgacattctg cccggcgaag   17940
ctccggtgct acccgaaaca tcatgcgtac caccagccga ctgtacgcag tgccgtcccg   18000 tcacccttc agaacacact acagaacgtg ctagcggccg ccaccaagag aaactgcaac   18060
gtcacgcaaa tgcgagaact acccaccatg gactcggcag tgttcaacgt ggagtgcttc   18120
aagcgctatg cctgctccgg agaatattgg gaagaatatg ctaaacaacc tatccggata   18180
```

```
accactgaga acatcactac ctatgtgacc aaattgaaag gcccgaaagc tgctgccttg   18240
ttcgctaaga cccacaactt ggttccgctg caggaggttc ccatggacag attcacggtc   18300
gacatgaaac gagatgtcaa agtcactcca gggacgaaac acacagagga aagacccaaa   18360
gtccaggtaa ttcaagcagc ggagccattg gcgaccgctt acctgtgcgg catccacagg   18420
gaattagtaa ggagactaaa tgctgtgtta cgccctaacg tgcacacatt gtttgatatg   18480
tcggccgaag actttgacgc gatcatcgcc tctcacttcc acccaggaga cccggttcta   18540
gagacggaca ttgcatcatt cgacaaaagc caggacgact ccttggctct tacaggttta   18600
atgatcctcg aagatctagg ggtggatcag tacctgctgg acttgatcga ggcagccttt   18660
ggggaaatat ccagctgtca cctaccaact ggcacgcgct tcaagttcgg agctatgatg   18720
aaatcgggca tgtttctgac tttgtttatt aacactgttt tgaacatcac catagcaagc   18780
agggtactgg agcagagact cactgactcc gcctgtgcgg ccttcatcgg cgacgacaac   18840
atcgttcacg gagtgatctc cgacaagctg atggcggaga ggtgcgcgtc gtgggtcaac   18900
atggaggtga agatcattga cgctgtcatg ggcgaaaaac ccccatatttt ttgtggggga   18960 ttcatagttt ttgacagcgt cacacagacc gcctgccgtg tttcagaccc acttaagcgc   19020
ctgttcaagt tgggtaagcc gctaacagct gaagacaagc aggacgaaga caggcgacga   19080
gcactgagtg acgaggttag caagtggttc cggacaggct tgggggccga actggaggtg   19140
gcactaacat ctaggtatga ggtagagggc tgcaaaagta tcctcatagc catggccacc   19200
ttggcgaggg acattaaggc gtttaagaaa ttgagaggac ctgttataca cctctacggc   19260
ggtcctagat tggtgcgtta atacacagaa ttctgattat agcgcactat tatatagcac   19320
catggatccc gtcgttttac aacgtcgtga ctgggaaaac cctggcgtta cccaacttaa   19380
tcgccttgca gcacatcccc ctttcgccag ctggcgtaat agcgaagagg cccgcaccga   19440 tcgccctttcc caacagttgc gcagcctgaa tggcgaatgg cgctttgcct ggtttccggc   19500
accagaagcg gtgccggaaa gctggctgga gtgcgatctt cctgaggccg atactgtcgt   19560
cgtcccctca aactggcaga tgcacggtta cgatgcgccc atctacacca acgtaaccta   19620
tcccattacg gtcaatccgc cgtttgttcc cacggagaat ccgacgggtt gttactcgct   19680
cacatttaat gttgatgaaa gctggctaca ggaaggccag acgcgaatta ttttttgatgg   19740 cgttaactcg gcgtttcatc tgtggtgcaa cgggcgctgg gtcggttacg gccaggacag   19800
tcgtttgccg tctgaatttg acctgagcgc atttttacgc gccggagaaa accgcctcgc   19860
ggtgatggtg ctgcgttgga gtgacggcag ttatctggaa gatcaggata tgtggcggat   19920
gagcggcatt ttccgtgacg tctcgttgct gcataaaccg actacacaaa tcagcgattt   19980
ccatgttgcc actcgcttta atgatgattt cagccgcgct gtactggagg ctgaagttca   20040
gatgtgcggc gagttgcgtg actacctacg ggtaacagtt tctttatggc agggtgaaac   20100
gcaggtcgcc agcggcaccg cgcctttcgg cggtgaaatt atcgatgagc gtggtggtta   20160
tgccgatcgc gtcacactac gtctgaacgt cgaaaacccg aaactgtgga gcgccgaaat   20220
cccgaatctc tatcgtgcgg tggttgaact gcacaccgcc gacggcacgc tgattgaagc   20280
agaagcctgc gatgtcggtt ccgcgaggt gcggattgaa aatggtctgc tgctgctgaa   20340
cggcaagccg ttgctgattc gaggcgttaa ccgtcacgag catcatcctc tgcatggtca   20400
ggtcatggat gagcagacga tggtgcagga tatcctgctg atgaagcaga acaactttaa   20460
cgccgtgcgc tgttcgcatt atccgaacca tccgctgtgg tacacgctgt gcgaccgcta   20520
```

```
cggcctgtat gtggtggatg aagccaatat tgaaacccac ggcatggtgc caatgaatcg   20580
tctgaccgat gatccgcgct ggctaccggc gatgagcgaa cgcgtaacgc gaatggtgca   20640
gcgcgatcgt aatcacccga gtgtgatcat ctggtcgctg gggaatgaat caggccacgg   20700
cgctaatcac gacgcgctgt atcgctggat caaatctgtc gatccttccc gcccggtgca   20760
gtatgaaggc ggcggagccg acaccacggc caccgatatt atttgcccga tgtacgcgcg   20820
cgtggatgaa gaccagccct tcccggctgt gccgaaatgg tccatcaaaa aatggctttc   20880
gctacctgga gagacgcgcc cgctgatcct ttgcgaatac gcccacgcga tgggtaacag   20940
tcttggcggt ttcgctaaat actggcaggc gtttcgtcag tatccccgtt tacagggcgg   21000
cttcgtctgg gactgggtgg atcagtcgct gattaaatat gatgaaaacg gcaacccgtg   21060
gtcggcttac ggcggtgatt ttggcgatac gccgaacgat cgccagttct gtatgaacgg   21120
tctggtcttt gccgaccgca cgccgcatcc agcgctgacg gaagcaaaac accagcagca   21180 gttttccag ttccgtttat ccgggcaaac catcgaagtg accagcgaat acctgttccg   21240
tcatagcgat aacgagctcc tgcactggat ggtggcgctg gatggtaagc cgctggcaag   21300
cggtgaagtg cctctggatg tcgctccaca aggtaaacag ttgattgaac tgcctgaact   21360
accgcagccg gagagcgccg ggcaactctg gctcacagta cgcgtagtgc aaccgaacgc   21420
gaccgcatgg tcagaagccg ggcacatcag cgcctggcag cagtggcgtc tggcggaaaa   21480
cctcagtgtg acgctccccg ccgcgtccca cgccatcccg catctgacca ccagcgaaat   21540
ggatttttgc atcgagctgg gtaataagcg ttggcaattt aaccgccagt caggctttct   21600
ttcacagatg tggattggcg ataaaaaaca actgctgacg ccgctgcgcg atcagttcac   21660
ccgtgcaccg ctggataacg acattggcgt aagtgaagcg accgcattg accctaacgc   21720 ctgggtcgaa cgctggaagg cggcgggcca ttaccaggcc gaagcagcgt tgttgcagtg   21780
cacggcagat acacttgctg atgcggtgct gattacgacc gctcacgcgt ggcagcatca   21840
ggggaaaacc ttatttatca gccggaaaac ctaccggatt gatggtagtg gtcaaatggc   21900
gattaccgtt gatgttgaag tggcgagcga taccgcat ccggcgcgga ttggcctgaa   21960
ctgccagctg gcgcaggtag cagagcgggt aaactggctc ggattagggc cgcaagaaaa   22020
ctatcccgac cgccttactg ccgcctgttt tgaccgctgg gatctgccat tgtcagacat   22080
gtataccccg tacgtcttcc cgagcgaaaa cggtctgcgc tgcgggacgc gcgaattgaa   22140
ttatggccca caccagtggc gcggcgactt ccagttcaac atcagccgct acagtcaaca   22200
gcaactgatg gaaaccagcc atcgccatct gctgcacgcg gaagaaggca catggctgaa   22260
tatcgacggt ttccatatgg ggattggtgg cgacgactcc tggagcccgt cagtatcggc   22320
ggaattccag ctgagcgccg gtcgctacca ttaccagttg gtctggtgtc aaaaataata   22380
ataaccgggc aggggggatc ccgggtaatt aattgaatta catccctacg caaacgtttt   22440
acggccgccg gtgcgcccg cgcccggcgg cccgtccttg gccgttgcag gccactccgg   22500
tggctcccgt cgtccccgac ttccaggccc agcagatgca gcaactcatc agcgccgtaa   22560
atgcgctgac aatgagacag aacgcaattg ctcctgctag gcctcccaaa ccaaagaaga   22620
agaagacaac caaaccaaag ccgaaaacgc agcccaagaa gatcaacgga aaacgcagc   22680 agcaaaagaa gaaagacaag caagccgaca agaagaagaa gaaacccgga aaagagaaa   22740 gaatgtgcat gaagattgaa aatgactgta tcttcgtatg cggctagcca cagtaacgta   22800
gtgtttccag acatgtcggg caccgcacta tcatgggtgc agaaaatctc gggtggtctg   22860
ggggccttcg caatcggcgc tatcctggtg ctggttgtgg tcacttgcat tgggctccgc   22920
```

| | | | | | |
|---|---|---|---|---|---|
| agataagtta | gggtaggcaa | tggcattgat | atagcaagaa | aattgaaaac | agaaaaagtt | 22980 |
| agggtaagca | atggcatata | accataactg | tataacttgt | aacaaagcgc | aacaagacct | 23040 |
| gcgcaattgg | ccccgtggtc | cgcctcacgg | aaactcgggg | caactcatat | tgacacatta | 23100 |
| attggcaata | attggaagct | tacataagct | taattcgacg | aataattgga | tttttatttt | 23160 |
| attttgcaat | tggtttttaa | tatttccaaa | aaaaaaaaaa | aaaaaaaaaa | aaaaaaaaaa | 23220 |
| aaaaaaaaaa | aaaaaaaaaa | aaaaaaaaaa | aaaaaaacta | gatcctcgaa | tcaagcttat | 23280 |
| cgataccgtc | gactagagtc | ggggcggccg | gccgcttcga | gcagacatga | taagatacat | 23340 |
| tgatgagttt | ggacaaacca | caactagaat | gcagtgaaaa | aaatgctttta | tttgtgaaat | 23400 |
| ttgtgatgct | attgctttat | ttgtaaccat | tataagctgc | aataaacaag | ttaacaacaa | 23460 |
| caattgcatt | cattttatgt | ttcaggttca | gggggaggtg | tgggaggttt | tttaaagcaa | 23520 |
| gtaaaacctc | tacaaatgtg | gtaaaatcga | taaggatctc | gacctcgagg | ggggccctg | 23580 |
| taccgggctc | tgcctgaggc | tctggctgcc | cagcaggctg | aagctgggt | tgttggccag | 23640 |
| gggcacttgt | gttcccatcg | cagcgggcac | ttgtgcctcc | caatcagatg | gcctctgaag | 23700 |
| gcaggcctgg | ccagaaggtg | agtgctgctg | aacgctatta | tccacttggc | tgaggggtgt | 23760 |
| ttccccgaa | actgctgtgg | tcacagctgc | tgccgctgtg | acccatgcag | cattgttgaa | 23820 |
| cgcagtgggc | attcttggca | cactaggccg | tctgagctgg | tggggactca | aggactgggt | 23880 |
| gcccagggag | ctgggacaga | acccaggcag | gggcacttct | ggtggggtgg | ccttggggct | 23940 |
| ctgcatatgc | tggcagacag | agtcaagtct | gcccagggga | gtctgcctg | agtgtgagag | 24000 |
| gatgggacac | tgggggctgg | aggtgaaaat | tccttgccgc | ttccccagag | ttggtgagat | 24060 |
| cactcccatg | ccctcgcagc | tctggtgcct | ggtgagtggg | atcattcctg | gactcagatt | 24120 |
| gttctgaaga | agcccagttc | tgggtggcat | caagtgcttg | ctagatgggg | ggcttgcctt | 24180 |
| gatccggcta | cacttggagg | tgacttgttc | ttggacggct | acatacagaa | agagagaagt | 24240 |
| ggggatgagt | tccaaaggca | tcctcgactt | cggctgtggc | caccggaggg | tagctcctgg | 24300 |
| cccaacacgg | acttctcacc | tcccgccctt | ggctctctac | tgagctcccc | cctgctcccc | 24360 |
| aattcctcgc | cattcccctc | atttctctgc | cctcagcctg | gactgcagtt | cttctgggaa | 24420 |
| gctgccccaa | ctccctaggt | ctgtgctcac | caagagcaga | tcacactgga | ctgaaatgcc | 24480 |
| agctgatttg | tctcttcaag | aaaattggaa | gctcctggag | gtcagggtcc | atgtctgctt | 24540 |
| ttacactcag | tgctctgtat | gcaggcctgg | cactgcccac | cctttgacag | gtggtgcata | 24600 |
| ttttgtagaa | ggaaggaagg | ggccaggtgg | ggtgggctgg | gctggtggcg | ggagctagct | 24660 |
| cagcctctta | gattctctac | ccgatggatg | tgacctggga | cagcaagtga | gtgtggtgag | 24720 |
| tgagtgcaga | cggtgctttg | ttcccctctt | gtctcatagc | ctagatggcc | tctgagccca | 24780 |
| gatctggggc | tcagacaaca | tttgttcaac | tgaacggtaa | tgggtttcct | ttctgaaggc | 24840 |
| tgaaatctgg | gagctgacat | tctggactcc | ctgagttctg | aagagcctgg | ggatggagag | 24900 |
| acacggagca | gaagatggaa | ggtagagtcc | caggtgccta | agatggggaa | tacatctccc | 24960 |
| ctcattgtca | tgagagtcca | ctctagctga | tatctactgt | ggccaatatc | taccggtact | 25020 |
| tttttgggt | ggacactgag | tcatgcagca | gtcttatggt | ttaccaagg | tcaggtaggg | 25080 |
| gagacagtgc | agtcagagca | caagcccagt | gtgtctgacc | cacccaagaa | tccatgctcg | 25140 |
| tatctacaaa | aatgattttt | tctcttgtaa | tggtgcctag | gttcttttat | tatcatggca | 25200 |
| tgtgtatgtt | tttcaactag | gttacaatct | ggccttataa | ggttaaccte | ctggaggcca | 25260 |

```
ccagccttcc tgaaacttgt ctgtgctgtc cctgcaactg gagtgtgcct gatgtggcac    25320
tccagcctgg acaagtggga cacagactcc gctgttatca ggcccaaaga tgtcttccat    25380
aagaccagaa gagcaatggt gtagaggtgt catgggctac aataaagatg ctgacctcct    25440
gtctgagggc aagcagcctc ttctggccct cagacaaatg ctgagtgttc caagactac    25500 cctcggcctg gtccaatctc atcccactgg tgcgtaaggg ttgctgaact catgacttct    25560
tggctagcct gcaacctcca cggagtggga actacatcag gcattttgct aactgctgta    25620
tcctaggcca ataaatgttg atcacattta tagctgccat ggtagggtgg ggacccctgc    25680
tatctatctg tggaggctct gggagcccct gacacaaact ttctgaagca gagcctcccc    25740
aacccctttt ccattcccta tacctgacag atggcccagg aacccattag aaatggaagg    25800
tcactgcagc agtatgtgaa tgtgcgtgtg ggagaagggc aggatcagag ccctgggggt    25860
gtggcagccc ccaagtgatt ctaatccaga tcctagggtt gtttccctgt cccattgaaa    25920
tagctgcttt aaggggcctg actcagggaa atcagtctct tgaattaagt ggtgattttg    25980
gagtcattta gaccaggcct tcaattggga tcctgctctt agagttggat gaattattta    26040
actgattttc agatctcctc tttctcaatg ctttcagaag cacagtaact gcttactctg    26100
aaatgaattc tcaccccact tccacatatg caccccttgc ccaccccttt gggaacactg    26160
gccttaactg cttaccttca aatggactca tctgttggga gatatatgca ttctgccgtt    26220
caggggtcat tgccataaga cctgatctct gttcctcttg ctaaacagaa gatgaaaaag    26280
acaaattaga ttacagctac caattaataa ttagccttag gatcgctgcg tggggaccta    26340
ggacttggct ttggtgcagc agaaagcatg aataaacaca ccagcataca ctcgcatgca    26400
tgccccaccc tctcgagcaa aattccacag gtataaataa agtaagattc tgcacctggg    26460
ttaaaaacac aactgcaaca gcatagaatg gggcaggaga gacagaactt aatagcaaga    26520
gcacacagaa aaaagtttta ggcattttgg atgtccatct gctcaggatg ggtcagcagt    26580
gagatgcggt caccaaaaga acaaatgtaa cattaggctg cattaataga agcagagtat    26640
gtagaaggag ggaggtgaca gtcctatgct aactctgcct tggccagact atacccacag    26700
gagtctgggc atgccagtct cagggagacc cagacagact ggctgcattc agaggatggt    26760
aagtaatgag agtgggggatt ggacttcaaa ctacccagac aaagaatggc tgagcaagcc    26820
aaggatgctg tggctggggc agagcagact gtgggctatg tagtggtgga tacctagcct    26880
ctgcagggct gtcataggga aaggacattg agaagaggac tgaggcttgt tcctggtggt    26940
cctggcatga acggccagat gatcacatgg tcaggtggac acagtctcca acactgggag    27000
tagccaaaca cttactgcca acctcccgcc cttctcctga ctagttgcag cataggcaat    27060
tgggaggagc ttcctgtctc catctgaaag ctggctgggt gggcagggggg aggagcgagc    27120 caagtttcaa ggccgcagtt tcagcactca gtctgggatc ggctcaagga gcaaagggga    27180
agaacatagc caggagggaa taacatgaag gcccccagac ccagaaaagg catgacttgc    27240
tctgagaccc tcagccggtt ggtgtcaggt tgtgactcgg atccaggtct gactcccagt    27300
ccagtgcttg aagcctcacc ccacacagtg aggggagccc ggccatctct gctcaactgc    27360
tgccatctct ctccccttct caaccaccaa ggcagctctg tctgggagca caagctccaa    27420
gtccactttc tggtctgtgt cccccccaag atgccagagg acttgcctct acaacacggg    27480
ctgcccgtgc agtgcctgct tttccagcaa agggcttctg ggaacccttc tctgcactca    27540
gtggggctgg tgggagtggg gcggggtagc gacccagtgc ttgggactgt gcccagctct    27600
caggcctggc agcagttcct ggccttggtt cctgccaagg cagagaggac aaacacatgg    27660
```

```
caccgggaag actacaccag aagcgattcc accagactgg ggtttgcttt tctatcccgc   27720
ccttagcctg cttcctgtcc tggtccctgc ctcccctcc actggagctg ccgtgtgggc    27780
agtgaggggc tgtttctcag ctgccctatg gagctgccct ctccctgcca aagcattggc   27840
aaggcggcaa ggggtggggg tggggatggg gggtgggatc tgccttctca agctctcatt   27900
atactgagca cgtctcaccc attattttat gtcatctagc aacacccat gtggacactg    27960 aggagcatgg gggtcacatg accactgccc aaggccacac catccggatc tgcctgagat   28020
ggtcagggtt ggcagccatt tctgaaggca gtcctttcgc tttggctctt cttgtaccag   28080
tctcaggaca tcagggcaga agatctacag tccccagctt actgatgtga cagcagaggc   28140
tcagagaggt taaatgactt gcccaaggtg acacggctaa gaagtacagt atctcctaac   28200
tgcagaccag gtgcttctgc tgcttctggg gacagattcc tgcgtggctg gctaggtcta   28260
aacggtcctt aactccatcc ccaccggttg ctgcattagt ttcatcaaat aacacagttg   28320
tacagaggta ggggttcagg ggcaggggca gatggaggct ggagagtgtg actaaggaaa   28380
cagcagggga agtgcggtaa agtccgaagg gagggacgga aagagaaagc caagcccagg   28440
ggcgtgccag acaaaaggaa aggccacgcc ggggcagggc aggcttcagc gggtgctggg   28500
gcgtcttcat cccgggaagc acacattcca gaggaccccg gagtctaatg gaaaagctgg   28560
ccagcctatc actatggaaa ctgccaaggc cacacagcgc tgctgacacc cagcctgggt   28620
gccggtggcc agctctgcag gatcttcaag tctggggtgc caccagcaag cgacggtcct   28680
ccatgggctc ttcaccttac ggcagtgtcc agaggcaccg ccagtcctct gctcctatgc   28740
tggtcctgct gtccctggca aaaggagcca gagcattctc tccaggcctc ccgaggaggc   28800
tgcttccttt gttttgcaga tggaggctcc catcctttgt tctgaatcaa tgtgctccaa   28860
agataagccc caagaaaaca gttgttgcct tttgacactg acaattagaa tcgttggaaa   28920
atggagaaaa caggaaatgg caaatggttt cagtgaccag gaggaaaccg tgcctgaaag   28980
ttgctgctta gtgactggga cactcgcttt ctgctctctt atgaaggaca gcctaggccg   29040
tgtggccttt tataaacaaa gctatgaagg ggtcgtcaaa ttttctaggg ctgcaactgt   29100
ggcactacgt cctgttgtgc caggtgacac tgacaagcag cactgagttc tatgcaagcc   29160
caggtgtgct tctctcatgg tgaccccag agaactaagg cccagctctt cctctgtcac    29220
acccctccca gccccactg tcagacaagg gaccacattc acagacagtc tcagccaaga    29280
tggcaacctt ggaagtcctg gggatgcctt tctagaagct cgcgcccta ggggccggcc    29340 ttaattaaat caagcttatc gataccgtcg agacctcgag gggggcatc actccgccct    29400 aaaacctacg tcacccgccc cgttcccacg ccccgcgcca cgtcacaaac tccaccccct   29460
cattatcata ttggcttcaa tccaaaataa ggtatattat tgatgatgtt t            29511
```

<210> SEQ ID NO 10
<211> LENGTH: 28191
<212> TYPE: DNA
<213> ORGANISM: Chimeric
<220> FEATURE:
<221> NAME/KEY: 5'ITR
<222> LOCATION: (1)..(438)
<223> OTHER INFORMATION: First inverted terminal repeat sequence and
      signal sequence for packaging
<220> FEATURE:
<221> NAME/KEY: Stuffer
<222> LOCATION: (439)..(10990)
<223> OTHER INFORMATION: First non-encoding stuffer sequence
<220> FEATURE:
<221> NAME/KEY: TERT

```
<222> LOCATION: (10991)..(11285)
<223> OTHER INFORMATION: Telomerase promoter (TERT)
<220> FEATURE:
<221> NAME/KEY: SFV
<222> LOCATION: (11556)..(18665)
<223> OTHER INFORMATION: SFV replicon sequence region
<220> FEATURE:
<221> NAME/KEY: mIL-12
<222> LOCATION: (18688)..(21021)
<223> OTHER INFORMATION: Mouse interleukin-12 (IL-12) gene sequence
<220> FEATURE:
<221> NAME/KEY: PolyA
<222> LOCATION: (21920)..(22179)
<223> OTHER INFORMATION: Polyadenylation sequence derived from SV40
      virus
<220> FEATURE:
<221> NAME/KEY: Stuffer
<222> LOCATION: (22180)..(28030)
<223> OTHER INFORMATION: Second non-encoding stuffer sequence
<220> FEATURE:
<221> NAME/KEY: 3'ITR
<222> LOCATION: (28031)..(28191)
<223> OTHER INFORMATION: First inverted terminal repeat sequence

<400> SEQUENCE: 10
aaacatcatc aataatatac cttatttttgg attgaagcca atatgataat gaggggtgg      60 agtttgtgac gtggcgcggg gcgtgggaac ggggcgggtg acgtagtagt gtggcggaag     120
tgtgatgttg caagtgtggc ggaacacatg taagcgacgg atgtggcaaa agtgacgttt     180
ttggtgtgcg ccggtgtaca caggaagtga caattttcgc gcggttttag gcggatgttg     240
tagtaaattt gggcgtaacc gagtaagatt tggccatttt cgcgggaaaa ctgaataaga     300
ggaagtgaaa tctgaataat tttgtgttac tcatagcgcg taatatttgt ctagggccgc     360
ggggactttg accgtttacg tggagactcg cccaggtgtt tttctcaggt gttttccgcg     420
ttccgggtca agttggcgt tttgatatca agcttatcga taccgtcaaa caagtcttta     480
attcaagcaa gactttaaca agttaaaagg agcttatggg taggaagtag tgttatgatg     540
tatgggcata aagggtttta atgggatagt gaaaatgtct ataataatac ttaaatggct     600
gcccaatcac ctacaggatt gatgtaaaca tggaaaaggt caaaaacttg ggtcactaaa     660
atagatgatt aatggagagg atgaggttga tagttaaatg tagataagtg gtcttattct     720
caataaaaat gtgaacataa ggcgagtttc tacaaagatg gacaggactc attcatgaaa     780
cagcaaaaac tggacatttg ttctaatctt tgaagagtat gaaaaattcc tattttaaag     840
gtaaaacagt aactcacagg aaataccaac ccaacataaa atcagaaaca atagtctaaa     900
gtaataaaaa tcaaacgttt gcacgatcaa attatgaatg aaattcacta ctaaaattca     960
cactgatttt gtttcatcca cagtgtcaat gttgtgatgc atttcaattg tgtgacacag    1020
gcagactgtg gatcaaaagt ggtttctggt gcgacttact ctcttgagta tacctgcagt    1080
cccctttctt aagtgtgtta aaaaaaaagg gggatttctt caattcgcca atactctagc    1140
tctccatgtg ctttctagga aacaagtgtt aacccacctt atttgtcaaa cctagctcca    1200
aaggactttt gactccccac aaaccgatgt agctcaagag agggtatctg tcaccagtat    1260
gtatagtgaa aaagtatcc caagtcccaa cagcaattcc taaaaggagt ttatttaaaa    1320
aaccacacac acctgtaaaa taagtatata tcctccaagg tgactagttt taaaaaaaca    1380
gtattggctt tgatgtaaag tactagtgaa tatgttagaa aaatctcact gtaaccaagt    1440
gaaatgaaag caagtatggt ttgcagagat tcaaagaaaa tataagaaaa cctactgttg    1500
ccactaaaaa gaatcatata ttaaatatac tcacacaata gctcttcagt ctgataaaat    1560
ctacagtcat aggaatggat ctatcactat ttctattcag tgctttgatg taatccagca    1620
```

```
ggtcagcaaa gaatttatag ccccccttga gcacacagag ggctacaatg tgatggcctc    1680
ccatctcctt catcacatct cgagcaagac gttcagtcct acagaaataa aatcaggaat    1740
ttaatagaaa gtttcataca ttaaacttta taacaaacac ctcttagtca ttaaacttcc    1800
acaccaacct gggcaatata gtgagacccc atgcctgcaa aaaaaaaaaa attagccagg    1860
catggtagca tgtacctgta gtcccagcta cttgagaggt gaggtgggaa aatcacttta    1920
gtgcaggatg ttgaggctgg agtgaactgt gattgtgcca ctgcactcca gcctggacaa    1980
tagagcaaga ccttgtctca aaaaatgca ttaaaaattt tttttaaatc ttccacgtat     2040
cacatccttt gccctcatgt ttcataaggt aaaaaatttg ataccttcaa aaaaccaag     2100 cataccacta tcataatttt ttttaaatgc aaataaaaac aagataccat tttcacctat    2160
cagactggca ggttctgatt aaatgaaatt ttctggataa tatacaatat aagagagac     2220 tgtagaaact gggccagtgg ctcatgcctg taatcccagc actttgggag ctgggtaac     2280 atggcgaacc ctgtttctac aaaataaaaa tattagctgg gagtggtggc gcacacctat    2340
agtcccagct actcaggagg ctgaggtgga aggatcgctt gaacccagga ggttgagact    2400
gcagtgaact gtgatcattc tgctgcactg caccccagcc tgggcaacag agaccttgtc    2460
tcaaaaaaaa aaaaaaaaga gacaaattgt gaagagaaag gtactctcat ataacatcag    2520
gagtataaaa tgattcaact tcttagagga aaatttggca ataccaaaat attcaataaa    2580
ctctttcccc ttgacccaga aattccactt gaataaagct gaacaagtac caaacatgta    2640
aaagaatgtt tcttctagta cagtcggtaa gaacaaaata gtgtctatca atagtggact    2700
ggttaaatca gttatggtat ctccataaga cagaatgcta tgcaaccttt aaaatatatt    2760
agatagctct agacacacta atattaaaag tgtccaataa catttaaaac tatactcata    2820
cgttaaaata taaatgtata tatgtacttt tgcatatagt atacatgcat aggccagtgc    2880
ttgagaagaa atgtgtacag aaggctgaaa ggagagaact ttagtcttct tgtttatggc    2940
ctccatagtt agaatatttt ataacacaaa tattttgata ttataatttt aaaataaaaa    3000
cacagaatag ccagacatac aatgcaagca ttcaatacca ggtaaggttt ttcactgtaa    3060
ttgacttaac agaaaatttt caagctagat gtgcataata ataaaaatct gaccttgcct    3120
tcatgtgatt cagcccccagt ccattaccct gtttaggact gagaaatgca agactctggc    3180
tagagttcct tcttccatct cccttcaatg tttactttgt tctggtccct acagagtccc    3240
actataccac aactgatact aagtaattag taaggccctc ctcttttatt tttaataaag    3300
aagattttag aaagcatcag ttatttaata agttggccta gtttatgttc aaatagcaag    3360
tactcagaac agctgctgat gtttgaaatt aacacaagaa aaagtaaaaa acctcatttt    3420
aagatcttac ttacctgtcc ataattagtc catgaggaat aaacacccctt tccaaatcct   3480 cagcataatg attaggtatg caaaataaat caaggtcata acctggttca tcatcactaa    3540
tctgaaaaag aaatatagct gtttcaatga gagcattaca ggatacaaac atttgattgg    3600
attaagatgt taaaaaataa ccttagtcta tcagagaaat ttaggtgtaa gatgatatta    3660
gtaactgtta actttgtagg tatgataatg aattatgtaa gaaacaaca ggccgggcgg     3720 gttggttcac acgtgtaatc ccagcacttt gggaggctga ggcaggcaga ctgcctgagc    3780
tcaggagttc gagaccagcc tgggcaacac ggtgaaatcc cgtctctact aaaaatacaa    3840
aaaaattagc cgggtgtggt gacacatgcc tgtagtccca gctacttggg aggctgaggc    3900
aggagaatca cttgaacctg ggaggtgaag gttgcagtga gccaagatgg caccacttca    3960
```

```
ctccagcctg ggaaacagag caagactctg tctctgagct gagatggcac cacttcactc    4020
cagcctggga acagagcaa gactctgtct caaaaaaaac aaaacacaca aacaaaaaaa      4080
caggctgggc gcggtggctc acgcctgtaa tcccagcact ttgggaggcc gaggcgggtg    4140
gatcacctga ggtcaggagt tccagaccag ccttgtcaac atggtgaaac ctcccccgc    4200 cgtctctact aaaaatacaa aaattagcca ggcgtggtgg caggagcctg taatcccagc    4260
tacttgggag gctgaggcag gagaatcgct tgtacccaga aggcagaggt tgcactgagc    4320
tgagatggca ccattgcact ccagcctggg ggacaagagc gagatttcgt ctttaaaaaa    4380 caaaacaaa acaaaaaacc atgtaactat atgtcttagt catcttagtc aagaatgtag     4440
aagtaaagtg ataagatatg gaatttcctt taggtcacaa agagaaaaag aaaaatttta    4500
aagagctaag acaaacgcag caaaatcttt atatttaata atattctaaa catgggtgat    4560
gaacatacgg gtattcatta tactattctc tccacttttg agtatgtttg aaaatttagt    4620
aaaacaagtt ttaacacact gtagtctaac aagataaaat atcacactga acaggaaaaa    4680
ctggcatggt gtggtggctc acacttgtaa tcccagtgct ttgggaggct gagacaggag    4740
agttgcttga ggccaggagt tcaagaccga catggggaat gtagcaagac cccgtcccta    4800
caaaaaactt tgtaaaaatt tgccaggtat ggtggtgcat acctgtagtc ccagctactc    4860
gggaggcgga ggcagaagga atcacttgag cccaggagtt tgaggctgca gtgagctacg    4920
atcataccac agcactccag cgtggacaac agagtaagac cctatctcaa aaacaaaaca    4980
aaacaaaaca aacaaaaaaa accacaagaa aaactgctgg ctgatgcagc ggctcatgcc    5040
tgtaatccca gtattttggg aggcccaggt gggcgtatca cctgaggtca ggagttagag    5100
accagcctgg ccaacatggt gaaaccccat ctctactaaa aatacaaaat tagccaggca    5160
tgtggcacgc gcctgtagtc ccagttactg ggaggctgaa gcaggaggat cacctgagcc    5220
cgggaggtgg aggttgcagt gagccgagat cacaccactg cactccagcc tgggtgacac    5280
agcaataccc tacctcaaaa taaaaagaa aagaaaaga aaagttgctg tccccgctac     5340
cccaatccca aatccaaaca gcctctctca tctcacagta aggggaaaaa atcacccaaa    5400
aaagctaagt gatcttttga aaacccaaac tcttagaagt ctaagattat tatagtcaac    5460
tcatgaagtg tcatcataaa agatactcta atattattta agtagaacca catattggtt    5520
gtcttggtat gtctagcccc tggcatacaa aatatttaat aacactgata tggtacctgt    5580
gatgtgaaaa tgtactatga gtacagcttt ataaatacta tatatgtacc tatatacaga    5640
aaaaaataca acaaaatcat aaaagcactt atctttgaaa gaggagttac agcaattta    5700 tttagttctt tattgctttg ctatatattc taaattttt tcaatgaata tatatcactt    5760
ttaaaaaaat tcaatggtct ttcttataaa ttatcttttgg cagcatgcgt ttttatatat    5820
acatataaaa tgtatgggaa attttttaaag gatacattaa attaaagcaa aatatacaaa    5880
caaaaaatca gaatacaaaa agataaaaag attgggaagg gagggaggga gtaaggagga   5940
agggtgggtg ggtatagaga aatataccaa ataatggtaa gaagtgggt cttgacactt     6000 tctacacttt ttttaaataa aaaaaatttt tttctctctc tttttttttt ttagagacga     6060
agtctcgcta tgttgcccag gctggtcttg aactcctggg atcaagagat cctcctgcct     6120
cagcctccca aggtgcttgg attacaggt tgagccacca cgcctggtca ctttctacac      6180
tttaatatat atattttttc attttcaatg tcattttat tagttaattt ataatacca       6240 ttcaccatta tattcaaagt ctatttgaag aaataaacca gaaagaatga aatactctag    6300
ctcacatgct attcaatact aaattacctt tcaaatcaca ttcaagaagc tgatgattta    6360
```

```
agctttggcg gtttccaata aatattggtc aaaccataat taaatctcaa tatatcagtt    6420
agtacctatt gagcatctcc ttttacaacc taagcattgt attaggtgct taaatacaag    6480
cagcttgact tttaatacat ttaaaaatac atatttaaga cttaaaatct tatttatgga    6540
attcagttat attttgaggt ttccagtgct gagaaatttg aggtttgtgc tgtctttcag    6600
tccccaaagc tcagttctga gttctcagac tttggtggaa cttcatgtat tgtcaggttg    6660
gcccgtaata cctgtgggac aacttcagcc cctgtgcaca tggccaggag gctggttgca    6720
aacattttca ggtaggtgga ccaggacatg cccctggtca tggccaggtg gaggcatagt    6780
gctatacagc aggcagaagt caatattgat ttgttttttaa agaaacatgt actactttca    6840
taagcagaaa aaatttctat tcttggggga aaagattatg ccagatcctc taggattaaa    6900
tgctgatgca tctgctaaac cttcacatat cagaacatat ttactataga aagaatgaaa    6960
atgggacatt tgtgtgtcac ctatgtgaac attccaaaaa tattttacaa caactaagta    7020
ttttataaat tttatgaact gaaatttagt tcaagttcta ggaaaataca aaccttgcta    7080
gatattataa aaatgataca atatatattc atttcaggct catcagaata tatctgttat    7140
cacttgacaa gaatgaaaat gcaccatttt gtagtgcttt aaaatcagga agatccagag    7200
tactaaaaat gacttcttcc ttgaagctta ctcaccaact tcctcccagt tactcactgc    7260
ttctgccaca agcataaact aggacccagc cagaactccc ttgaaatata cacttgcaac    7320
gattactgca tctatcaaaa tggttcagtg cctggctaca ggttctgcag atcgactaag    7380
aatttgaaaa gtcttgttta tttcaaagga agcccatgtg aattctgccc agagttcatc    7440
ccagatatgc agtctaagaa tacagacaga tcagcagaga tgtattctaa aacaggaatt    7500
ctggcaatat aacaaattga tttccaatca aaacagattt acataccata cttatgtcaa    7560
gaagttgttt tgtttttattg catcctagat tttatttttt tgatttatgg tttactttaa    7620
gcataaaaaa tttgtcaata caactcttcc caaaaggcat aaacaaaaat tcataaaact    7680
tgcatcactt gagatacttc aggtatgaat tcacaacttt gttacaactt actatatata    7740
tgcacacata tatatatatt tgggtatatt ggggggggttc taatttaaga aatgcataat    7800
tggctataga cagacagttg tcagaacttg gcaatgggta cgtgcaggtt cattatacca    7860
agtctacttg tagttgttca aaatgtatca taatacaagg ccgggcgagg tcgtcacgcc    7920
tgtaatccca gcattttggg aggctaaggc aggaggattg cttgaggtca ggagtttgtg    7980
accagcctgg gcaacagagc aagaccctgt ctccaaaaag aaaaaaaata atttttaca    8040 aaataaaaac aaaatgtatc atcagacgaa attaaataag aggcaattca tttaaatgac    8100
aacttttccc agcttgacat ttaacaaaaa gtctaagtcc tcttaattca tatttaatga    8160
tcaaatatca aatactaatt tttttttttt ttttttttt gagacggagt ctcgctctgt    8220
cgcccaggct ggagtgcagt ggcgcgatcc tggctcactg caagctccgc ctcccgggtt    8280
cacgccattc tcctgcctca gcctcccgag tagctgggat tacagacatg cgccaccacg    8340
cccggctaat tttgtatttt tagtagagat ggggtttctc catgttggtc aggctggtct    8400
tgaatttccc acctcaggtg atctgcctgc ctcagcctca caaagcagta gctgggacta    8460
caggcaccca ccaccacact tggttaattc ttttgtattt tttttgtaaa gacgggattt    8520
caccatgtta gccaggatgg tctcgatctc ctgatctcat gatccgcccg cctcagcctc    8580
ccaaagtgct gggattacag gcgtgagcca ccccgcccgg ccatcaaata ctaattctta    8640
aatggtaagg acccactatt cagaacctgt atccttatca ctaatatgca aatatttatt    8700
```

```
gaatacttac tatgtcatgc atactagaga gagttagata aatttgatac agctaccctc    8760
acagaactta cagtgtaata gatggcatga catgtacatg agtaactgtg aacagtgtta    8820
aattgctatt taaaaaaaaa gacggctggg cgctgtggct catgcctgta atcccagcac    8880
tttgggaggc caaggcaagt tgatcgctcg aggtcaagag ttcgagacca gcctggccaa    8940
cgtggtaaaa ccccgtctct actaaaaata caaaaaaaaa attagccagg catggtggca    9000
caggcctgta atcccagcta ctagggaggc tgagacatgg agaactgctt gaatccagga    9060
ggcagaggtt acagtgagcc gagatcatac cactacactc cagcctgagt gacagagcga    9120
gactcctgtc taaaaaaaaa aaaaaaaaaa aagatacagg ttaagtgtta tggtagttga    9180
agagagaact caaactctgt ctcagaagcc tcacttgcat gtggaccact gatatgaaat    9240
aatataaata ggtataattc aataaatagg aacttcagtt ttaatcatcc caaacaccaa    9300
aacttcctat caaacaggtc caataaactc aatctctata agagctagac agaaatctac    9360
ttggtggcct ataatcttat tagcccttac ttgtcccatc tgatattaat taaccccatc    9420
taatatggat tagttaacaa tccagtggct gctttgacag gaacagttgg agagagttgg    9480
ggattgcaac atattcaatt atacaaaaat gcattcagca tctaccttga ttaaggcagt    9540
gtgcaacaga atttgcagga gagtaaaaga atgattataa atttacaacc cttaaagagc    9600
tatagctggg cgtggtggct catgcctgta aatcccagca cttgggagg ctgaggcggg    9660
tggatcacct gaggccagaa gttcaagacc agcctagcca acatggcgaa accctgtctc    9720
tacaaaaaat acaaaaatta gccgggtgtg gtggcacgtg cctgtagtcc cagttacttg    9780
ggaggccgag gcaggagaat cgcttgaacc taggaggtgg aggctgcagt gagccgagat    9840
tgtgccactg cactccactt cagcctgggc gacaagagca agactccgtc acaaaaaaaa    9900
aaaaaaaaaa aaagcttaaa atctagtggg aaaggcatat atacatacaa ctaactgtat    9960
agcataataa agctcataat ctgtaacaaa atctaattcg acaagcccag aaacttgtga   10020
tttaccaaaa acagttatat atacacaaaa agtaaaccta gaacccaaag ttacccagca   10080
ccaatgattc tctccctaag cagtatcaag tttaaagcag tgattacatt ctactgccta   10140
gattgtaaac tgagtaaagg agaccagcac ctttctgcta ctgaactagc acagccgtgt   10200
aaaccaacaa ggcaatggca gtgcccaact ttctgtatga atataagtta catctgtttt   10260
attatttgtg acttggtgtt gcatgtggtt attatcaaca ccttctgaaa gaacaactac   10320
ctgctcaggc tgccataaca aaataccaca gactgagtga cttaacagaa acttatttct   10380
cacagttttg gaggctggga agtccaaaat taaggtacct gcaaggtagg tttcaatctc   10440
aggcctcttc tttggcttga aggtcttcta actgtgtgct cacatgacct cttctaacaa   10500
gctctctggt gtctcttttt ttttttttt cttttttgag acagagtctc actctgtcac   10560
ccaggctgga gtacagtggc acaatctggg ctcactgcaa cctccaactc ccgggttcaa   10620
gtgattctca tgcctcaccc tcccgagtag cttggatgac aggagcccgc taccacaccc   10680
agctaatttt tgtattttta gtagagatgg tgtttcacta cattggccag gctggtctca   10740
aactcctgac ctcgtgatcc acccaccttg gcctcccaaa gtgctgggat tacaggtgtg   10800
agccactgcg cccgtcctgg tgtcttttca tataagggca ctaatccaat cagacctggg   10860
cccggcgcgc aattaaccct cactaaaggg aacaaaagct ggagctccac cgcggtggcg   10920
gccgctctag aactagtgga tcgggcccga gctctcgcga ccgggctgca ggaattcgat   10980
cgcgtgctag ctgcgctgtc ggggccaggc cgggctccca gtggattcgc gggcacagac   11040
gcccaggacc gcgcttccca cgtggcggag ggactgggga cccgggcacc cgtcctgccc   11100
```

```
cttcaccttc cagctccgcc tcctccgcgc ggaccccgcc ccgtcccgac ccctcccggg    11160
tccccggccc agcccctcc gggccctccc agccctccc cttcctttcc gcggcccgc       11220 cctctcctcg cggcgcgagt ttcaggcagc gctgcgtcct gctgcgcacg tgggaagccc    11280
tggcctggcg gatgtgtgac atacacgacg ccaaaagatt ttgttccagc tcctgccacc    11340
tccgctacgc gagagattaa ccacccacga tggccgccaa agtgcatgtt gatattgagg    11400
ctgacagccc attcatcaag tctttgcaga aggcatttcc gtcgttcgag gtggagtcat    11460
tgcaggtcac accaaatgac catgcaaatg ccagagcatt ttcgcacctg gctaccaaat    11520
tgatcgagca ggagactgac aaagacacac tcatcttgga tatcggcagt gcgccttcca    11580
ggagaatgat gtctacgcac aaataccact gcgtatgccc tatgcgcagc gcagaagacc    11640
ccgaaaggct cgtatgctac gcaaagaaac tggcagcggc ctccgggaag gtgctggata    11700
gagagatcgc aggaaaaatc accgacctgc agaccgtcat ggctacgcca gacgctgaat    11760
ctcctacctt ttgcctgcat acagacgtca cgtgtcgtac ggcagccgaa gtggccgtat    11820
accaggacgt gtatgctgta catgcaccaa catcgctgta ccatcaggcg atgaaaggtg    11880
tcagaacggc gtattggatt gggtttgaca ccaccccgtt tatgtttgac gcgctagcag    11940
gcgcgtatcc aacctacgcc acaaactggg ccgacgagca ggtgttacag gccaggaaca    12000
taggactgtg tgcagcatcc ttgactgagg gaagactcgg caaactgtcc attctccgca    12060
agaagcaatt gaaaccttgc gacacagtca tgttctcggt aggatctaca ttgtacactg    12120
agagcagaaa gctactgagg agctggcact taccctccgt attccacctg aaaggtaaac    12180
aatcctttac ctgtaggtgc gataccatcg tatcatgtga agggtacgta gttaagaaaa    12240
tcactatgtg ccccggcctg tacgtaaaa cggtagggta cgccgtgacg tatcacgcgg    12300
agggattcct agtgtgcaag accacagaca ctgtcaaagg agaaagagtc tcattccctg    12360
tatgcaccta cgtcccctca accatctgtg atcaaatgac tggcatacta gcgaccgacg    12420
tcacaccgga ggacgcacag aagttgttag tgggattgaa tcagaggata gttgtgaacg    12480
gaagaacaca gcgaaacact aacacgatga agaactatct gcttccgatt gtggccgtcg    12540
catttagcaa gtgggcgagg gaatacaagg cagaccttga tgatgaaaaa cctctgggtg    12600
tccgagagag gtcacttact tgctgctgct tgtgggcatt taaaacgagg aagatgcaca    12660
ccatgtacaa gaaaccagac acccagacaa tagtgaaggt gccttcagag tttaactcgt    12720
tcgtcatccc gagcctatgg tctacaggcc tcgcaatccc agtcagatca cgcattaaga    12780
tgcttttggc caagaagacc aagcgagagt taatacctgt tctcgacgcg tcgtcagcca    12840
gggatgctga acaagaggag aaggagaggt tggaggccga gctgactaga gaagccttac    12900 caccctcgt ccccatcgcg ccggcggaga cgggagtcgt cgacgtcgac gttgaagaac    12960
tagagtatca cgcaggtgca ggggtcgtgg aaacacctcg cagcgcgttg aaagtcaccg    13020
cacagccgaa cgacgtacta ctaggaaatt acgtagttct gtccccgcag accgtgctca    13080
agagctccaa gttggccccc gtgcaccctc tagcagagca ggtgaaaata ataacacata    13140
acgggagggc cggcggttac caggtcgacg gatatgacgg cagggtccta ctaccatgtg    13200
gatcggccat tccggtccct gagtttcaag ctttgagcga gagcgccact atggtgtaca    13260
acgaaaggga gttcgtcaac aggaaactat accatattgc cgttcacgga ccgtcgctga    13320
acaccgacga ggagaactac gagaaagtca gagctgaaag aactgacgcc gagtacgtgt    13380
tcgacgtaga taaaaaatgc tgcgtcaaga gagaggaagc gtcgggtttg gtgttggtgg    13440
```

```
gagagctaac caaccccccg ttccatgaat tcgcctacga agggctgaag atcaggccgt    13500
cggcaccata taagactaca gtagtaggag tctttggggt tccgggatca ggcaagtctg    13560
ctattattaa gagcctcgtg accaaacacg atctggtcac cagcggcaag aaggagaact    13620
gccaggaaat agttaacgac gtgaagaagc accgcgggaa gggacaagt agggaaaaca    13680 gtgactccat cctgctaaac gggtgtcgtc gtgccgtgga catcctatat gtggacgagg    13740
ctttcgcttg ccattccggt actctgctgg ccctaattgc tcttgttaaa cctcggagca    13800
aagtggtgtt atgcggagac cccaagcaat gcggattctt caatatgatg cagcttaagg    13860
tgaacttcaa ccacaacatc tgcactgaag tatgtcataa aagtatatcc agacgttgca    13920
cgcgtccagt cacggccatc gtgtctacgt tgcactacgg aggcaagatg cgcacgacca    13980
acccgtgcaa caaacccata atcatagaca ccacaggaca gaccaagccc aagccaggag    14040
acatcgtgtt aacatgcttc cgaggctggg caaagcagct gcagttggac taccgtggac    14100
acgaagtcat gacagcagca gcatctcagg gcctcacccg caaggggta tacgccgtaa    14160 ggcagaaggt gaatgaaaat cccttgtatg cccctgcgtc ggagcacgtg aatgtactgc    14220
tgacgcgcac tgaggatagg ctggtgtgga aaacgctggc cggcgatccc tggattaagg    14280
tcctatcaaa cattccacag ggtaacttta cggccacatt ggaagaatgg caagaagaac    14340
acgacaaaat aatgaaggtg attgaaggac cggctgcgcc tgtggacgcg ttccagaaca    14400
aagcgaacgt gtgttgggcg aaaagcctgg tgcctgtcct ggacactgcc ggaatcagat    14460
tgacagcaga ggagtggagc accataatta cagcatttaa ggaggacaga gcttactctc    14520
cagtggtggc cttgaatgaa atttgcacca agtactatgg agttgacctg gacagtggcc    14580
tgttttctgc cccgaaggtg tccctgtatt acgagaacaa ccactgggat aacagacctg    14640
gtggaaggat gtatggattc aatgccgcaa cagctgccag gctggaagct agacatacct    14700
tcctgaaggg gcagtggcat acgggcaagc aggcagttat cgcagaaaga aaaatccaac    14760
cgctttctgt gctggacaat gtaattccta tcaaccgcag gctgccgcac gccctggtgg    14820
ctgagtacaa gacggttaaa ggcagtaggg ttgagtggct ggtcaataaa gtaagagggt    14880
accacgtcct gctggtgagt gagtacaacc tggctttgcc tcgacgcagg gtcacttggt    14940
tgtcaccgct gaatgtcaca ggcgccgata ggtgctacga cctaagttta ggactgccgg    15000
ctgacgccgg caggttcgac ttggtctttg tgaacattca cacggaattc agaatccacc    15060
actaccagca gtgtgtcgac cacgccatga gctgcagat gcttggggga gatgcgctac    15120
gactgctaaa acccggcggc atcttgatga gagcttacgg atacgccgat aaaatcagcg    15180
aagccgttgt ttcctcctta agcagaaagt tctcgtctgc aagagtgttg cgcccggatt    15240
gtgtcaccag caatacagaa gtgttcttgc tgttctccaa ctttgacaac ggaaagagac    15300
cctctacgct acaccagatg aataccaagc tgagtgccgt gtatgccgga gaagccatgc    15360
acacggccgg gtgtgcacca tcctacagag ttaagagagc agacatagcc acgtgcacag    15420
aagcggctgt ggttaacgca gctaacgccc gtggaactgt aggggatggc gtatgcaggg    15480
ccgtggcgaa gaaatggccg tcagccttta agggagcagc aacaccagtg gcacaatta    15540 aaacagtcat gtgcggctcg taccccgtca tccacgctgt agcgcctaat ttctctgcca    15600
cgactgaagc ggaaggggac cgcgaattgg ccgctgtcta ccgggcagtg gccgccgaag    15660
taaacagact gtcactgagc agcgtagcca tcccgctgct gtccacagga gtgttcagcg    15720
gcggaagaga taggctgcag caatcccctca accatctatt cacagcaatg gacgccacgg    15780
acgctgacgt gaccatctac tgcagagaca aaagttggga gaagaaaatc caggaagcca    15840
```

```
ttgacatgag gacggctgtg gagttgctca atgatgacgt ggagctgacc acagacttgg   15900
tgagagtgca cccggacagc agcctggtgg gtcgtaaggg ctacagtacc actgacgggt   15960
cgctgtactc gtactttgaa ggtacgaaat tcaaccaggc tgctattgat atggcagaga   16020
tactgacgtt gtggcccaga ctgcaagagg caaacgaaca gatatgccta tacgcgctgg   16080
gcgaaacaat ggacaacatc agatccaaat gtccggtgaa cgattccgat tcatcaacac   16140
ctcccaggac agtgccctgc ctgtgccgct acgcaatgac agcagaacgg atcgcccgcc   16200
ttaggtcaca ccaagttaaa agcatggtgg tttgctcatc ttttcccctc ccgaaatacc   16260
atgtagatgg ggtgcagaag gtaaagtgcg agaaggttct cctgttcgac ccgacggtac   16320
cttcagtggt tagtccgcgg aagtatgccg catctacgac ggaccactca gatcggtcgt   16380
tacgagggtt tgacttggac tggaccaccg actcgtcttc cactgccagc gataccatgt   16440
cgctacccag tttgcagtcg tgtgacatcg actcgatcta cgagccaatg gctcccatag   16500
tagtgacggc tgacgtacac cctgaacccg caggcatcgc ggacctggcg gcagatgtgc   16560
accctgaacc cgcagaccat gtggacctcg agaacccgat tcctccaccg cgcccgaaga   16620
gagctgcata ccttgcctcc cgcgcggcgg agcgaccggt gccggcgccg agaaagccga   16680
cgcctgcccc aaggactgcg tttaggaaca agctgccttt gacgttcggc gactttgacg   16740
agcacgaggt cgatgcgttg gcctccggga ttactttcgg agacttcgac gacgtcctgc   16800
gactaggccg cgcgggtgca tatattttct cctcggacac tggcagcgga catttacaac   16860
aaaaatccgt taggcagcac aatctccagt gcgcacaact ggatgcggtc caggaggaga   16920
aaatgtaccc gccaaaattg gatactgaga gggagaagct gttgctgctg aaaatgcaga   16980
tgcacccatc ggaggctaat aagagtcgat accagtctcg caaagtggag aacatgaaag   17040
ccacggtggt ggacaggctc acatcggggg ccagattgta cacgggagcg gacgtaggcc   17100
gcataccaac atacgcggtt cggtaccccc gccccgtgta ctcccctacc gtgatcgaaa   17160
gattctcaag ccccgatgta gcaatcgcag cgtgcaacga ataccctatcc agaaattacc   17220 caacagtggc gtcgtaccag ataacagatg aatacgacgc atacttggac atggttgacg   17280
ggtcggatag ttgcttggac agagcgacat tctgcccggc gaagctccgg tgctacccga   17340
aacatcatgc gtaccaccag ccgactgtac gcagtgccgt cccgtcaccc tttcagaaca   17400
cactacagaa cgtgctagcg gccgccacca agagaaactg caacgtcacg caaatgcgag   17460 aactaccccac catggactcg gcagtgttca acgtggagtt cttcaagcgc tatgcctgct   17520
ccggagaata ttgggaagaa tatgctaaac aacctatccg gataaccact gagaacatca   17580
ctacctatgt gaccaaattg aaaggcccga agctgctgc cttgttcgct aagacccaca   17640
acttggttcc gctgcaggag gttcccatgg acagattcac ggtcgacatg aaacgagatg   17700
tcaaagtcac tccagggacg aaacacacag aggaaagacc caaagtccag gtaattcaag   17760
cagcggagcc attggcgacc gcttacctgt gcggcatcca cagggaatta gtaaggagac   17820
taaatgctgt gttacgccct aacgtgcaca cattgtttga tatgtcggcc gaagactttg   17880
acgcgatcat cgcctctcac ttccacccag agacccggt tctagagacg gacattgcat   17940
cattcgacaa aagccaggac gactccttgg ctcttacagg tttaatgatc ctcgaagatc   18000
tagggtggga tcagtacctg ctggacttga tcggaggcagc ctttgggaa atatccagct   18060 gtcacctacc aactgcacg cgcttcaagt tcggagctat gatgaaatcg ggcatgtttc   18120
tgactttgtt tattaacact gttttgaaca tcaccatagc aagcagggta ctggagcaga   18180
```

```
gactcactga ctccgcctgt gcggccttca tcggcgacga caacatcgtt cacggagtga   18240
tctccgacaa gctgatggcg gagaggtgcg cgtcgtgggt caacatggag gtgaagatca   18300
ttgacgctgt catgggcgaa aaaccccat attttttgtgg gggattcata gtttttgaca   18360
gcgtcacaca gaccgcctgc cgtgtttcag acccacttaa gcgcctgttc aagttgggta   18420
agccgctaac agctgaagac aagcaggacg aagacaggcg acgagcactg agtgacgagg   18480
ttagcaagtg gttccggaca ggcttggggg ccgaactgga ggtggcacta acatctaggt   18540
atgaggtaga gggctgcaaa agtatcctca tagccatggc caccttggcg agggacatta   18600
aggcgtttaa gaaattgaga ggacctgtta tacacctcta cggcggtcct agattggtgc   18660
gttaatacac agaattctga ttggatctcg aggtcgacgg tatcgataag cttgggctgc   18720
aggtcgatcg actctagagg atcgatcccc accatgggtc aatcacgcta cctcctcttt   18780
ttggccaccc ttgccctcct aaaccacctc agtttggcca gggtcattcc agtctctgga   18840
cctgccaggt gtcttagcca gtcccgaaac ctgctgaaga ccacagatga catggtgaag   18900
acggccagag aaaaactgaa acattattcc tgcactgctg aagacatcga tcatgaagac   18960
atcacacggg accaaaccag cacattgaag acctgtttac cactggaact acacaagaac   19020
gagagttgcc tggctactag agagacttct tccacaacaa gagggagctg cctgccccca   19080
cagaagacgt ctttgatgat gaccctgtgc cttggtagca tctatgagga cttgaagatg   19140
taccagacag agttccaggc catcaacgca gcacttcaga atcacaacca tcagcagatc   19200
attctagaca agggcatgct ggtggccatc gatgagctga tgcagtctct gaatcataat   19260
ggcgagactc tgcgccagaa acctcctgtg ggagaagcag acccttacag agtgaaaatg   19320
aagctctgca tcctgcttca cgccttcagc acccgcgtcg tgaccatcaa cagggtgatg   19380
ggctatctga gctccgcctg agaattccgc ccctctccct ccccccccc taacgttact   19440
ggccgaagcc gcttggaata aggccggtgt gcgtttgtct atatgttatt ttccaccata   19500
ttgccgtctt ttggcaatgt gagggcccgg aaacctggcc ctgtcttctt gacgagcatt   19560
cctaggggtc tttcccctct cgccaaagga atgcaaggtc tgttgaatgt cgtgaaggaa   19620
gcagttcctc tggaagcttc ttgaagacaa acaacgtctg tagcgaccct ttgcaggcag   19680
cggaaccccc cacctggcga caggtgcctc tgcggccaaa agccacgtgt ataagataca   19740
cctgcaaagg cggcacaacc ccagtgccac gttgtgagtt ggatagttgt ggaaagagtc   19800
aaatggctct cctcaagcgt attcaacaag gggctgaagg atgcccagaa ggtaccccat   19860
tgtatgggat ctgatctggg gcctcggtgc acatgcttta catgtgttta gtcgaggtta   19920
aaaaacgtct aggccccccg aaccacgggg acgtggtttt cctttgaaaa acacgatgat   19980
aatatgccaa caaccatggg tcctcagaag ctaaccatct cctggtttgc catcgttttg   20040
ctggtgtctc cactcatggc catgtgggag ctggagaaag acgtttatgt tgtagaggtg   20100
gactggactc ccgatgcccc tggagaaaca gtgaacctca cctgtgacac gcctgaagaa   20160
gatgacatca cctggaccct agaccagaga catggagtca taggctctgg aaagaccctg   20220
accatcactg tcaaagagtt tctagatgct ggccagtaca cctgccacaa aggaggcgag   20280
actctgagcc actcacatct gctgctccac aagaaggaaa atggaatttg gtccactgaa   20340
atttttaaaaa atttcaaaaa caagactttc ctgaagtgtg aagcaccaaa ttactccgga   20400
cggttcacgt gctcatggct ggtgcaaaga acatggact tgaagttcaa catcaagagc   20460
agtagcagtt cccctgactc tcgggcagtg acatgtggaa tggcgtctct gtctgcagag   20520
aaggtcacac tggaccaaag ggactatgag aagtattcag tgtcctgcca ggaggatgtc   20580
```

```
acctgcccaa ctgccgagga gaccctgccc attgaactgg cgttggaagc acggcagcag    20640
aataaatatg agaactacag caccagcttc ttcatcaggg acatcatcaa accagacccg    20700
cccaagaact tgcagatgaa gcctttgaag aactcacagg tggaggtcag ctgggagtac    20760
cctgactcct ggagcactcc ccattcctac ttctccctca agttctttgt tcgaatccag    20820
cgcaagaaag aaaagatgaa ggagacagag gaggggtgta accagaaagg tgcgttcctc    20880
gtagagaaga catctaccga agtccaatgc aaaggcggga atgtctgcgt gcaagctcag    20940
gatcgctatt acaattcctc atgcagcaag tgggcatgtg ttccctgcag ggtccgatcc    21000
tagaattcat tgatccacta ggatcccggg taattaattg aattacatcc ctacgcaaac    21060
gttttacggc cgccggtggc gcccgcgccc ggcggcccgt ccttggccgt tgcaggccac    21120
tccggtggct cccgtcgtcc ccgacttcca ggcccagcag atgcagcaac tcatcagcgc    21180
cgtaaatgcg ctgacaatga gacagaacgc aattgctcct gctaggcctc ccaaaccaaa    21240
gaagaagaag acaaccaaac caaagccgaa aacgcagccc aagaagatca acggaaaaac    21300
gcagcagcaa aagaagaaag acaagcaagc cgacaagaag aagaagaaac ccggaaaaag    21360
agaaagaatg tgcatgaaga ttgaaaatga ctgtatcttc gtatgcggct agccacagta    21420
acgtagtgtt tccagacatg tcgggcaccg cactatcatg ggtgcagaaa atctcgggtg    21480
gtctgggggc cttcgcaatc ggcgctatcc tggtgctggt tgtggtcact tgcattgggc    21540
tccgcagata agttaggta ggcaatggca ttgatatagc aagaaaattg aaaacagaaa    21600
aagttagggt aagcaatggc atataaccat aactgtataa cttgtaacaa agcgcaacaa    21660
gacctgcgca attggccccg tggtccgcct cacggaaact cggggcaact catattgaca    21720
cattaattgg caataattgg aagcttacat aagcttaatt cgacgaataa ttggattttt    21780
attttatttt gcaattggtt tttaatattt ccaaaaaaaa aaaaaaaaaa aaaaaaaaaa    21840
aaaaaaaaaa aaaaaaaaaa aaaaaaaaaa aaaaaaaaaa aactagatcc tcgaatcaag    21900
cttatcgata ccgtcgacta gagtcggggc ggccggccgc ttcgagcaga catgataaga    21960
tacattgatg agtttggaca aaccacaact agaatgcagt gaaaaaaatg ctttatttgt    22020
gaaatttgtg atgctattgc tttatttgta accattataa gctgcaataa acaagttaac    22080
aacaacaatt gcattcattt tatgtttcag gttcagggg aggtgtggga ggttttttaa    22140
agcaagtaaa acctctacaa atgtggtaaa atcgataagg atctcgacct cgagggggg    22200 cccggtaccc aattcgccct atagtgagtc gtattacgcg cgccctgca gggggccctg    22260 taccgggctc tgcctgaggc tctggctgcc cagcaggctg aagctggggt tgttggccag    22320
gggcacttgt gttcccatcg cagcgggcac ttgtgcctcc caatcagatg gcctctgaag    22380
gcaggcctgg ccagaaggtg agtgctgctg aacgctatta tccacttggc tgagggtgt    22440 tttccccgaa actgctgtgg tcacagctgc tgccgctgtg acccatgcag cattgttgaa    22500
cgcagtgggc attcttggca cactaggccg tctgagctgg tggggactca aggactgggt    22560
gcccagggag ctgggacaga acccaggcag gggcacttct ggtggggtgg ccttgggct    22620 ctgcatatgc tggcagacag agtcaagtct gcccagggga gtctggcctg agtgtgagag    22680
gatgggacac tggggctgg aggtgaaaat tccttgccgc ttccccagag ttggtgagat    22740
cactcccatg ccctcgcagc tctggtgcct ggtgagtggg atcattcctg gactcagatt    22800
gttctgaaga agcccagttc tgggtggcat caagtgcttg ctagatgggg ggcttgcctt    22860
gatccggcta cacttggagg tgacttgttc ttggacggct acatacagaa agagagaagt    22920
```

```
ggggatgagt tccaaaggca tcctcgactt cggctgtggc caccggaggg tagctcctgg    22980
cccaacacgg acttctcacc tcccgccctt ggctctctac tgagctcccc cctgctcccc    23040
aattcctcgc cattccccct atttctctgc cctcagcctg gactgcagtt cttctgggaa    23100
gctgccccaa ctccctaggt ctgtgctcac caagagcaga tcacactgga ctgaaatgcc    23160
agctgatttg tctcttcaag aaaattggaa gctcctggag gtcagggtcc atgtctgctt    23220
ttacactcag tgctctgtat gcaggcctgg cactgcccac cctttgacag gtggtgcata    23280
ttttgtagaa ggaaggaagg ggccaggtgg ggtgggctgg gctggtggcg ggagctagct    23340
cagcctctta gattctctac ccgatggatg tgacctggga cagcaagtga gtgtggtgag    23400
tgagtgcaga cggtgctttg ttcccctctt gtctcatagc ctagatggcc tctgagccca    23460
gatctggggc tcagacaaca tttgttcaac tgaacggtaa tgggtttcct ttctgaaggc    23520
tgaaatctgg gagctgacat tctggactcc ctgagttctg aagagcctgg ggatggagag    23580
acacggagca gaagatggaa ggtagagtcc caggtgccta agatggggaa tacatctccc    23640
ctcattgtca tgagagtcca ctctagctga tatctactgt ggccaatatc taccggtact    23700
tttttggggt ggacactgag tcatgcagca gtcttatggt ttacccaagg tcaggtaggg    23760
gagacagtgc agtcagagca caagcccagt gtgtctgacc cacccaagaa tccatgctcg    23820
tatctacaaa aatgattttt tctcttgtaa tggtgcctag gttcttttat tatcatggca    23880
tgtgtatgtt tttcaactag gttacaatct ggccttataa ggttaacctc ctggaggcca    23940
ccagccttcc tgaaacttgt ctgtgctgtc cctgcaactg gagtgtgcct gatgtggcac    24000
tccagcctgg acaagtggga cacagactcc gctgttatca ggcccaaaga tgtcttccat    24060
aagaccagaa gagcaatggt gtagaggtgt catgggctac aataaagatg ctgacctcct    24120
gtctgagggc aagcagcctc ttctggccct cagacaaatg ctgagtgttc ccaagactac    24180
cctcggcctg gtccaatctc atcccactgg tgcgtaaggg ttgctgaact catgacttct    24240
tggctagcct gcaacctcca cggagtggga actacatcag gcattttgct aactgctgta    24300
tcctaggcca ataaatgttg atcacattta tagctgccat ggtagggtgg ggaccccctgc   24360
tatctatctg tggaggctct gggagcccct gacacaaact ttctgaagca gagcctcccc    24420
aacccctttt ccattcccta tacctgacag atggcccagg aacccattag aaatggaagg    24480
tcactgcagc agtatgtgaa tgtgcgtgtg ggagaagggc aggatcagag ccctgggggt    24540
gtggcagccc ccaagtgatt ctaatccaga tcctagggtt gtttccctgt cccattgaaa    24600
tagctgcttt aaggggcctg actcagggaa atcagtctct tgaattaagt ggtgattttg    24660
gagtcattta gaccaggcct tcaattggga tcctgctctt agagttggat gaattattta    24720
actgattttc agatctcctc tttctcaatg cttttcagaag cacagtaact gcttactctg    24780
aaatgaattc tcaccccact tccacatatg caccccttgc ccaccccttt gggaacactg    24840
gccttaactg cttaccttca aatggactca tctgttggga gatatatgca ttctgccgtt    24900
caggggtcat tgccataaga cctgatctct gttcctcttg ctaaacagaa gatgaaaaag    24960
acaaattaga ttcagctac caattaataa ttagccttag gatcgctgcg tggggaccta    25020
ggacttggct ttggtgcagc agaaagcatg aataaacaca ccagcataca ctcgcatgca    25080
tgccccaccc tctcgagcaa aattccacag gtataaataa agtaagattc tgcacctggg    25140
ttaaaaacac aactgcaaca gcatagaatg gggcaggaga gacagaactt aatagcaaga    25200
gcacacagaa aaaagtttta ggcatttttgg atgtccatct gctcaggatg ggtcagcagt    25260
gagatgcggt caccaaaaga acaaatgtaa cattaggctg cattaataga agcagagtat    25320
```

```
gtagaaggag ggaggtgaca gtcctatgct aactctgcct tggccagact atacccacag    25380
gagtctgggc atgccagtct cagggagacc cagacagact ggctgcattc agaggatggt    25440
aagtaatgag agtggggatt ggacttcaaa ctacccagac aaagaatggc tgagcaagcc    25500
aaggatgctg tggctggggc agagcagact gtgggctatg tagtggtgga tacctagcct    25560
ctgcagggct gtcataggga aaggacattg agaagaggac tgaggcttgt tcctggtggt    25620
cctggcatga acggccagat gatcacatgg tcaggtggac acagtctcca acactgggag    25680
tagccaaaca cttactgcca acctcccgcc cttctcctga ctagttgcag cataggcaat    25740
tgggaggagc ttcctgtctc catctgaaag ctggctgggt gggcagggggg aggagcgagc    25800
caagtttcaa ggccgcagtt tcagcactca gtctgggatc ggctcaagga gcaaagggga    25860
agaacatagc caggagggaa taacatgaag gcccccagac ccagaaaagg catgacttgc    25920
tctgagaccc tcagccggtt ggtgtcaggt tgtgactcgg atccaggtct gactcccagt    25980
ccagtgcttg aagcctcacc ccacacagtg aggggagccc ggccatctct gctcaactgc    26040
tgccatctct ctcccttct caaccaccaa ggcagctctg tctgggagca caagctccaa    26100
gtccactttc tggtctgtgt ccccccccaag atgccagagg acttgcctct acaacacggg    26160
ctgcccgtgc agtgcctgct tttccagcaa agggcttctg ggaacccttc tctgcactca    26220
gtggggctgg tgggagtggg gcggggtagc gaccagtgc ttgggactgt gcccagctct    26280
caggcctggc agcagttcct ggccttggtt cctgccaagg cagagaggac aaacacatgg    26340
caccgggaag actacaccag aagcgattcc accagactgg ggtttgcttt tctatcccgc    26400
ccttagcctg cttcctgtcc tggtccctgc ctccccctcc actggagctg ccgtgtgggc    26460
agtgagggggc tgtttctcag ctgccctatg gagctgccct ctccctgcca aagcattggc    26520
aaggcggcaa ggggtgggg tgggatggg gggtgggatc tgccttctca agctctcatt    26580
atactgagca cgtctcaccc attattttat gtcatctagc aacacccccat gtggacactg    26640
aggagcatgg gggtcacatg accactgccc aaggccacac catccggatc tgcctgagat    26700
ggtcagggtt ggcagccatt tctgaaggca gtcctttcgc tttggctctt cttgtaccag    26760
tctcaggaca tcagggcaga agatctacag tccccagctt actgatgtga cagcagaggc    26820
tcagagaggt taaatgactt gcccaaggtg acacggctaa gaagtacagt atctcctaac    26880
tgcagaccag gtgcttctgc tgcttctggg gacagattcc tgcgtggctg gctaggtcta    26940
aacggtcctt aactccatcc ccaccggttg ctgcattagt ttcatcaaat aacacagttg    27000
tacagaggta ggggttcagg ggcaggggca gatggaggct ggagagtgtg actaaggaaa    27060
cagcagggga agtgcggtaa agtccgaagg gaggacgga aagagaaagc caagcccagg    27120
ggcgtgccag acaaaaggaa aggccacgcc ggggcagggc aggcttcagc gggtgctggg    27180
gcgtcttcat cccgggaagc acacattcca gaggaccccg gagtctaatg gaaaagctgg    27240
ccagcctatc actatggaaa ctgccaaggc cacacagcgc tgctgacacc cagcctgggt    27300
gccggtggcc agctctgcag gatcttcaag tctggggtgc caccagcaag cgacggtcct    27360
ccatgggctc ttcaccttac ggcagtgtcc agaggcaccg ccagtcctct gctcctatgc    27420
tggtcctgct gtccctggca aaaggagcca gagcattctc tccaggcctc ccgaggaggc    27480
tgcttccttt gttttgcaga tggaggctcc catcctttgt tctgaatcaa tgtgctccaa    27540
agataagccc caagaaaaca gttgttgcct tttgacactg acaattagaa tcgttggaaa    27600
atggagaaaa caggaaatgg caaatggttt cagtgaccag gaggaaaccg tgcctgaaag    27660
```

-continued

```
ttgctgctta gtgactggga cactcgcttt ctgctctctt atgaaggaca gcctaggccg    27720
tgtggccttt tataaacaaa gctatgaagg ggtcgtcaaa ttttctaggg ctgcaactgt    27780
ggcactacgt cctgttgtgc caggtgacac tgacaagcag cactgagttc tatgcaagcc    27840
caggtgtgct tctctcatgg tgaccccag  agaactaagg cccagctctt cctctgtcac    27900 accccctccca gccccactg  tcagacaagg gaccacattc acagacagtc tcagccaaga   27960
tggcaacctt ggaagtcctg gggatgcctt tctagaagct cgcgcccta  ggggccggcc    28020 ttaattaaat caagcttatc gataccgtcg agacctcgag ggggggcatc actccgccct    28080
aaaacctacg tcacccgccc cgttcccacg ccccgcgcca cgtcacaaac tccacccct    28140 cattatcata ttggcttcaa tccaaaataa ggtatattat tgatgatgtt t             28191
```

```
<210> SEQ ID NO 11
<211> LENGTH: 5844
<212> TYPE: DNA
<213> ORGANISM: Plasmid
<220> FEATURE:
<221> NAME/KEY: MCS
<222> LOCATION: (1)..(25)
<223> OTHER INFORMATION: Multiple cloning site
<220> FEATURE:
<221> NAME/KEY: AFPenhancer
<222> LOCATION: (26)..(820)
<223> OTHER INFORMATION: AFP enhancer
<220> FEATURE:
<221> NAME/KEY: AFPpro
<222> LOCATION: (828)..(1054)
<223> OTHER INFORMATION: AFP promoter

<400> SEQUENCE: 11
```

```
ggtaccgagc tcttacgcgt gctagaattc gcctgtcata cagctaataa ttgaccataa      60
gacaattaga tttaaattag ttttgaatct ttctaatacc aaagttcagt ttactgttcc     120
atgttgcttc tgagtggctt cacagactta tgaaaaagta acggaatca  gaattacatc     180 aatgcaaaag cattgctgtg aactctgtac ttaggactaa actttgagca ataacacaca    240
tagattgagg attgtttgct gttagcatac aaactctggt tcaaagctcc tctttattgc    300
ttgtcttgga aaatttgctg ttcttcatgg tttctctttt cactgctatc tatttttctc    360
aaccactcac atggctacaa taactgtctg caagcttatg attcccaaat atctatctct   420
agcctcaatc ttgttccaga agataaaaag tagtattcaa atgcacatca acgtctccac   480
ttggagggct taaagacgtt tcaacataca aaccggggag ttttgcctgg aatgtttcct   540
aaaatgtgtc ctgtagcaca tagggtcctc ttgttcctta aaatctaatt acttttagcc   600
cagtgctcat cccacctatg gggagatgag agtgaaaagg agcctgatt  aataattaca   660 ctaagtcaat aggcatagag ccaggactgt ttgggtaaac tggtcacttt atcttaaact   720
aaatatatcc aaaactgaac atgtacttag ttactaagtc tttgacttta tctcattcat   780
accactcagc tttatccagg ccacttattt gacagtctag ctagccccta gattttctgc    840
cccaaagagc tctgtgtcct tgaacataaa atacaaataa ccgctatgct gttaattatt   900
ggcaaatgtc ccattttcaa cctaaggaaa taccataaag taacagatat accaacaaaa   960
ggttactagt taacaggcat tgcctgaaaa gagtataaaa gaatttcagc atgattttcc   1020
atattgtgct tccaccactg ccaataacag gatcgggctc gagatctgcg atctaagtaa   1080
gcttggcatt ccggtactgt tggtaaagcc accatggaag acgccaaaaa cataagaaa    1140 ggcccggcgc cattctatcc gctggaagat ggaaccgctg gagagcaact gcataaggct   1200
atgaagagat acgccctggt tcctggaaca attgctttta cagatgcaca tatcgaggtg   1260
```

```
gacatcactt acgctgagta cttcgaaatg tccgttcggt tggcagaagc tatgaaacga  1320
tatgggctga atacaaatca cagaatcgtc gtatgcagtg aaaactctct tcaattcttt  1380
atgccggtgt tgggcgcgtt atttatcgga gttgcagttg cgcccgcgaa cgacatttat  1440
aatgaacgtg aattgctcaa cagtatgggc atttcgcagc ctaccgtggt gttcgtttcc  1500 aaaaagggg tgcaaaaaat tttgaacgtg caaaaaaagc tcccaatcat ccaaaaaatt  1560
attatcatgg attctaaaac ggattaccag ggatttcagt cgatgtacac gttcgtcaca  1620
tctcatctac ctcccggttt taatgaatac gattttgtgc cagagtcctt cgatagggac  1680
aagacaattg cactgatcat gaactcctct ggatctactg gtctgcctaa aggtgtcgct  1740
ctgcctcata gaactgcctg cgtgagattc tcgcatgcca gagatcctat ttttggcaat  1800
caaatcattc cggatactgc gattttaagt gttgttccat tccatcacgg ttttggaatg  1860
tttactacac tcggatattt tgatatgtgga tttcgagtcg tcttaatgta tagatttgaa  1920
gaagagctgt ttctgaggag ccttcaggat tacaagattc aaagtgcgct gctggtgcca  1980
accctattct ccttcttcgc caaaagcact ctgattgaca atacgatttt atctaattta  2040
cacgaaattg cttctggtgg cgctcccctc tctaaggaag tcggggaagc ggttgccaag  2100
aggttccatc tgccaggtat caggcaagga tatgggctca ctgagactac atcagctatt  2160
ctgattacac ccgaggggga tgataaaccg ggcgcggtcg gtaaagttgt tccatttttt  2220
gaagcgaagg ttgtggatct ggataccggg aaaacgctgg gcgttaatca aagaggcgaa  2280
ctgtgtgtga ggtcctat gattatgtcc ggttatgtaa acaatccgga agcgaccaac  2340
gccttgattg acaaggatgg atggctacat tctggagaca tagcttactg ggacgaagac  2400
gaacacttct tcatcgttga ccgcctgaag tctctgatta agtacaaagg ctatcaggtg  2460
gctcccgctg aattggaatc catcttgctc aacaccccca acatcttcga cgcaggtgtc  2520
gcaggtcttc ccgacgatga cgccggtgaa cttcccgccg ccgttgttgt tttggagcac  2580
ggaaagacga tgacggaaaa agagatcgtg gattacgtcg ccagtcaagt aacaaccgcg  2640
aaaaagttgc gcggaggagt tgtgtttgtg gacgaagtac cgaaaggtct taccggaaaa  2700
ctcgacgcaa gaaaaatcag agagatcctc ataaaggcca gaagggcgg aaagatcgcc  2760 gtgtaattct agagtcgggg cggccggccg cttcgagcag acatgataag atacattgat  2820
gagtttggac aaaccacaac tagaatgcag tgaaaaaaat gctttatttg tgaaatttgt  2880
gatgctattg ctttatttgt aaccattata agctgcaata acaagttaa caacaacaat  2940 tgcattcatt ttatgtttca ggttcagggg gaggtgtggg aggttttta aagcaagtaa  3000 aacctctaca aatgtggtaa aatcgataag gatccgtcga ccgatgccct tgagagcctt  3060
caacccagtc agctccttcc ggtgggcgcg gggcatgact atcgtcgccg cacttatgac  3120
tgtcttcttt atcatgcaac tcgtaggaca ggtgccggca gcgctcttcc gcttcctcgc  3180
tcactgactc gctgcgctcg gtcgttcggc tgcggcgagc ggtatcagct cactcaaagg  3240
cggtaatacg gttatccaca gaatcagggg ataacgcagg aaagaacatg tgagcaaaag  3300
gccagcaaaa ggccaggaac cgtaaaaagg ccgcgttgct ggcgtttttc cataggctcc  3360
gcccccctga cgagcatcac aaaaatcgac gctcaagtca gaggtggcga acccgacag  3420 gactataaag ataccaggcg tttccccctg gaagctccct cgtgcgctct cctgttccga  3480
ccctgccgct taccggatac ctgtccgcct ttctcccttc gggaagcgtg gcgctttctc  3540
aatgctcacg ctgtaggtat ctcagttcgg tgtaggtcgt tcgctccaag ctgggctgtg  3600
```

```
tgcacgaacc cccgttcag cccgaccgct gcgccttatc cggtaactat cgtcttgagt    3660
ccaacccggt aagacacgac ttatcgccac tggcagcagc cactggtaac aggattagca    3720
gagcgaggta tgtaggcggt gctacagagt tcttgaagtg gtggcctaac tacggctaca    3780
ctagaaggac agtatttggt atctgcgctc tgctgaagcc agttaccttc ggaaaaagag    3840
ttggtagctc ttgatccggc aaacaaacca ccgctggtag cggtggtttt tttgtttgca    3900
agcagcagat tacgcgcaga aaaaaggat ctcaagaaga tcctttgatc ttttctacgg    3960
ggtctgacgc tcagtggaac gaaaactcac gttaagggat tttggtcatg agattatcaa    4020
aaaggatctt cacctagatc cttttaaatt aaaaatgaag ttttaaatca atctaaagta    4080
tatatgagta aacttggtct gacagttacc aatgcttaat cagtgaggca cctatctcag    4140
cgatctgtct atttcgttca tccatagttg cctgactccc cgtcgtgtag ataactacga    4200
tacgggaggg cttaccatct ggccccagtg ctgcaatgat accgcgagac ccacgctcac    4260
cggctccaga tttatcagca ataaaccagc cagccggaag ggccgagcgc agaagtggtc    4320
ctgcaacttt atccgcctcc atccagtcta ttaattgttg ccgggaagct agagtaagta    4380
gttcgccagt taatagtttg cgcaacgttg ttgccattgc tacaggcatc gtggtgtcac    4440
gctcgtcgtt tggtatggct tcattcagct ccggttccca acgatcaagg cgagttacat    4500
gatcccccat gttgtgcaaa aaagcggtta gctccttcgg tcctccgatc gttgtcagaa    4560
gtaagttggc cgcagtgtta tcactcatgg ttatggcagc actgcataat tctcttactg    4620
tcatgccatc cgtaagatgc ttttctgtga ctggtgagta ctcaaccaag tcattctgag    4680
aatagtgtat gcggcgaccg agttgctctt gcccggcgtc aatacgggat aataccgcgc    4740
cacatagcag aactttaaaa gtgctcatca ttggaaaacg ttcttcgggg cgaaaactct    4800
caaggatctt accgctgttg agatccagtt cgatgtaacc cactcgtgca cccaactgat    4860
cttcagcatc ttttactttc accagcgttt ctgggtgagc aaaaacagga aggcaaaatg    4920
ccgcaaaaaa gggaataagg gcgacacgga aatgttgaat actcatactc ttccttttc    4980 aatattattg aagcatttat cagggttatt gtctcatgag cggatacata tttgaatgta    5040
tttagaaaaa taaacaaata ggggttccgc gcacatttcc ccgaaaagtg ccacctgacg    5100
cgccctgtag cggcgcatta agcgcggcgg gtgtggtggt tacgcgcagc gtgaccgcta    5160
cacttgccag cgccctagcg cccgctcctt tcgctttctt cccttccttt ctcgccacgt    5220
tcgccggctt tccccgtcaa gctctaaatc ggggctccc tttagggttc cgatttagtg    5280
ctttacggca cctcgacccc aaaaaacttg attagggtga tggttcacgt agtgggccat    5340
cgccctgata cacggttttt cgccctttga cgttggagtc cacgttcttt aatagtggac    5400
tcttgttcca aactggaaca acactcaacc ctatctcggt ctattctttt gatttataag    5460
ggattttgcc gatttcggcc tattggttaa aaaatgagct gatttaacaa aatttaacg    5520 cgaattttaa caaatatta acgtttacaa tttcccattc gccattcagg ctgcgcaact    5580
gttgggaagg gcgatcggtg cgggcctctt cgctattacg ccagcccaag ctaccatgat    5640
aagtaagtaa tattaaggta cgggaggtac ttggagcggc cgcaataaaa tatctttatt    5700
ttcattacat ctgtgtgttg gttttttgtg tgaatcgata gtactaacat acgctctcca    5760
tcaaaacaaa acgaaacaaa acaaactagc aaaataggct gtccccagtg caagtgcagg    5820
tgccagaaca tttctctatc gata                                           5844

<210> SEQ ID NO 12
<211> LENGTH: 2334
```

<212> TYPE: DNA
<213> ORGANISM: Mus musculus

<400> SEQUENCE: 12

```
tcgaggtcga cggtatcgat aagcttgggc tgcaggtcga tcgactctag aggatcgatc      60
cccaccatgg gtcaatcacg ctacctcctc tttttggcca cccttgccct cctaaaccac     120
ctcagtttgg ccagggtcat tccagtctct ggacctgcca ggtgtcttag ccagtcccga     180
aacctgctga agaccacaga tgacatggtg aagacggcca gagaaaaact gaaacattat     240
tcctgcactg ctgaagacat cgatcatgaa gacatcacac gggaccaaac cagcacattg     300
aagacctgtt taccactgga actacacaag aacgagagtt gcctggctac tagagagact     360
tcttccacaa caagagggag ctgcctgccc cacagaaga cgtctttgat gatgaccctg       420
tgccttggta gcatctatga ggacttgaag atgtaccaga cagagttcca ggccatcaac     480
gcagcacttc agaatcacaa ccatcagcag atcattctag acaagggcat gctggtggcc     540
atcgatgagc tgatgcagtc tctgaatcat aatggcgaga ctctgcgcca gaaacctcct     600
gtgggagaag cagaccctta cagagtgaaa atgaagctct gcatcctgct tcacgccttc     660
agcacccgcg tcgtgaccat caacagggtg atgggctatc tgagctccgc ctgagaattc     720
cgcccctctc cctccccccc cctaacgtt actggccgaa gccgcttgga ataaggccgg      780
tgtgcgtttg tctatatgtt attttccacc atattgccgt cttttggcaa tgtgagggcc     840
cggaaacctg gccctgtctt cttgacgagc attcctaggg gtctttcccc tctcgccaaa     900
ggaatgcaag gtcgtgttaa tgtcgtgaag gaagcagttc ctctggaagc ttcttgaaga     960
caaacaacgt ctgtagcgac cctttgcagg cagcggaacc ccccacctgg cgacaggtgc    1020
ctctgcggcc aaaagccacg tgtataagat acacctgcaa aggcggcaca cccccagtgc    1080
cacgttgtga gttggatagt tgtggaaaga gtcaaatggc tctcctcaag cgtattcaac    1140
aaggggctga aggatgccca gaaggtaccc cattgtatgg gatctgatct ggggcctcgg    1200
tgcacatgct ttacatgtgt ttagtcgagg ttaaaaaacg tctaggcccc ccgaaccacg    1260
gggacgtggt tttcctttga aaacacgat gataatatgg ccacaaccat gggtcctcag     1320
aagctaacca tctcctggtt tgccatcgtt ttgctggtgt ctccactcat ggccatgtgg    1380
gagctggaga agacgtttta tgttgtagag gtggactgga ctcccgatgc ccctggagaa    1440
acagtgaacc tcacctgtga cacgcctgaa gaagatgaca tcacctggac ctcagaccag    1500
agacatggag tcataggctc tggaaagacc ctgaccatca ctgtcaaaga gtttctagat    1560
gctggccagt acacctgcca caaggaggc gagactctga gccactcaca tctgctgctc     1620
cacaagaagg aaaatggaat tggtccact gaaattttaa aaaatttcaa aaacaagact      1680
ttcctgaagt gtgaagcacc aaattactcc ggacggttca cgtgctcatg gctggtgcaa    1740
agaaacatgg acttgaagtt caacatcaag agcagtagca gttcccctga ctctcgggca    1800
gtgacatgtg aatggcgtc tctgtctgca gagaaggtca cactggacca aagggactat    1860
gagaagtatt cagtgtcctg ccaggaggat gtcacctgcc caactgccga ggagaccctg    1920
cccattgaac tggcgttgga agcacggcag cagaataaat atgagaacta cagcaccagc    1980
ttcttcatca gggacatcat caaaccagac ccgcccaaga acttgcagat gaagcctttg    2040
aagaactcac aggtggaggt cagctgggag taccctgact cctggagcac tcccattcc     2100
tacttctccc tcaagttctt tgttcgaatc cagcgcaaga agaaaagat gaaggagaca     2160
gaggaggggt gtaaccagaa aggtgcgttc ctcgtagaga agacatctac cgaagtccaa    2220
```
tgcaaaggcg ggaatgtctg cgtgcaagct caggatcgct attacaattc ctcatgcagc    2280
aagtgggcat gtgttccctg cagggtccga tcctagaatt cattgatcca ctag          2334

<210> SEQ ID NO 13
<211> LENGTH: 2336
<212> TYPE: DNA
<213> ORGANISM: Homo sapiens

<400> SEQUENCE: 13
ctgcagacca tgggtccagc gcgcagcctc ctccttgtgg ctaccctggt cctcctggac      60
cacctcagtt tggccagaaa cctccccgtg gccactccag acccaggaat gttcccatgc     120
cttcaccact cccaaaacct gctgagggcc gtcagcaaca tgctccagaa ggccagacaa     180
actctagaat tttaccccttg cacttctgaa gagattgatc atgaagatat cacaaaagat     240
aaaaccagca cagtggaggc ctgtttacca ttggagttaa ccaagaatga gagttgccta     300
aattccagag agacctcttt cataactaat gggagttgcc tggcctccag aaagacctct     360
tttatgatgg ccctgtgcct tagtagtatt tatgaagact gaagatgta ccaggtggag     420 ttcaagacca tgaatgcaaa gcttctgatg gatcctaaga ggcagatctt tctagatcaa     480
aacatgctgg cagttattga tgagctgatg caggccctga atttcaacag tgagactgtg     540
ccacaaaaat cctcccttga agaaccggat ttttataaaa ctaaaatcaa gctctgcata     600
cttcttcatg ctttcagaat tcgggcagtg actattgata gagtgacgag ctatctgaat     660
gcttcctaac tgcagaaggg cgaattccag cacactggcg gccgttacta ggggctgcag     720
gaattccgcc cccccctctc cctccccccc ccctaacgtt actggccgaa gccgcttgga     780
ataaggccgg tgtgcgtttg tctatatgtt attttccacc atattgccgt cttttggcaa     840
tgtgagggcc cggaaacctg gccctgtctt cttgacgagc attcctaggg gtctttcccc     900
tctcgccaaa ggaatgcaag gtctgttgaa tgtcgtgaag gaagcagttc ctctggaagc     960
ttcttgaaga caaacaacgt ctgtagcgac cctttgcagg cagcggaacc cccacctgg    1020 cgacaggtgc ctctgcggcc aaaagccacg tgtataagat acacctgcaa agcggcacaa    1080
ccccagtgcc acgttgtgag ttggatagtt gtggaaagag tcaaatggct ctcctcaagc    1140
gtattcaaca aggggctgaa ggatgcccag aaggtacccc attgtatggg atctgatctg    1200
gggcctcggt gcacatgctt tacatgtgtt tagtcgaggt taaaaaaacg tctaggcccc    1260
ccgaaccacg gggacgtggt tttcctttga aaaacacgat gataatatgg ccacaaccat    1320
gggtcaccag cagttggtca tctcttggtt ttccctggtt tttctggcat ctcccctcgt    1380
ggccatatgg gaactgaaga agatgtttta tgtcgtagaa ttggattggt atccggatgc    1440
ccctggagaa atggtggtcc tcacctgtga caccectgaa gaagatggta tcacctggac    1500
cttggaccag agcagtgagg tcttaggctc tggcaaaacc ctgaccatcc aagtcaaaga    1560
gtttggagat gctggccagt cacctgtca caaaggaggc gaggttctaa gccattcgct    1620
cctgctgctt cacaaaaagg aagatggaat ttggtccact gatatttaa aggaccagaa    1680 agaacccaaa aataagacct ttctaagatg cgaggccaag aattattctg gacgtttcac    1740
ctgctggtgg ctgacgacaa tcagtactga tttgacattc agtgtcaaaa gcagcagagg    1800
ctcttctgac ccccaagggg tgacgtgcgg agctgctaca ctctctgcag agagagtcag    1860 agggggacaac aaggagtatg agtactcagt ggagtgccag gaggacagtg cctgcccagc    1920
tgctgaggag agtctgccca ttgaggtcat ggtggatgcc gttcacaagc tcaagtatga    1980
aaactacacc agcagcttct tcatcaggga catcatcaaa cctgacccac ccaagaactt    2040

```
gcagctgaag ccattaaaga attctcggca ggtggaggtc agctgggagt accctgacac    2100
ctggagtact ccacattcct acttctccct gacattctgc gttcaggtcc agggcaagag    2160
caagagagaa aagaaagata gagtcttcac ggacaagacc tcagccacgg tcatctgccg    2220
caaaaatgcc agcattagcg tgcgggccca ggaccgctac tatagctcat cttggagcga    2280
atgggcatct gtgccctgca gttagatatc aagcttatcg ataccgtcga cctcga        2336

<210> SEQ ID NO 14
<211> LENGTH: 3057
<212> TYPE: DNA
<213> ORGANISM: Escherichia coli

<400> SEQUENCE: 14
atggatcccg tcgttttaca acgtcgtgac tgggaaaaacc ctggcgttac ccaacttaat    60
cgccttgcag cacatccccc tttcgccagc tggcgtaata gcgaagaggc ccgcaccgat    120
cgcccttccc aacagttgcg cagcctgaat ggcgaatggc gctttgcctg gtttccggca    180
ccagaagcgg tgccggaaag ctggctggag tgcgatcttc ctgaggccga tactgtcgtc    240
gtcccctcaa actggcagat gcacggttac gatgcgccca tctacaccaa cgtaacctat    300
cccattacgg tcaatccgcc gtttgttccc acggagaatc cgacggggttg ttactcgctc    360 acatttaatg ttgatgaaag ctggctacag gaaggccaga cgcgaattat ttttgatggc    420
gttaactcgg cgtttcatct gtggtgcaac gggcgctggg tcggttacgg ccaggacagt    480
cgtttgccgt ctgaatttga cctgagcgca tttttacgcg ccggagaaaa ccgcctcgcg    540
gtgatggtgc tgcgttggag tgacggcagt tatctggaag atcaggatat gtggcggatg    600
agcggcattt tccgtgacgt ctcgttgctg cataaaccga ctacacaaat cagcgatttc    660
catgttgcca ctcgctttaa tgatgatttc agccgcgctg tactggaggc tgaagttcag    720
atgtgcggca gttgcgtgac ctacctacgg gtaacagttt cttatggca gggtgaaacg    780 caggtcgcca gcggcaccgc gcctttcggc ggtgaaatta tcgatgagcg tggtggttat    840
gccgatcgcg tcacactacg tctgaacgtc gaaaacccga actgtggag cgccgaaatc    900 ccgaatctct atcgtgcggt ggttgaactg cacaccgccg acggcacgct gattgaagca    960
gaagcctgcg atgtcggttt ccgcgaggtg cggattgaaa atggtctgct gctgctgaac    1020
ggcaagccgt tgctgattcg aggcgttaac cgtcacgagc atcatcctct gcatggtcag    1080
gtcatggatg agcagacgat ggtgcaggat atcctgctga tgaagcagaa caactttaac    1140
gccgtgcgct gttcgcatta tccgaaccat ccgctgtggt acacgctgtg cgaccgctac    1200
ggcctgtatg tggtggatga agccaatatt gaaacccacg gcatggtgcc aatgaatcgt    1260
ctgaccgatg atccgcgctg gctaccggcg atgagcgaac gcgtaacgcg aatggtgcag    1320
cgcgatcgta atcacccgag tgtgatcatc tggtcgctgg gaatgaatc aggccacggc    1380 gctaatcacg acgcgctgta cgctggatc aaatctgtcg atccttcccg cccggtgcag    1440
tatgaaggcg gcggagccga caccacggcc accgatatta tttgcccgat gtacgcgcgc    1500
gtggatgaag accagcccct cccggctgtg ccgaaatggt ccatcaaaaa atggcttttcg    1560 ctacctggag agacgcgccc gctgatcctt tgcgaatacg cccacgcgat gggtaacagt    1620
cttggcggtt tcgctaaata ctggcaggcg tttcgtcagt atccccgttt acagggcggc    1680
ttcgtctggg actgggtgga tcagtcgctg attaaatatg atgaaaacgg caaccccgtgg    1740 tcggcttacg gcggtgattt tggcgatacg ccgaacgatc gccagttctg tatgaacggt    1800
```

```
ctggtctttg ccgaccgcac gccgcatcca gcgctgacgg aagcaaaaca ccagcagcag    1860 ttttccagt tccgtttatc cgggcaaacc atcgaagtga ccagcgaata cctgttccgt    1920
catagcgata acgagctcct gcactggatg gtggcgctgg atggtaagcc gctggcaagc    1980
ggtgaagtgc ctctggatgt cgctccacaa ggtaaacagt tgattgaact gcctgaacta    2040
ccgcagccgg agagcgccgg gcaactctgg ctcacagtac gcgtagtgca accgaacgcg    2100
accgcatggt cagaagccgg gcacatcagc gcctggcagc agtggcgtct ggcggaaaac    2160
ctcagtgtga cgctccccgc cgcgtcccac gccatcccgc atctgaccac cagcgaaatg    2220 gattttttgca tcgagctggg taataagcgt tggcaattta accgccagtc aggctttctt    2280
tcacagatgt ggattggcga taaaaaacaa ctgctgacgc cgctgcgcga tcagttcacc    2340
cgtgcaccgc tggataacga cattggcgta agtgaagcga cccgcattga ccctaacgcc    2400
tgggtcgaac gctggaaggc ggcgggccat taccaggccg aagcagcgtt gttgcagtgc    2460
acggcagata cacttgctga tgcggtgctg attacgaccg ctcacgcgtg gcagcatcag    2520
gggaaaacct tatttatcag ccggaaaacc taccggattg atggtagtgg tcaaatggcg    2580
attaccgttg atgttgaagt ggcgagcgat acaccgcatc cggcgcggat tggcctgaac    2640
tgccagctgg cgcaggtagc agagcgggta aactggctcg gattagggcc gcaagaaaac    2700
tatcccgacc gccttactgc cgcctgtttt gaccgctggg atctgccatt gtcagacatg    2760 tatacccgt acgtcttccc gagcgaaaac ggtctgcgct gcgggacgcg cgaattgaat    2820
tatgccccac accagtggcg cggcgacttc cagttcaaca tcagccgcta cagtcaacag    2880
caactgatgg aaaccagcca tcgccatctg ctgcacgcgg aagaaggcac atggctgaat    2940
atcgacggtt tccatatggg gattggtggc gacgactcct ggagcccgtc agtatcggcg    3000
gaattccagc tgagcgccgg tcgctaccat taccagttgg tctggtgtca aaaataa       3057

<210> SEQ ID NO 15
<211> LENGTH: 336
<212> TYPE: DNA
<213> ORGANISM: Homo sapiens

<400> SEQUENCE: 15
ctgcgctgtc gggggccaggc cgggctccca gtggattcgc gggcacagac gcccaggacc     60
gcgcttccca cgtggcggag ggactgggga cccgggcacc cgtcctgccc cttcaccttc    120
cagctccgcc tcctccgcgc ggaccccgcc ccgtcccgac ccctcccggg tcccggccc    180 agccccctcc gggccctccc agcccctccc cttcctttcc gcggcccccgc cctctcctcg    240 cggcgcgagt ttcaggcagc gctgcgtcct gctgcgcacg tgggaagccc tggccgatgg    300
gctcgacgca cgtgggcgca cgtgggcgca cgtggg                              336

<210> SEQ ID NO 16
<211> LENGTH: 27
<212> TYPE: DNA
<213> ORGANISM: Artificial Sequence
<220> FEATURE:
<223> OTHER INFORMATION: Synthetic construct

<400> SEQUENCE: 16
ctctagattt tctgccccaa agagctc                                         27

<210> SEQ ID NO 17
<211> LENGTH: 28
<212> TYPE: DNA
<213> ORGANISM: Artificial Sequence
```

```
-continued

<220> FEATURE:
<223> OTHER INFORMATION: Synthetic construct

<400> SEQUENCE: 17
cgggatcctg ttattggcag tggtggaa                                          28

<210> SEQ ID NO 18
<211> LENGTH: 28
<212> TYPE: DNA
<213> ORGANISM: Artificial Sequence
<220> FEATURE:
<223> OTHER INFORMATION: Synthetic construct

<400> SEQUENCE: 18
cggaattcgc ctgtcataca gctaataa                                          28

<210> SEQ ID NO 19
<211> LENGTH: 27
<212> TYPE: DNA
<213> ORGANISM: Artificial Sequence
<220> FEATURE:
<223> OTHER INFORMATION: Synthetic construct

<400> SEQUENCE: 19
ctctagactg tcaaataagt ggcctgg                                           27

<210> SEQ ID NO 20
<211> LENGTH: 76
<212> TYPE: DNA
<213> ORGANISM: Artificial Sequence
<220> FEATURE:
<223> OTHER INFORMATION: Synthetic construct

<400> SEQUENCE: 20
actagttaac aggcattgcc tgaaaagagt ataaaagaat ttcagcatga ttttccatgg        60
cggatgtgtg acatac                                                       76

<210> SEQ ID NO 21
<211> LENGTH: 26
<212> TYPE: DNA
<213> ORGANISM: Artificial Sequence
<220> FEATURE:
<223> OTHER INFORMATION: Synthetic construct

<400> SEQUENCE: 21
ctcgaggata tccaagatga gtgtgt                                            26
```